US012637674B2

(12) United States Patent
Rosenzweig et al.

(10) Patent No.: US 12,637,674 B2
(45) Date of Patent: May 26, 2026

(54) INHIBITION OF lncExACT1 TO TREAT HEART DISEASE

(71) Applicant: The General Hospital Corporation, Boston, MA (US)

(72) Inventors: Anthony Rosenzweig, Newton, MA (US); Haobo Li, Allston, MA (US)

(73) Assignee: The General Hospital Corporation, Boston, MA (US)

( * ) Notice: Subject to any disclaimer, the term of this patent is extended or adjusted under 35 U.S.C. 154(b) by 592 days.

(21) Appl. No.: 18/018,478

(22) PCT Filed: Jul. 29, 2021

(86) PCT No.: PCT/US2021/043616

§ 371 (c)(1),
(2) Date: Jan. 27, 2023

(87) PCT Pub. No.: WO2022/026648

PCT Pub. Date: Feb. 3, 2022

(65) Prior Publication Data

US 2023/0287427 A1 Sep. 14, 2023

Related U.S. Application Data

(60) Provisional application No. 63/058,268, filed on Jul. 29, 2020.

(51) Int. Cl.

| | |
|---|---|
| *C07H 21/02* | (2006.01) |
| *A61K 47/69* | (2017.01) |
| *A61P 9/04* | (2006.01) |
| *C07H 21/04* | (2006.01) |
| *C12N 15/113* | (2010.01) |
| *C12N 15/86* | (2006.01) |

(52) U.S. Cl.
CPC ...... *C12N 15/1136* (2013.01); *A61K 47/6929* (2017.08); *A61P 9/04* (2018.01); *C12N 15/86* (2013.01); *C12N 2310/11* (2013.01); *C12N 2310/3515* (2013.01); *C12N 2310/531* (2013.01); *C12N 2740/15043* (2013.01)

(58) Field of Classification Search
CPC .............. C12N 15/113; C12N 2310/11; C12N 2310/14
See application file for complete search history.

(56) References Cited

U.S. PATENT DOCUMENTS

| | | |
|---|---|---|
| 2012/0165392 A1 | 6/2012 | Olson et al. |
| 2014/0045758 A1 | 2/2014 | Goldberg et al. |
| 2017/0114409 A1 | 4/2017 | Thum et al. |
| 2018/0305659 A1* | 10/2018 | Skaar ....................... C12N 1/20 |

FOREIGN PATENT DOCUMENTS

WO WO-2013173601 A1 * 11/2013 .............. A61P 25/28

OTHER PUBLICATIONS

Bertrand et al. (Biochemical and Biophysical Research Communications, 296, 2002, 1000-1004).*
De Paula et al. (RNA, 2007, 13, 431-456).*
Vickers et al. (The Journal of Biological Chemistry, vol. 278, No. 9, 7108-7118, 2003).*
Seth et al. (Molecular Therapy-Nucleic Acids (2012) 1, e47, 1-8).*
Elbashir et al. (The EMBO Journal, vol. 20, No. 23, pp. 6877-6888, 2001).*
Parrish et al. (Molecular Cell, vol. 6, 1077-1087, Nov. 2000).*
Fujita et al. (Int. J. Mol. Sci. 2015, 16, 5254-5270).*
Bagherie-Lachidan et al., "Stromal Fat4 acts non-autonomously with Dchs1/2 to restrict the nephron progenitor pool," Development, Aug. 2015, 142(15):2564-2573.
Bansal et al., "Proteomic analysis reveals late exercise effects on cardiac remodeling following myocardial infarction," J Proteomics, Sep. 2010, 73(10):2041-2049, 16 pages.
Bezzerides et al., "CITED4 induces physiologic hypertrophy and promotes functional recovery after ischemic injury," JCI Insight, Jun. 2016, 1(9):e85904, 15 pages.
Blair and McNeill, "Big roles for Fat cadherins," Curr Opin Cell Biol., Apr. 2018, 51:73-80.
Boeckel et al., "Identification and regulation of the long non-coding RNA Heat2 in heart failure," J Mol Cell Cardiol., Jan. 2019, 126:13-22.
Boström et al., "C/EBPB Controls Exercise-Induced Cardiac Growth and Protects against Pathological Cardiac Remodeling," Cell, Dec. 2010, 143(7):1072-1083.
Cai et al., "The Long Noncoding RNA Carel Controls Cardiac Regeneration," Journal of the American College of Cardiology, Jul. 2018, 72(5):534-550.
Campos et al., "Exercise reestablishes autophagic flux and mitochondrial quality control in heart failure," Autophagy, Aug. 2017, 13(8):1304-1317.
Collins et al., "Regulation of Long Non-coding RNAs and MicroRNAs in Heart Disease: Insight into Mechanisms and Therapeutic Approaches," Front Physiol., Jul. 2020, 11:798, 20 pages.
Craig et al., "Dysregulation of cadherins in the intercalated disc of the spontaneously hypertensive stroke-prone rat," J Mol Cell Cardiol., Jun. 2010, 48(6):1121-1128.
Devaux et al., "Long noncoding RNAs in cardiac development and ageing," Nat Rev Cardiol, Jul. 2015, 12(7):415-425, 11 pages.

(Continued)

*Primary Examiner* — Amy Rose Hudson
(74) *Attorney, Agent, or Firm* — Fish & Richardson P.C.

(57) ABSTRACT

The disclosure provides compositions comprising an inhibitory nucleic acid targeting lncExACTI, and methods of use thereof to improve cardiac function in a subject in need thereof. Specifically, the disclosure provides a cardiac long noncoding RNA (lncRNA), referred as lncExACT 1 (SEQ ID NO: 1), and inhibitory nucleic acids targeting lncExACT 1 for reducing expression of lncExACT 1 and/or Dachsous cadherin-related 2 (DCHS2) in a cell, e.g., a cell in a subject for improving cardiac function in a subject, wherein the subject has pathological cardiac hypertrophy and/or heart failure.

27 Claims, 52 Drawing Sheets

Specification includes a Sequence Listing.

(56)          References Cited

OTHER PUBLICATIONS

Eschenhagen et al., "Cardiomyocyte Regeneration: A Consensus Statement," Circulation, Aug. 2017, 136(7):680-686, 12 pages.

Gangwar et al., "Noncoding RNAs in Cardiovascular Disease: Pathological Relevance and Emerging Role as Biomarkers and Therapeutics," Am J Hypertens., Jan. 2018, 31(2):150-165.

GenBank Accession No. NG_054879, "*Homo sapiens* dachsous cadherin-related 2 (DCHS2), RefSeqGene on chromosome 4," Jun. 3, 2019, 5 pages.

Gibb and Hill, "Metabolic coordination of physiological and pathological cardiac remodeling," Circ Res., Jun. 2018, 123(1):107-128.

Grazette and Rosenzweig, "Role of apoptosis in heart failure," Heart Fail Clin, Jul. 2005, 1(2):251-261.

Grote et al., "The tissue-specific lncRNA Fendrr is an essential regulator of heart and body wall development in the mouse," Dev Cell., Jan. 2013, 24(2):206-214.

Guo et al., "Intercalated disc protein Xinβ is required for Hippo-YAP signaling in the heart," Nature Communications, Sep. 2020, 11(1):4666, 11 pages.

Han et al., "A long noncoding RNA protects the heart from pathological hypertrophy," Nature, Oct. 2014, 514(7520):102-106, 16 pages.

Han et al., "LncRNA CASC2 inhibits hypoxia-induced pulmonary artery smooth muscle cell proliferation and migration by regulating the miR-222/ING5 axis," Cell Mol Biol Lett., Mar. 2020, 25:21, 16 pages.

Heallen et al., "Hippo pathway inhibits Wnt signaling to restrain cardiomyocyte proliferation and heart size," Science, Apr. 2011, 332(6028):458-461.

Huang et al., "Preclinical and Clinical Development of Noncoding RNA Therapeutics for Cardiovascular Disease," Circ Res, Feb. 2020, 126(5):663-678, 28 pages.

Iemitsu et al., "Physiological and pathological cardiac hypertrophy induce different molecular phenotypes in the rat," Am J Physiol Regul Integr Comp Physiol, Dec. 2001, 281(6):R2029-2036.

Ikeda et al., "Hippo Deficiency Leads to Cardiac Dysfunction Accompanied by Cardiomyocyte Dedifferentiation During Pressure Overload," Circ Res, Jan. 2019, 124(2):292-305, 23 pages.

International Preliminary Report on Patentability in International Appln. No. PCT/US2021/043616, mailed on Feb. 9, 2023, 10 pages.

International Search Report and Written Opinion in International Appln. No. PCT/US2021/043616, mailed on Nov. 26, 2021, 16 pages.

Jiang and Ning, "The emerging roles of long noncoding RNAs in common cardiovascular diseases," Hypertens Res., Jun. 2015, 38(6):375-9.

Jiang et al., "Allele-specific silencing of mutant Myh6 transcripts in mice suppresses hypertrophic cardiomyopathy," Science, Oct. 2013, 342(6154):111-114.

Kikuchi et al., "Primary contribution to zebrafish heart regeneration by gata4+ cardiomyocytes," Nature, Mar. 2010, 464(7288):601-5.

Klattenhoff et al., "Braveheart, a long noncoding RNA required for cardiovascular lineage commitment," Cell, Jan. 2013, 152(3):570-583.

Liu et al., "miR-222 is necessary for exercise-induced cardiac growth and protects against pathological cardiac remodeling," Cell Metab, Apr. 2015, 21(4):584-595.

Mann and Rosenzweig, "Can exercise teach us how to treat heart disease?," Circulation, Nov. 2012, 126(22):2625-2635, 22 pages.

Micheletti et al., "The long noncoding RNA Wisper controls cardiac fibrosis and remodeling," Sci Transl Med., Jun. 2017, 9(395):eaai9118, 17 pages.

Monroe et al., "YAP Partially Reprograms Chromatin Accessibility to Directly Induce Adult Cardiogenesis In Vivo," Dev Cell, 2019, 48(6):765-779.e767.

Morikawa et al., "Dystrophin-glycoprotein complex sequesters Yap to inhibit cardiomyocyte proliferation," Nature, Jul. 2017, 547(7662):227-231, 17 pages.

Mozaffarian et al., "Heart disease and stroke statistics—2015 update: a report from the American Heart Association," Circulation, Jan. 2015, 131(4):e29-322.

Nakamura and Sadoshima, "Mechanisms of physiological and pathological cardiac hypertrophy," Nat Rev Cardiol., Jul. 2018, 15(7):387-407.

Narula et al., "Apoptosis in myocytes in end-stage heart failure," New England Journal Of Medicine, Oct. 1996, 335(16):1182-1189.

Osborn et al., "Improving siRNA Delivery In Vivo Through Lipid Conjugation," Nucleic Acid Ther., Jun. 2018, 28(3):128-136.

Pandey et al., "Relationship Between Physical Activity, Body Mass Index, and Risk of Heart Failure," J Am Coll Cardiol, Mar. 2017, 69(9):1129-1142.

Pendergraff et al., "Locked Nucleic Acid Gapmers and Conjugates Potently Silence ADAM33, an Asthma-Associated Metalloprotease with Nuclear-Localized mRNA," Mol Ther Nucleic Acids, Sep. 2017, 8:158-168, 17 pages.

Platt et al., "CRISPR-Cas9 knockin mice for genome editing and cancer modeling," Cell, Oct. 2014, 159(2):440-55.

Pleger et al., "Cardiac AAV9-S100A1 Gene Therapy Rescues Post-Ischemic Heart Failure in a Preclinical Large Animal Model," Sci Transl Med., Jul. 2011, 3(92):92ra64, 20 pages.

Poss et al., "Heart regeneration in zebrafish," Science, Dec. 2002, 298(5601):2188-90.

Rinaldi and Wood, "Antisense oligonucleotides: the next frontier for treatment of neurological disorders," Nat Rev Neurol, Jan. 2018, 14(1):9-21, 13 pages.

Roh et al., "Activin type II receptor signaling in cardiac aging and heart failure," Sci Transl Med., Mar. 2019, 11(482):eaau8680, 16 pages.

Roh et al., "Exercise training reverses cardiac aging phenotypes associated with heart failure with preserved ejection fraction in male mice," Aging Cell., Jun. 2020, 19(6):e13159, 12 pages.

Sallam et al., "Long Noncoding RNA Discovery in Cardiovascular Disease: Decoding Form to Function," Circ Res, Jan. 2018, 122(1):155-166.

Sharma and McNeill, "Fat and Dachsous cadherins," Prog Mol Biol Transl Sci., 2013, 116:215-235.

Song et al., "Deep RNA sequencing reveals novel cardiac transcriptomic signatures for physiological and pathological hypertrophy," PLoS One, 2012, 7(4):e35552, 13 pages.

Steinhauser et al., "Multi-isotope imaging mass spectrometry quantifies stem cell division and metabolism," Nature, Jan. 2012, 481:516-519.

Totaro et al., "YAP/TAZ upstream signals and downstream responses," Nat Cell Biol, Aug. 2018, 20(8):888-899.

Tsao et al., "Left ventricular structure and risk of cardiovascular events: A Framingham heart study cardiac magnetic resonance study," J Am Heart Assoc., Sep. 2015, 4(9):e002188, 14 pages.

Viereck and Thum, "Long Noncoding RNAs in Pathological Cardiac Remodeling," Circ Res, Jan. 2017, 120(2):262-264, 5 pages.

Viereck et al., "Long noncoding RNA Chast promotes cardiac remodeling," Sci Transl Med., Feb. 2016, 8(326):326ra322, 13 pages.

Virani et al., "Heart Disease and Stroke Statistics—2020 Update: A Report From the American Heart Association," Circulation, Mar. 2020, 141(9):e139-e596, 771 pages.

Vujic et al., "Exercise induces new cardiomyocyte generation in the adult mammalian heart," Nat Commun, Apr. 2018, 9(1):1659, 9 pages.

Wang et al., "Aerobic exercise protects against pressure overload-induced cardiac dysfunction and hypertrophy via β3-AR-nNOS-NO activation," PLoS One, Jun. 2017, 12:e0179648, 23 pages.

Wang et al., "The Hippo pathway in the heart: pivotal roles in development, disease, and regeneration," Nat Rev Cardiol, Nov. 2018, 15(11):672-684, 13 pages.

Wang et al., "The long noncoding RNA NRF regulates programmed necrosis and myocardial injury during ischemia and reperfusion by targeting miR-873," Cell Death Differ, Jun. 2016, 23:1394-1405.

Wei and Rosenzweig, "What do we know about the cardiac benefits of exercise?," Trends Cardiovasc Med, Aug. 2015, 25(6):529-536.

(56)          References Cited

OTHER PUBLICATIONS

Yengo et al., "Exercise training post-mi favorably modifies heart extracellular matrix in the rat," Med Sci Sports Exerc., Jun. 2012, 44(6):1005-1012.

* cited by examiner

Heart

Plasma

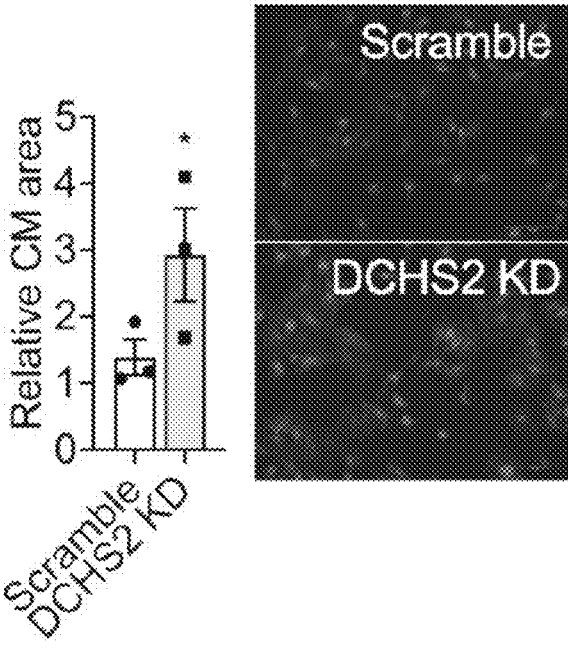
*FIG. 6D*
*FIG. 6E*
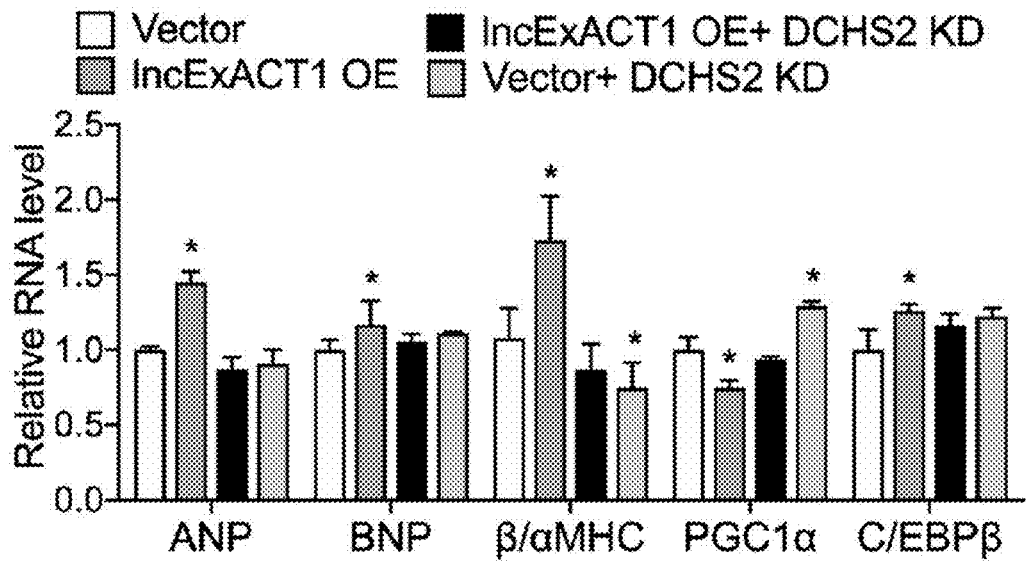
*FIG. 6F*

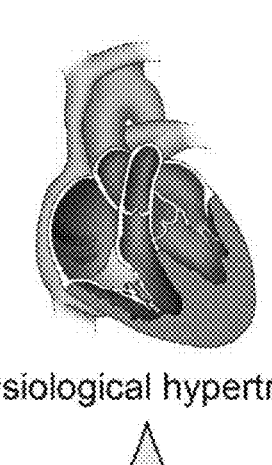
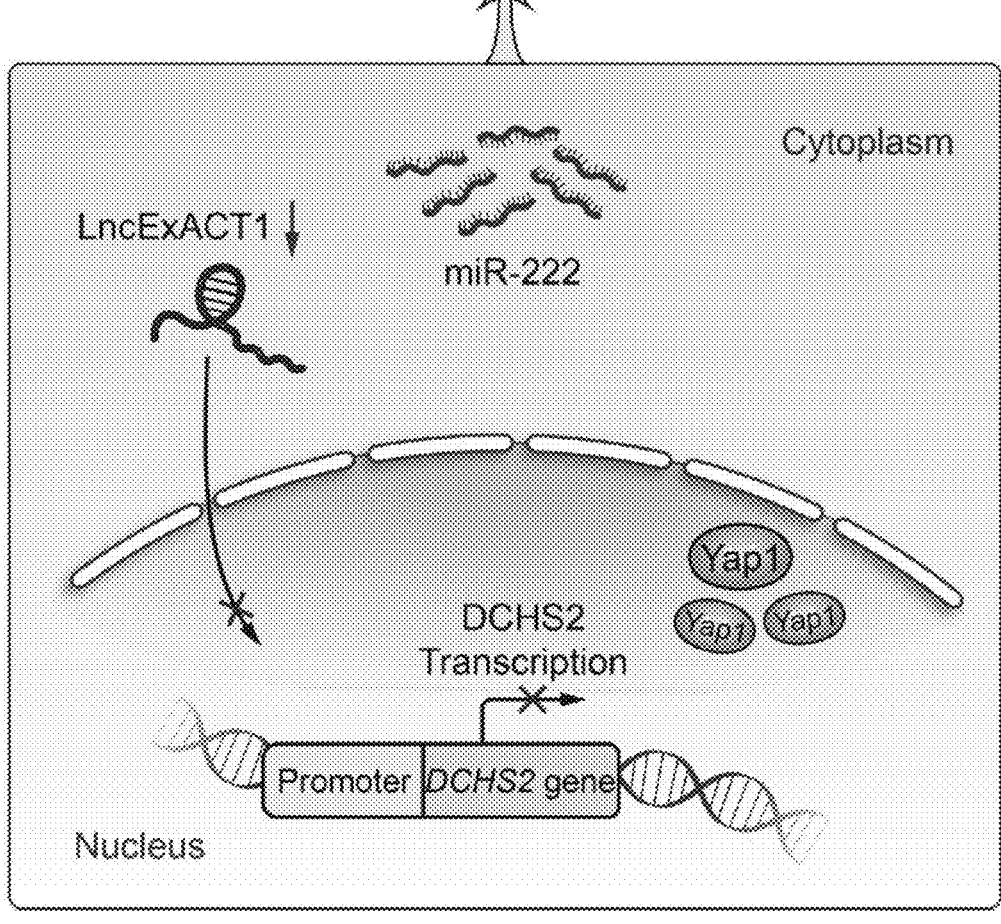
FIG. 7, continued

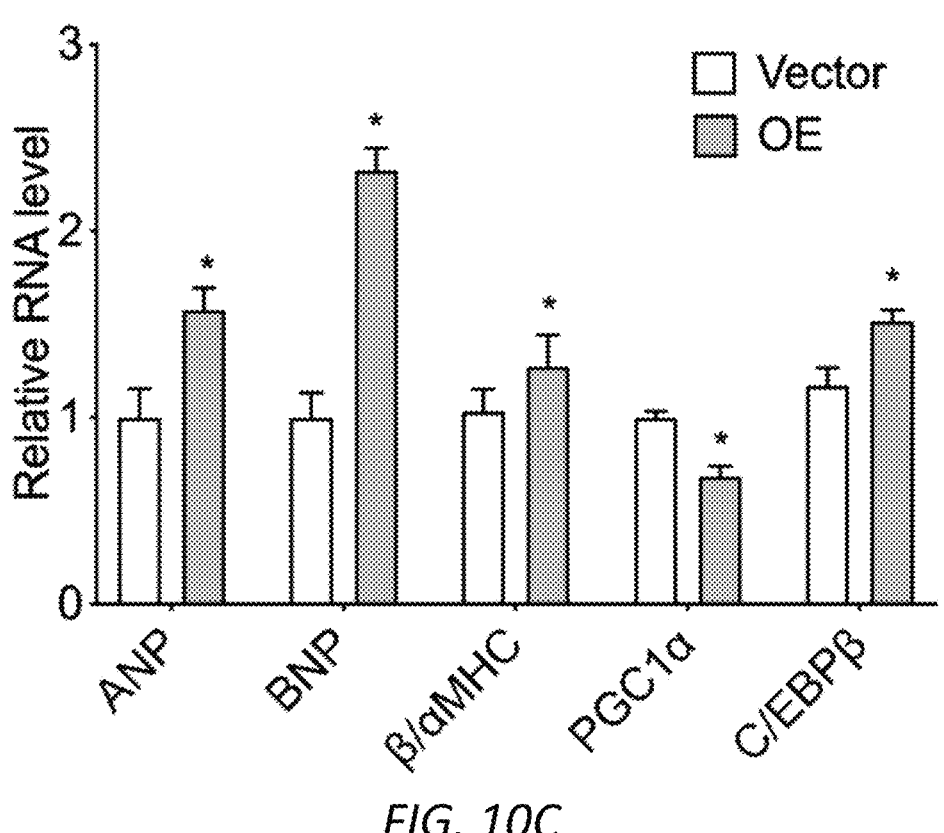
FIG. 10C
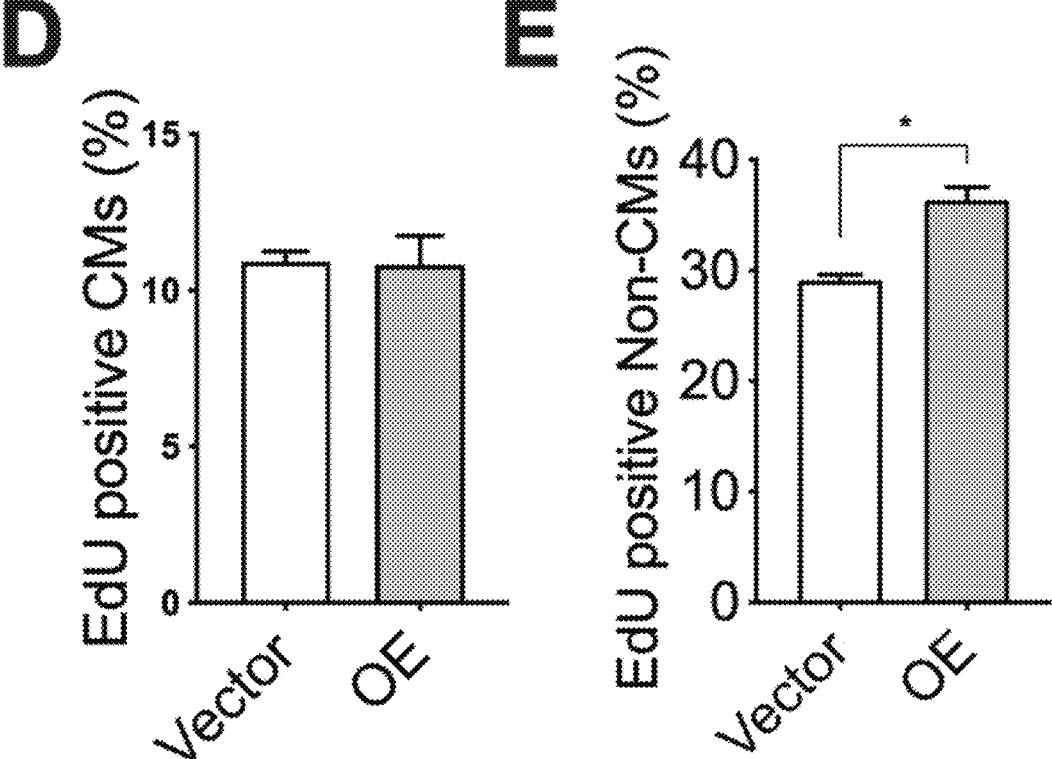
FIGs. 10D-E

```
mmu-miR-1928     Target:  5'  ggcCAGCCAUAUGUAGCa  3'
                                 |  |  ||  |||||||
                 miRNA  :  3'  cucGACCGU-UACAUCGa  5' mmu-miR-222-3p   Target:  5'  agcggccAGCCAUAUGUAGCa  3'
                                     |||||  |||||||
                 miRNA  :  3'  ugggucaUCGGUCUACAUCGa  5' mmu-miR-221-3p   Target:  5'  gaGAGCGGCCAGCCAUAUGUAGCa  3'
                                :|  |  :  |||  ||  |||||||
                 miRNA  :  3'  cuUUGGGUCGUCUGU-UACAUCGa  5' mmu-miR-664-5p   Target:  5'  cucuugagagcggCCAGCCAu  3'
                                             |||||||
                 miRNA  :  3'  ggucaguaaaaggGGUCGGUc  5' mmu-miR-876-5p   Target:  5'  aaagaaaacuuccAGAAAUCCc  3'
                                            |||||||||
                 miRNA  :  3'  aucacuaagugucUCUUUAGGu  5'
```

FIG. 12A

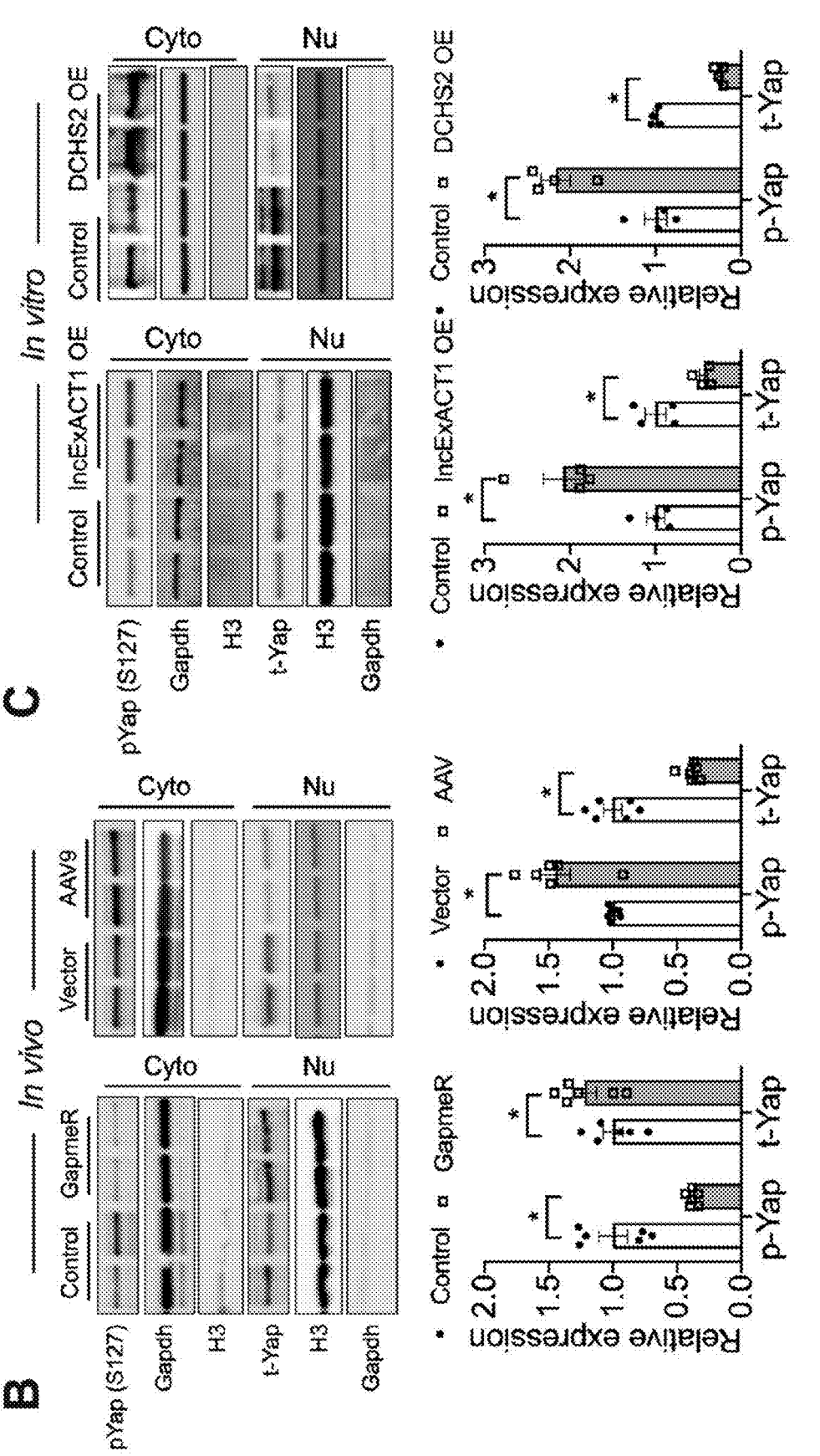
FIG. 14B-C

SEQUENCE LISTING

```
<160> NUMBER OF SEQ ID NOS: 132

<210> SEQ ID NO 1
<211> LENGTH: 1260
<212> TYPE: DNA
<213> ORGANISM: Homo sapiens

<400> SEQUENCE: 1
gcgactcctg ctccgaccca gcctccgccg cctgccttcc cctccctgcc gtgtgatgcg      60
gcgcacacga gggcaaactc caacctgcga gccgcgctct gcagcagggc ggaagaggag     120
caaatgcaaa agcactggga gacgtgcacc gcggggcggg tggggacgc gcaggcgggg     180 cgtctgcctg ggcttggcca agtgccaagt gatgatgggt gcggggaggt gagaggagcg     240
gcctctccgc ggcctccccc tccatccgct tgaccgtccc tctgcaggcc tgactcttgg     300
ctcgcgctga gccaagaggg tagaggttat catcactttg gggtgccaaa cttgtgttct     360
ccatttggcg agagggactc ccgtccgcag cggaaggaca gatggagtca aaggccgatg     420
catagctggg gccaggatgg ctttaaaggg gagaaggcgg aacttggaaa agccttccag     480
aaaacccgag aaatctgtgg cacacatggt gcaaaccaca ctttattatg cgtgctacta     540
cccagcgacg tgtgagcctc ttgtcactcc cctctgccac caggaatgac gacaatatat     600
ccgccctgag aacccttttt ctacattcag cgccatcata acacttccag gatgtctgac     660
gatgctgact gatgagcaga aagccctggt ggctgacacc ccgcaagccc tcagcgctcc     720
cccaccaccc ctaggcaagg aagtgtgcaa gcgggataac tctacggata ccactttcaa     780
aactagcttc tgtctgagcc gaacgcaaat gccaataaat agccatagtc gcagatttcc     840
```

-continued

```
cttcaattaa ctataataat cggtagaaac tgatcaatgg cctctaataa agtacgcctg        900
agaaaagact ctctggactc ttaaaaatgg ctgaccatat ttagcaagtg gtttctgcaa        960
ttttgcattt gggcctgaga gaagaattaa tttcctagat accgtttctc tcctttaggg       1020
aggaccaaaa gccctgcata gtggtttctt gcagcaacaa caaaatgcct ttttaaatgt       1080
gcaacggagg tgtatgtaat tgctaatcca cagccacacc gttatctcta cctgtgacca       1140
aataacaata aaataattga ctttgtagca tatatgttac cgaaaatggg gacattatta       1200
aaataaattc agctttcttt cccccaatga actctcttta accattaaag agatttgtta       1260
```

```
<210> SEQ ID NO 2
<211> LENGTH: 3971
<212> TYPE: DNA
<213> ORGANISM: Mus sp.

<400> SEQUENCE: 2
ctctgggtca ccgtcggcat cggacactga gactcgagcc acgtagtcgc ctgggtgggc         60
gccctcagag acctggaccg cacctccctc ggtgaggaag agcaggtgga tggcaggagg        120
gttgtcattc acgtccagca cgtcaatgga cacgcgcacg gtggctacct ctggctcggc        180 gccccgtcg cgggcctgga ccaccaactg gtgccaggcc tgctcctccc ggtctaaagg         240
tctttgcacc cgcactacgc cgctcagctc ctccacagaa aaataacccg gatcgcccag        300
tggcccacca cctgcgctcg ccacgggcac ttgccgctcc cggatactgt agcgtaccaa        360
gccattgggg cccaagtcgc gatcagtagc acgcacgcga caaacctcag agcccggctg        420
ggcgtcctca cgtactgtgg cgcggtactc gccctgctcg aaaactggcg ggttgtcgtt        480
ctcatccaac acacgcagct gcacgtgcag gaggccggtg cgccgagggc tgccaccgtc        540
ccaagcttca atgtgcagct cgtgcgctgc cgccgcctct cggtccaagc gccgcagcag        600
caccaagtct aagggttcca gcggtgatga ggacaccggc agggaaggcg acgccggtaa        660
ccccggcgtc ccatagcgca attggaagaa gggtcctgtg ggatcctggg gcatgtcaga        720
agcttgcagc aaagtgtagc cctggatgct gaacagtccc gcgtccgggt cctgggctcc        780
tggcaggcgg aacgctgtcc cgggcgggct gagttcggac acgtccagct gcagggagtc        840
gcggggaaag cgaggggaat ggtcgttcac gtcgttgacg cggatctcca cctgtaccac        900
ctctcccaac agcgtggcgg ccacgaagct atagtggtcc tgtcgctcgc ggtccagacg        960
ccgagcggtg cggatgatac cagtgtccgg gtgcacgtgg aagtcgtcca gcagcgggga       1020
gtcatccgag tcctccgaaa gaaaaaagcc attcccatcc tgttgctgag ctgctggcaa       1080
ccccgcgcga atgtcaccca ccagtgtgtc tgggggcagc ccctcgtcca ccgagaggct       1140
gaggttgaac acctgggcag atgagcccga ggctgcccac agccaggcgt ggacgaaaag       1200
ccggagcagg gagctctgcg ccccggcgcc gcggggccgc ccacggggtg acccagccgg       1260
ctgacgccct tcacccatcc ttcgcccagc agggctcatt tctcctccag ctctttagga       1320
agaaggctcc ggctagctgc cagcttgtat tgggatctca gagcaaccca ggagcctctt       1380
cagtattaag ccagggaaga aaagactttg caaacaaac gaaaagaccc gggagttccc        1440
aaggtggcat ctgcaactgg tgcagacgtc ctctggccgc agctcacgca ggcgggggcg       1500
gctctagctg cctctgcctc cgcggccacc tctccagcct ctggatgtct ttaagggagt       1560
cccatcgctt tttctctctt cttctattcc ttttacatct gttccttgtt ctgctcggct       1620
ggctgtttcc ccctggtaaa gtcaggtgca ttatttcttt tgccaaaaag gaggaaatta       1680
tttaaagcgc gcacacggag aggaagggga tccggccggg aaggggtgg agaaagggcg        1740
```

```
gggaggccga gggggcgcgg ggcgggagga acggtgggag gggccgctcg ggcagcagac   1800
tgctacaggg gcggccgctc ccccacccac cccactccac ctcccgcgtc tcccggcgct   1860
ggggactccg tggagccccc tctgactggg cctcctactc cttagtcccc tccccgtgcg   1920
tgatgcggct cgcaccggga tgaattccaa cctgcgagcc tcggttctgt agaaggacta   1980
aaaaacggct agccggatgg acacgcagcc ccagacagtg acgctgatgg ggttgtctgg   2040
cttggctttg cgtgcaaagt gtactgggtt agggaagagg ccagtagctt gcccctaagc   2100
tcgctctctc catcctcaga acagccctg cagcgagcct gcccatggct ccatgtaagg   2160
tgggggttat atggtcactt taaggagaca aacttgtgct ctctatttgg cgagagaacc   2220
ccacctcctc agcggaagga cagatggagt caaaaggaga tgcacagctg gggccagttt   2280
gactgtaaag cagggaaggc ggaacttgga gaaaaaaaa agaagaagaa gaaaggagaa   2340
agaaaacttc cagaaatccc gaaaaaatct gtgacacaca tggcacgctt tattatgccg   2400
agctactatt tagcagcgtg ctagtgtctt gtcactcccc tctgccacct gtgatgacaa   2460
caatggatgg agcttgcgga ccttttttagg catccagcgc catcatacct gccagcatat   2520
tttatgatga tgatttatgt gcggattgac cttgtggcat aagccccagc acacggcttt   2580
acctccagcc ctatgagaag aaccttgcag ggatctgata gctcttccaa agtagcttag   2640
ggttgaatcc aaagacaatt cacctcagcc tgtgtagtct cgggcttctc tcctgctatc   2700
cacagctata gatggaaact gacaaatggc ctctaataaa gtatgctcca ccagaggagt   2760
ctgctctctt gagagcggcc agccatatgt agcaaaaggt ttctgcaatt ttgcatttca   2820
gccagaagga agaattaatt tcctagatac tgttctgtgc taggggggaga ccaaaaggcc   2880 agcatacagt tccccagaaa ccccagtgaa acgccttctt atattgagtg gcctatgcat   2940
gccattgcta attagcagcc acaccaacct gtacccctga aaaaataata atcaaatgat   3000
tttcttggca gtgttgtatg taaccagaga tgctattaaa ataatgtcag cctccctttt   3060
atcgatcaag tgcctttaag catttgggag atcaggcttg agcctttgga gtcttctttc   3120
caacttaatg caaaggcatc aggagtctta caaagcacca caactactgc caccactggt   3180
cccttctgag gtggttctcc accaagcatt cagactgttt ctaaagccaa cactaagcct   3240 ttaacccta ttcagaacct acatgatagc ttcttgtttc agactccttc ctaaattgcc   3300
caccttgctc ttcttccctg ctcattgaag aatctttgag ttgttgagct tccctgtcta   3360
gatctctttt tgcccccccc cccaaacagg ctccttctcc ttcaggtctc atgtaagatg   3420
ccaactgagg ggacatctcc ctgactaccc tccttctagt gggagggtaa acctagatcc   3480
tcacattcta tttcattcaa agtgccttta agtacctgag atcagcttgt ttggttcatc   3540
tgcttggtct attactccaa tcttaccctc ttcatagact taaagcgctg ctttaaccca   3600
ctccccatga gagagtctga gagagtgttt ggtgaatagt agatcactct tcactgtatg   3660
tatccagtgg ctggaataac tgataggcag ataaatggat gaactttttaa actggaactt   3720 ggaaaccaca actaaagagt aactggccct gaggtccttc actgtactga gtcccagctt   3780
tgccttgctg gttttactca tcctgtgaat ctcctttgaa ccttttcagc ttatgtgaaa   3840
ctatcatcgt ccaatatttc cttggcacta agagaaaaag cggatcttct tcctgcacat   3900
ggcactgaca cggactttgt taacagaggt ttagttttga acaaatggga aaataaagct   3960
ttggaaacct g                                                       3971
```

<210> SEQ ID NO 3

```
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
taaaggcact tgatcg                                                          16

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aacacgtcta tacgc                                                           15

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcattcctgg tggcag                                                          16

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcgagcctcg gttctgta                                                        18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccatcagcg tcactgtct                                                       19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tggccagcca tatgtaggga                                                      20

<210> SEQ ID NO 9
<211> LENGTH: 21
```

<212> TYPE: DNA
<213> ORGANISM: Artificial Sequence
<220> FEATURE:
<223> OTHER INFORMATION: Description of Artificial Sequence: Synthetic
     primer

<400> SEQUENCE: 9
ttttgtcagg ggtacagggt g                                              21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 10
ggccaagtgc caagtgatga                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
agctatgcat cggcctttga                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
ggcataaagg gaacgaggga                                                20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 13
gcacaattct gagcttggac c                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 14
cgtggaagga ccctagtgaa g                                              21

<210> SEQ ID NO 15
<211> LENGTH: 20
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 15
tgcaagggac agaacaccat                                               20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tgcagtggga agagcatacc                                               20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagttccctt gtgcagggtt                                               20

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctgcaggac tgattgtttt atgct                                         25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtctgtctg tctctctctc tctct                                         25

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
catctcttca gattatcctg ctc                                           23

<210> SEQ ID NO 21
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 21
tcatgtgaaa ggatcgaggt                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgcaggtaaa agcctcggac                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctccacttcc acccgaacaa                                                    20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gagtttgaaa ggcctaagta cac                                                23

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctgaggagtt caagggctc                                                     19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gtaggattga caggattgga                                                    20

<210> SEQ ID NO 27
<211> LENGTH: 18
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 27
tcctccttgg ctgttatc                                                      18

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctgctggag ctgataagag aa                                                 22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gttcttttgt agggccttgg tc                                                 22

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acatcagtca gcagaaca                                                      18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttcctctagc ctctcact                                                      18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctgttattg ctgccatt                                                      18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 33
ttatcattcc gaactgtc                                              18

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tgatgtgaat gacctggaca cagaca                                     26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctcattgtt gtactggttg gatatg                                     26

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atatgaattc gccaccatgc accgcctgct ggcctgggac gca                  43

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcacctcgag tcaagtcccg aaacccggtg cgctgtg                         37

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cctgcagaaa gaggatgtg                                             19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 39
taatccgagg tgtaacggg                                            19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcaagggact gtcataggg                                            19

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcgatagata agcacacctc c                                         21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tattgaatcg gatcctgtag c                                         21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gtagacttga caggagaagc                                           20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
acaacaatac aggctattcc ag                                        22

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 45
ctatgcaaag gttctgaggt                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttgactactt tgccctagga                                                    20

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtttatctc tgtgatgtct cg                                                 22

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agaatcgcca actggtagtc                                                    20

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtccattcag actctgtacc a                                                  21

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ctcgcttcgg cagcaca                                                       17

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
```
aacgcttcac gaatttgcgt                                                        20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
acagcaacag ggtggtggac                                                        20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tttgagggtg cagcgaactt                                                        20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggagcgagat ccctccaaaa t                                                      21

<210> SEQ ID NO 55
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggctgttgtc atacttctca tgg                                                    23

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
catgcagaac ccacgacagt a                                                      21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cctcacgcag cttgttgtct a                                                      21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
caacaccaac atcgatgggc                                                        20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggtgatcaca cgttccacct                                                        20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggctgtattc ccctccatcg                                                        20

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccagttggta acaatgccat gt                                                     22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctttcaaggc ctgtctcctg                                                        20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
caacattcta gctgcacgga                                                        20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggccaagtgc caagtgatga                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agctatgcat cggcctttga                                                    20

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
ccgtccctct gcaggcctga c                                                  21

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aaacccattg agcactgagg agtcc                                              25

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gcactcacat cgctacatca                                                    20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 69
tcctaaagag ctggaggaga                                                    20

-continued

```
<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 70
ctgagatccc aatacaagct                                                     20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
gatgggactc ccttaaagac                                                     20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 72
agccgagcag aacaaggaac                                                     20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
tcctcctttt tggcaaaaga                                                     20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
tttcctcctt tttggcaaaa                                                     20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 75
gtacactttg cacgcaaagc                                                     20
```

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
ctgttctgag gatggagaga                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
ctgttctgag gatggagaga                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 78
gcacaagttt gtctccttaa                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 79
ggcataataa agcgtgccat                                              20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
gtgtcacaga tttttttcggg                                             20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 81
tggatgccta aaaaggtccg                                              20

<210> SEQ ID NO 82

```
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
cgctgctaaa tagtagctcg                                                          20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ttggattcaa ccctaagcta                                                          20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
tggatgccta aaaaggtccg                                                          20

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
gcatacttta ttagaggcca                                                          20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
ttggattcaa ccctaagcta                                                          20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
cctagcacag aacagtatct                                                          20

<210> SEQ ID NO 88
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
tcagtttcca tctatagctg                                            20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
atgcataggc cactcaatat                                            20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 90
cctagcacag aacagtatct                                            20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 91
tggttacata caacactgcc                                            20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 92
atgcataggc cactcaatat                                            20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 93
gtagttgtgg tgctttgtaa                                            20

<210> SEQ ID NO 94
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
      probe

<400> SEQUENCE: 94
atgcctttgc attaagttgg                                                 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
gattcttcaa tgagcaggga                                                 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 96
gtagttgtgg tgctttgtaa                                                 20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 97
ctcagttggc atcttacatg                                                 20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 98
aaaggcttag tgttggcttt                                                 20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 99
tgtgaggatc taggtttacc                                                 20

<210> SEQ ID NO 100
<211> LENGTH: 20
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 100
gaagagcaag gtgggcaatt                                            20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
caagctgatc tcaggtactt                                            20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 102
ctcagttggc atcttacatg                                            20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 103
accaaacact ctctcagact                                            20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 104
ctagaaggag ggtagtcagg                                            20

<210> SEQ ID NO 105
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 105
tagttgtggt ttccaagttc                                            20

<210> SEQ ID NO 106
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      probe

<400> SEQUENCE: 106
tgtgaggatc taggtttacc                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
caaagctggg actcagtaca                                                    20

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 108
caagctgatc tcaggtactt                                                    20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 109
acctctgtta acaaagtccg                                                    20

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 110
gggttaaagc agcgctttaa                                                    20

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 111
ctgagatccc aatacaagct                                                    20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued

```
    probe

<400> SEQUENCE: 112
accaaacact ctctcagact                                            20

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 113
agccgagcag aacaaggaac                                            20

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 114
tagttgtggt ttccaagttc                                            20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 115
tcctcctttt tggcaaaaga                                            20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 116
caaagctggg actcagtaca                                            20

<210> SEQ ID NO 117
<211> LENGTH: 18
<212> TYPE: RNA
<213> ORGANISM: Unknown
<220> FEATURE:
<223> OTHER INFORMATION: Description of Unknown:
    target sequence

<400> SEQUENCE: 117
ggccagccau auguagca                                              18

<210> SEQ ID NO 118
<211> LENGTH: 17
<212> TYPE: RNA
<213> ORGANISM: Artificial Sequence
<220> FEATURE:
<223> OTHER INFORMATION: Description of Artificial Sequence: Synthetic
    oligonucleotide
```

```
<400> SEQUENCE: 118
agcuacauug ccagcuc                                                    17

<210> SEQ ID NO 119
<211> LENGTH: 21
<212> TYPE: RNA
<213> ORGANISM: Unknown
<220> FEATURE:
<223> OTHER INFORMATION: Description of Unknown:
      target sequence

<400> SEQUENCE: 119
agcggccagc cauauguagc a                                               21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
agcuacaucu ggcuacuggg u                                               21

<210> SEQ ID NO 121
<211> LENGTH: 24
<212> TYPE: RNA
<213> ORGANISM: Unknown
<220> FEATURE:
<223> OTHER INFORMATION: Description of Unknown:
      target sequence

<400> SEQUENCE: 121
gagagcggcc agccauaugu agca                                            24

<210> SEQ ID NO 122
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
agcuacauug ucugcugggu uuc                                             23

<210> SEQ ID NO 123
<211> LENGTH: 21
<212> TYPE: RNA
<213> ORGANISM: Unknown
<220> FEATURE:
<223> OTHER INFORMATION: Description of Unknown:
      target sequence

<400> SEQUENCE: 123
cucuugagag cggccagcca u                                               21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 124
cuggcugggg aaaaugacug g                                              21

<210> SEQ ID NO 125
<211> LENGTH: 22
<212> TYPE: RNA
<213> ORGANISM: Unknown
<220> FEATURE:
<223> OTHER INFORMATION: Description of Unknown:
      target sequence

<400> SEQUENCE: 125
aaagaaaacu uccagaaauc cc                                             22

<210> SEQ ID NO 126
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
uggauuucuc ugugaaucac ua                                             22

<210> SEQ ID NO 127
<211> LENGTH: 22
<212> TYPE: RNA
<213> ORGANISM: Unknown
<220> FEATURE:
<223> OTHER INFORMATION: Description of Unknown:
      target sequence

<400> SEQUENCE: 127
aaagaaaacu uccagaaauc cc                                             22

<210> SEQ ID NO 128
<211> LENGTH: 24
<212> TYPE: RNA
<213> ORGANISM: Unknown
<220> FEATURE:
<223> OTHER INFORMATION: Description of Unknown:
      target sequence

<400> SEQUENCE: 128
gagagcggcc agccauaugu agca                                           24

<210> SEQ ID NO 129
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
uggauuucuc ugugaaucac ua                                             22

<210> SEQ ID NO 130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
```

```
agcuacauug ucugcugggu uuc                                        23

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
aaagaaaacu ucccagggct tc                                         22

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
gagggtggca gacacugctg ctaa                                       24
```

INHIBITION OF lncExACT1 TO TREAT HEART DISEASE

CLAIM OF PRIORITY

This application is a U.S. National Phase Application under 35 U.S.C. § 371 of International Patent Application No. PCT/US2021/043616, filed on Jul. 29, 2021, which claims the benefit of U.S. Patent Application Ser. No. 63/058,268, filed on Jul. 29, 2020. The entire contents of the foregoing are hereby incorporated by reference.

FEDERALLY SPONSORED RESEARCH OR DEVELOPMENT

This invention was made with Government support under Grant Nos. AG061034, HL122987, and HL135886 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 27, 2023, is named '29539_0419_US1_Sequence_Listing.txt' and is 36,814 bytes in size.

TECHNICAL FIELD

Described herein are compositions comprising an inhibitory nucleic acid targeting lncExACT1, and methods of use thereof to improve cardiac function in a subject in need thereof.

BACKGROUND

Heart failure (HF) is a growing cause of morbidity and mortality throughout the world.[1] Prognosis remains poor for many patients with HF[2] despite currently available treatments. Physical activity is associated with a lower risk of HF.[3] Although exercise training induces cardiac hypertrophy, in animal models it reduces the hypertrophy, dysfunction, and fibrosis seen in response to pathological stimuli.[4] Such observations suggest that although pathological and physiological hypertrophy appear superficially similar, they may reflect fundamentally different underlying mechanisms that exist in dynamic tension. This model is supported by distinct gene expression profiles, which diverge early and include sentinel differences in markers such as ANP, BNP, PGC1α, C/EBPβ and myosin heavy chain (MHC) isoform expression, often used to distinguish these states.[5-7] Another central distinction is that pathological hypertrophy often leads to HF, associated with death of cardiomyocytes through apoptosis and necrosis,[8, 9] which are not replaced due to the limited regenerative capacity of the adult heart.[10] In contrast, exercise protects against cardiomyocyte loss and is the only known physiological enhancer of cardiomyogenesis in the adult mammalian heart.[11] Identifying pathways capable of recapitulating these benefits of exercise with a feasible path to translation would have important clinical implications.

SUMMARY

In this study, by comparing lncRNA profiles in exercise-induced physiological hypertrophy and transverse aortic constriction (TAC)-induced pathological hypertrophy and HF, a novel set of cardiac long noncoding RNAs was identified that are dynamically regulated in response to exercise. These lncRNAs are referred to herein as lncEx-ACTs. LncExACT1 was downregulated in response to exercise and upregulated in pathological hypertrophy and HF. Overexpression of lncExACT1 is sufficient to induce pathological hypertrophy and HF while its inhibition recapitulates multiple exercise phenotypes, including physiological hypertrophy, markers of cardiomyogenesis, and protection against HF.

Thus provided herein are inhibitory nucleic acids targeting lncExACT1 (i.e., SEQ ID NO: 1) comprising 10 to 50 nucleotides, preferably comprising a region of at least 8, 9, 10, 11, 12, 13, 14, 15, 16, 17, 18, 19, 20, 21, 22 or more consecutive nucleotides that have at least 80% sequence complementarity to the lncExACT1, optionally wherein the region of complementarity includes up to 1, 2, 3, or 4 mismatches. The inhibitory nucleic acids target and inhibit expression or reduce levels of lncExACT1.

In some embodiments, the inhibitory nucleic acid is an antisense oligonucleotide.

In some embodiments, the inhibitory nucleic acid is a double-stranded ribonucleic acid (dsRNA), wherein said dsRNA comprises a sense strand and an antisense strand, the antisense strand comprising the region of complementarity to SEQ ID NO: 1. In some embodiments, the antisense strand comprises at least 15 contiguous nucleotides differing by no more than 3 nucleotides from SEQ ID NO:1. In some embodiments, the region of complementarity is at least 17 nucleotides in length. In some embodiments, the region of complementarity is between 19 and 21 nucleotides in length, e.g., is 19 nucleotides in length. In some embodiments, each strand is no more than 30 nucleotides in length. In some embodiments, at least one strand comprises a 3' overhang of at least 1 nucleotide. In some embodiments, at least one strand comprises a 3' overhang of at least 2 nucleotides.

In some embodiments, the inhibitory nucleic acids comprise at least one modification, e.g., a modified base or modified bond.

In some embodiments, the modified bases comprises one or more of a locked nucleotide, 2'-O-methyl modified nucleotide, a nucleotide comprising a 5'-phosphate group, a 2'-deoxy-2'-fluoro modified nucleotide, a 2'-deoxy-modified nucleotide, an abasic nucleotide, 2'-amino-modified nucleotide, 2'-alkyl-modified nucleotide, morpholino nucleotide, a phosphoramidate, and a non-natural base comprising nucleotide. In some embodiments, the inhibitory nucleic acid is a gapmer.

In some embodiments, the modified bonds comprise at least one phosphorothioate bond.

In some embodiments, the modification comprises conjugation of one or more lipids (optionally phospholipids or cholesterol) or aminosugars (optionally N-acetylgalactosamine (GalNAc)).

In some embodiments, the inhibitory nucleic acid comprises SEQ ID NO:5.

Also provided herein are compositions comprising an inhibitory nucleic acid as described herein (or a vector or cell as described herein), and a pharmaceutically acceptable carrier.

In some embodiments, the inhibitory nucleic acids are conjugated to or encapsulated within a lipid.

In some embodiments, the compositions comprise stable nucleic acid-lipid particle (SNALP) or XTC.

Also provided herein are vectors comprising a sequence encoding an inhibitory nucleic acid described herein.

In some embodiments, the sequence encoding the inhibitory nucleic acid is operably linked to one or more sequences for expression of inhibitory nucleic acid.

Further, provided herein are isolated cells comprising the vectors and optionally expressing the inhibitory nucleic acid.

Additionally provided herein are methods for reducing expression of lncExACT1 and/or Dachsous cadherin-related 2 (DCHS2) in a cell, e.g., a cell in a subject, the method comprising administering to the cell or subject a therapeutically effective amount of an inhibitory nucleic acid, composition, vector, or cell as described herein.

A method of improving cardiac function in a subject, the method comprising administering to the subject a therapeutically effective amount of an inhibitory nucleic acid, composition, vector, or cell as described herein. In some embodiments, the subject has pathological hypertrophy or heart failure, myocardial infarction (MI) or post-infarction remodeling, congenital or acquired cardiomyopathy; valvular heart disease and remodeling; and atrial and ventricular arrhythmias (optionally atrial fibrillation or ventricular tachycardia). In some embodiments, the methods result in an improvement in systolic function and/or diastolic function; reduced fibrosis; reduced cardiomyocyte cell death (apoptosis, necrosis); and/or increased cardiomyogenesis and regeneration.

Additionally provided are the inhibitory nucleic acids, compositions, vectors, and cells as described herein, for use in a method of improving cardiac function in a subject, optionally wherein the subject has pathological cardiac hypertrophy or heart failure; myocardial infarction (MI) or post-infarction remodeling; congenital or acquired cardiomyopathy; valvular heart disease and remodeling; or atrial and ventricular arrhythmias (optionally atrial fibrillation or ventricular tachycardia).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 6A-G. lncExACT1 regulates DCHS2 and Hippo signaling. A. DCHS2 gene expression in hearts from heart failure patients, mice with TAC-induced heart failure (HF), exercised (Run), AAV injection (AAV), or GapemR injection (Gap). B. Relative luciferase activity in NRVMs transfected with vectors carrying different regions of DCHS2 promoter with lncExACT1 lentivirus or LNA-GapmeR (KD). C. Gene expressions of ANP, BNP, β/αMHC ratio, PGC1α, and Cebpβ in NRVMs transfected with scramble control (Scramble) or DHCS2 siRNA (DHCS2 KD). D. Quantification of EdU and troponin positive cardiomyocytes in NRVMs transfected with scramble or DCHS2 siRNA. E. Quantification of cardiomyocytes area from NRVMs transfected with scramble or DCHS2 siRNA (DCHS2 KD). F. Gene expression of ANP, BNP, β/αMHC ratio, PGC1α, and Cebpβ in NRVMs transfected with lncExACT1 LNA-GapmeR (lncExACT1 KD) and/or DHCS2 overexpression (DCHS2 OE). G. Quantification of phosphorylation (p-Yap1) and total Yap1 (t-Yap1) in cytoplasmic (Cyto) and nuclear (Nu) in NRVMs with lncExACT1 knockdown and DCHS2 knockdown. *p<0.05, **P<0.01; in C, *p<0.05 vs. Control, #p<0.05 vs. lncExACT1 KD. Data are shown as mean±SEM.

FIGS. 8A-L. Establishment of physiological and pathological cardiac hypertrophy mouse models. A. Heart weight (HW) to tibial length (TL) ratio; B. Lung weight (LW) to TL ratio; C. Fractional shortening (FS); n=10 mice in Sed, and n=12 mice in Run in A-C. D. Relative mRNA expression of ANP, BNP, and β/αMHC ratio in sedentary (Sed) mice or mice subjected to voluntary wheel running (Run). n=5 mice per group. E. HW to TL ratio; F. LW to TL ratio; G. FS; n=9 mice in Sham, and n=10 mice in TAC-LVH in E-G. H. Relative mRNA expression of ANP, BNP, and β/αMHC ratio in mice subjected to sham or TAC for 2 weeks (TAC-LVH). n=5 mice per group. I. HW to TL ratio; J. LW to TL ratio; K. FS; n=6 mice per group in E-G. L. Relative mRNA expression of ANP, BNP, and β/αMHC ratio in mice subjected to TAC-induced heart failure (TAC-HF) or sham surgery. n=5 mice per group. *p<0.05, **p<0.01. Data are shown as mean±SEM.

FIGS. 9A-D. Characterization of lncExACT1. A. Genome alignment of mouse lncExACT1 to its homolog in different species in UCSC Browser. B. Relative lncExACT1 mRNA expression in different organs in mice. n=3 mice per group. C. Relative lncExACT1 expression in cardiomyocytes (CMs) and non-CMs isolated from mouse hearts. n=3 independent replicates per group. D. Relative expression of Beta-Actin (ACTB), U6, HOTAIR, and lncExACT1 RNA in cytosolic and nuclear fractions separated from CMs. n=3 independent replicates per group. *p<0.05 vs Heart. Data are shown as mean±SEM.

FIGS. 10A-E. Overexpression of lncExACT1 induces pathological hypertrophy in cardiomyocytes in vitro. A. Relative lncExACT1 expression in neonatal rat ventricular cardiomyocytes (NRVMs) infected with empty vector (Vector) or lncExACT1-overexpressing lentivirus (OE). B. Quantification of cardiomyocyte (CM) area for NRVMs stained with α-Actinin (red) and DAPI (blue). C. Relative mRNA expression of ANP, BNP, β/αMHC ratio, PGC1α, and C/EBPβ. D-E. Quantification of EdU-positive CMs and non-CMs. n=3 independent replicates per group. *p<0.05 vs Vector. Data are shown as mean±SEM.

FIGS. 12A-B. lncExACT1 binds to miR-222 in cardiomyocytes in vitro. A. List of miRNAs predicted to bind lncExACT1. Shown are SEQ ID NOs. 117-126. B. Representation of luciferase vector constructions. Shown are SEQ ID NOs. 127-132.

FIGS. 14A-E. lncExACT1 regulates Hippo pathway. A. Representative images and quantification of phosphorylated Yap1 (pYap) and total Yap (t-Yap) in hearts from sedentary mice (Sed), or mice subjected to voluntary wheel running (Run), sham surgery or TAC. n=6 mice per group B. Representative images and quantification of pYap and t-Yap in hearts from mice treated with LNA-GapmeR targeting lncExACT1 (GapmeR) or AAV9 overexpressing lncExACT1 (AAV). n=6 mice per group C. Representative images and quantification of pYap and t-Yap in hearts from mice with NRVMs with lncExACT1 OE or DCHS2 OE. n=4 independent replicates per group. D. Relative mRNA expression of Yap1 downstream targets (ETS1, MCM10, MYBL1, BUB1, CDCA8, and KLF23) in NVRMs with lncExACT1 KD and OE. E. Relative mRNA expression of Yap1 downstream targets in NVRMs with DCHS2 KD and OE. n=3 independent replicates per group in D-E. *p<0.05, **p<0.01 vs Control/Vector. Data are shown as mean±SEM.

DETAILED DESCRIPTION

Using an assay for genome-wide quantitative analysis of all known transcriptional components,[7] we previously demonstrated that the transcriptional pathways regulated in physiological and pathological hypertrophy were largely distinct, and the few transcription factors altered in both models mostly changed in opposite directions.[7] Moreover, pathways functionally important in the heart's response to exercise protect the heart against pathological stress with remarkable consistency.[7, 12] Interestingly, exercise was associated with activation of cell cycle pathways[13] and expression of transcription factors that promote cell cycle progression,[7] suggesting that exercise might enhance cardiomyogenesis in the adult heart to limit the pathological phenotype. Indeed, using multi-isotope imaging mass spectrometry (MIMS[14]), we demonstrated that eight weeks of voluntary wheel running increases birth of new cardiomyocytes in adult mice ~4.6-fold.[11] This exercise-induced cardiomyogenesis was completely blocked by inhibition of miR-222,[11] a miRNA that is necessary for exercise-induced cardiac growth and protects the heart against myocardial ischemia reperfusion injury.[12] These findings suggest that exercise enhances endogenous cardiomyogenesis in the adult heart and noncoding RNAs are essential for this response. Of note, however, miR-222 was not sufficient to induce physiological hypertrophy or other exercise-related phenotypes at baseline in vivo suggesting an important role for other pathways.[12]

Long noncoding RNAs (lncRNAs) are transcripts longer than 200 nucleotides that lack protein coding potential. LncRNAs have well-documented and important roles in cardiac development,[15, 16] pathological hypertrophy[7, 18] and HF.[19, 20] However, little is known about the role of lncRNAs in the cardiac effects of exercise including physiological hypertrophy, cardiomyogenesis, or protection against HF.

Figure 7:
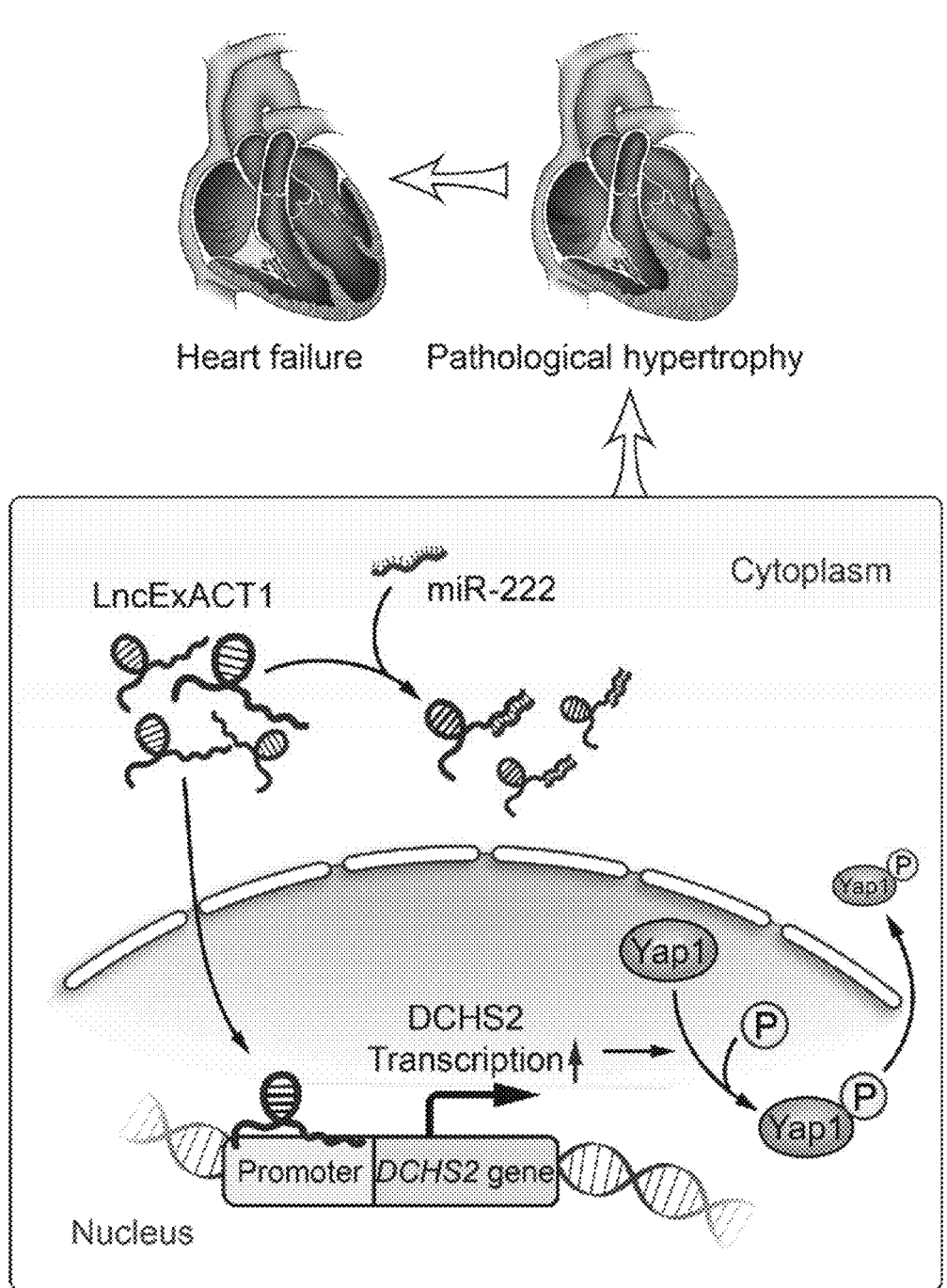
FIG. 7 Schematic of proposed signaling involved in lncExACT1 regulation of physiological and pathological hypertrophy. Under pathological conditions, lncExACT1 expression is increased. LncExACT1 binds miR-222 on the one hand, thereby releasing p27, and on the other hand binds to the DCHS2 promoter region and promotes DCHS2 transcription, which subsequently increases Yap1 phosphorylation and translocation to the cytoplasm. Over time, these signaling pathways eventually lead to pathological hypertrophy. In contrast, under physiological conditions, lncExACT1 expression is reduced, thereby releasing miR-222 and reducing DCHS2 transcription, which subsequently enhances Yap1 nuclear intention, resulting in physiological hypertrophy.
Figure 8D:
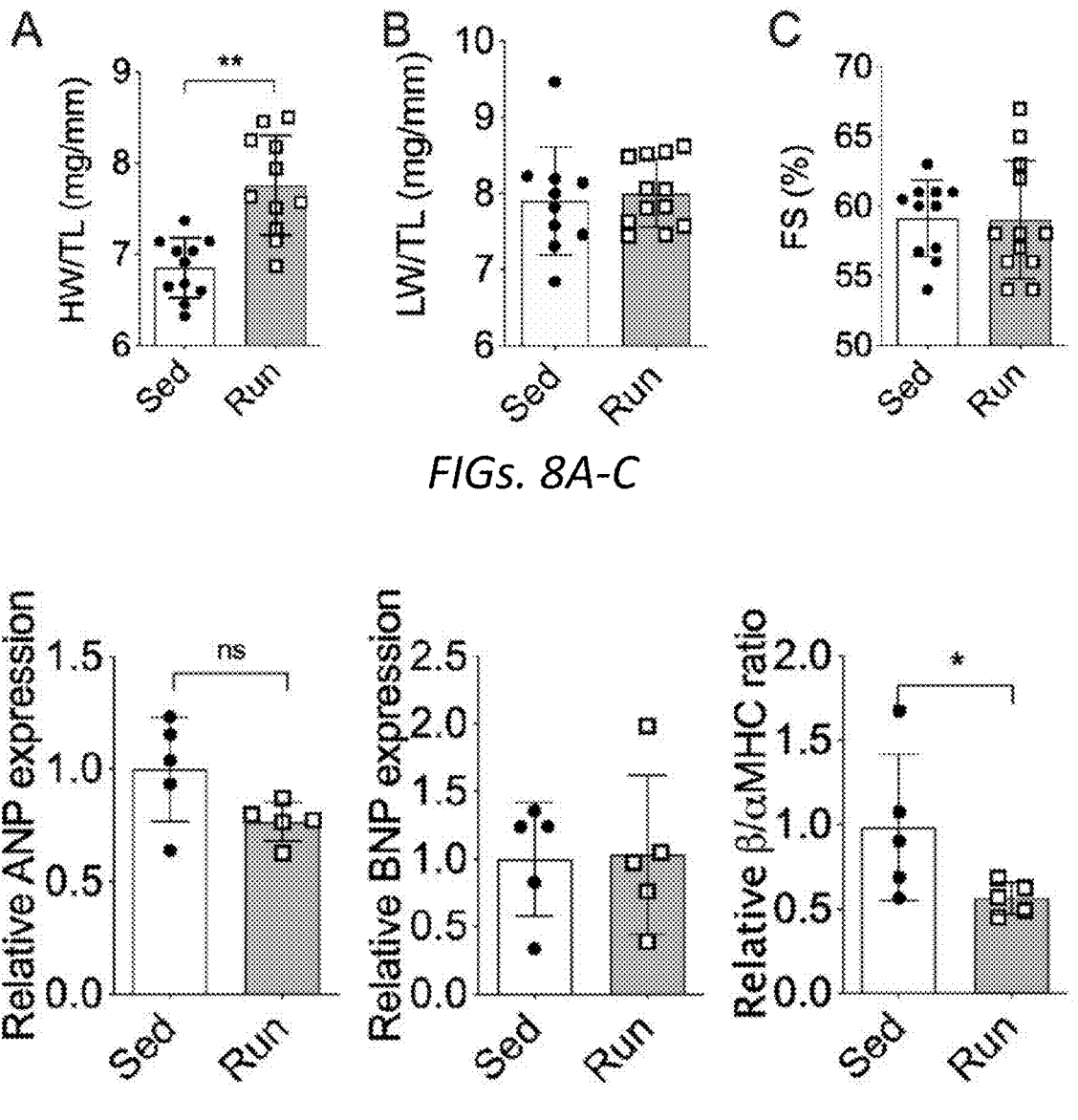
Figure 8H:
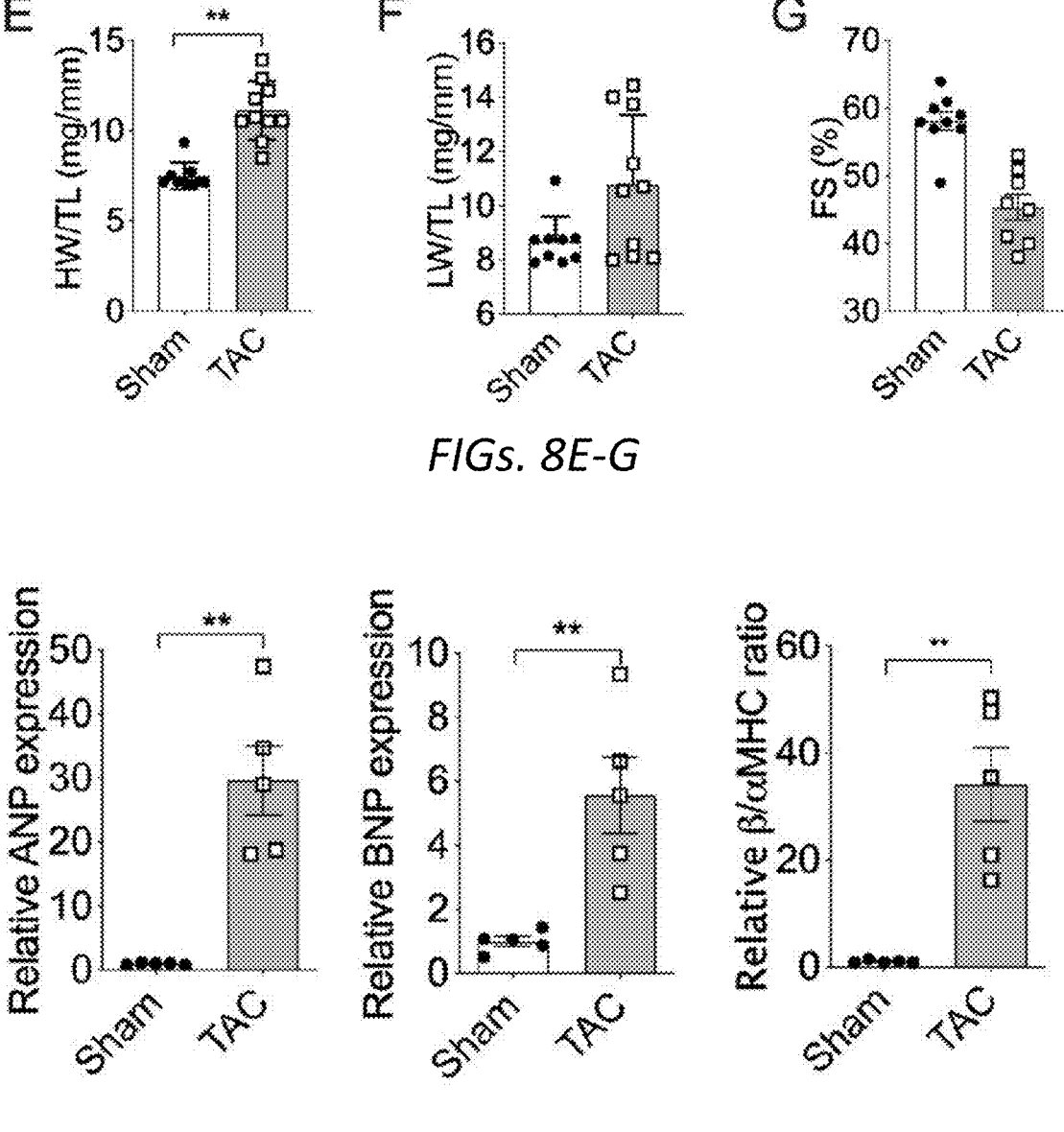
Figure 8L:
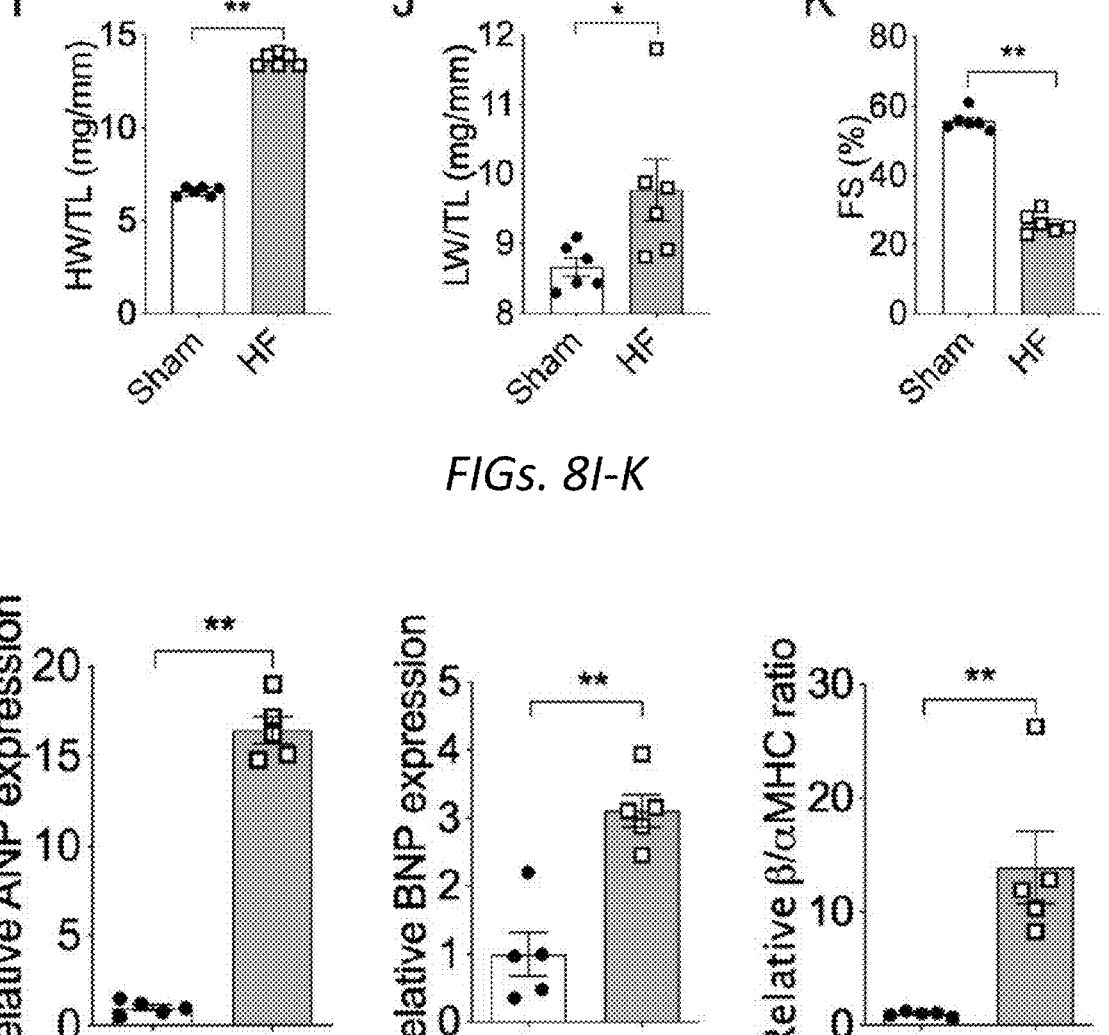

Understanding how exercise promotes cardiac health and whether the responsible mechanisms can be feasibly targeted has important fundamental and clinical implications. The data presented here demonstrate that cardiac lncRNAs are dynamically regulated by exercise and play an important role in determining the outcome of cardiac growth. A small number of exercise-regulated lncRNAs (lncExACTs) were also altered in pathological hypertrophy or HF. In every case, the change in exercise was opposite to that observed in the disease models, underscoring the distinct nature of these responses despite superficial similarities. lncExACT1 was sufficient to induce pathological hypertrophy and HF but also inhibited physiological cardiac growth. In fact, inhibition of lncExACT1 was sufficient to induce multiple exercise-related cardiac phenotypes including physiological hypertrophy, improved cardiac function, markers of cardiomyocyte proliferation, as well as protection against HF and fibrosis. LncExACT1 exerted its effects by binding and acting as a competitive endogenous RNA for miR-222 (previously found to be necessary but not sufficient for the cardiac exercise response),[12] and by modulating Hippo/Yap1 signaling through transcriptional regulation of its genomic neighbor DCHS2 (FIG. 7). These studies implicate Hippo/Yap1 signaling, one of the best documented regulators of cardiomyogenesis in the adult heart,[34] in the exercise response for the first time. Our findings provide new insight into lncRNA regulation of pathological and physiological hypertrophy and cardiomyocyte proliferation.

Pathological hypertrophy due to genetic or acquired causes is a common precursor to heart failure (HF).[40] However, cardiac hypertrophy can also develop as a physiological adaptation to exercise training. Although both forms of hypertrophy appear superficially similar, their outcomes are dramatically different, and accumulating evidence suggests distinct mechanisms underly pathological and physiological hypertrophy.[41, 42] Indeed, we previously demonstrated that transcription factors altered in physiological and pathological hypertrophy models are largely distinct, and when they change in both models they generally change in opposite directions.[7] In the current study, we extended this observation to lncRNAs. By comparing lncRNA profiles in exercise-induced physiological and TAC-induced pathological hypertrophy and HF, we identified a small number of lncRNAs, changed in both types of hypertrophy and in each case they changed in opposite directions in physiological and pathological hypertrophy. These observations not only support the concept that distinct pathways govern physiological and pathological hypertrophy, but also indicate that the early differences in underlying mechanisms may account for the divergent outcomes that occur later in these types of cardiac hypertrophy.

Cardiac lncRNAs have been implicated in cardiac development,[16, 43] pathological hypertrophy and HF.[18, 25, 44] However, virtually nothing is known about their roles in physiological hypertrophy. In the current study, we identified a class of lncRNAs (lncExACTs) that is dynamically regulated in exercise-induced physiological hypertrophy. Among these, we focused on lncExACT1, which is highly conserved and downregulated in exercised hearts but upregulated in TAC-induced pathological hypertrophy and HF. Interestingly, in mice and in primary cardiomyocytes, we demonstrated that overexpression of lncExACT1 induces pathological hypertrophy while its inhibition induces physiological hypertrophy, indicating that lncExACT1 functions as a switch between physiological and pathological hypertrophy. Our work and that of others have shown that the pathways functionally important in the heart's response to exercise protect the heart against pathological stress with remarkable consistency.[7, 12] Consistent with this, we found that inhibition of lncExACT1 protected against TAC-induced pathological hypertrophy, fibrosis, and cardiac dysfunction. In addition, we found that lncExACT1 was increased in hearts and plasma from HF patients compared to non-HF patients. These findings underscore the potential clinical relevance of lncExACT1 and suggest further study of its value as a therapeutic target and/or biomarker is warranted.

Exercise is associated with transcription factors[7, 13] and miRNAs[12] that promote cell cycle progression. Previously, using multi-isotope imaging mass spectrometry (MIMS[14]), we demonstrated that eight weeks of voluntary wheel running increased birth of new cardiomyocytes ~4.6-fold in adult mice.[11] This exercise-induced cardiomyogenesis was completely blocked by inhibition of miR-222,[11] a miRNA that also necessary for exercise-induced cardiomyocyte hypertrophy.[12] In the current study, we found that inhibition of lncExACT1 induced markers of cardiomyocyte proliferation, suggesting that inhibition of lncExACT1 is sufficient to mimic the pro-proliferative effects of exercise. Interestingly, we found that lncExACT1 acts by binding miR-222. Whether lncExACT1 inhibition results in durable cardiomyogenesis—as seen in exercise[11]—and how this contributes to its functional benefits merit further investigation.

Of note, although our prior work had suggested a necessary role for miR-222 for exercise-induced cardiac growth, cardiac-specific overexpression of miR-222, at baseline, was not sufficient to induce physiological hypertrophy,[12] suggesting that the effects of lncExACT1 inhibition, may not be mediated solely by miR-222. Indeed, we found that lncExACT1 conferred its effects in cardiomyocytes by promoting DCHS2 and thereby enhancing the nuclear retention of Yap1, the core regulator of the Hippo pathway. It has been suggested that DCHS2 works with FAT as ligand-receptor system in regulating cell proliferation via the Hippo signaling pathway in *Drosophila*.[45, 46] However, the role of DCHS2 in regulating Hippo pathway signaling in mammals has not been examined. Moreover, the role of DCHS2 in the heart is entirely unknown. In the current study, we found that in cardiomyocytes, knockdown of DCHS2 promoted Yap1 nuclear retention while overexpression of DCHS2 reduced Yap1 nuclear retention but increased Yap1 phosphorylation in the cytoplasm, indicating that DCHS2 regulates Yap1 in cardiomyocytes. Similar changes were also found in cardiomyocytes when we manipulated lncExACT1. These findings suggest that DCHS2 likely contributes to the effects of lncExACT1 through modulation of Yap1 transcriptional activity. These studies also implicate Hippo/Yap1 signaling, one of the best documented regulators of cardiomyogenesis in the adult heart,[34] in the exercise response for the first time.

In conclusion, we have demonstrated that lncExACT1 was sufficient to induce pathological hypertrophy and HF but also inhibited physiological cardiac growth. Without wishing to be bound by theory, it is believed that lncExACT1 mediates its effects in cardiomyocytes by acting as a ceRNA for miR-222 and by driving DCHS2-mediated Yap1 deactivation (FIG. 7). Since RNA-directed antisense strategies similar to the GapmeR employed here have proven feasible clinically,[26] these studies suggest lncExACT1 merits consideration as a tractable therapeutic target in HF and other related cardiac diseases.

Methods of Treatment

Provided herein are methods of treating subjects to improve cardiac function. In some embodiments, the methods are used for treating subjects who have or are at risk of developing impaired cardiac function, e.g., due to pathological hypertrophy or heart failure, myocardial infarction (MI) or post-infarction remodeling, or congenital or acquired (e.g., drug- or chemotherapy-induced) cardiomyopathy, valvular heart disease and the remodeling caused by valvular heart disease, or atrial and ventricular arrhythmias such as atrial fibrillation or ventricular tachycardia. Generally, the methods include administering a therapeutically effective amount of a treatment as described herein, e.g., comprising administering an inhibitory nucleic acid targeting lncExACT1 as described herein, to a subject who is in need of, or who has been determined to be in need of, such treatment.

As used in this context, to "ctreat" means to ameliorate at least one symptom of the disorder associated with impaired cardiac function. Administration of a therapeutically effective amount of a composition described herein comprising an inhibitory nucleic acid targeting lncExACT1 for the treatment of a condition associated with impaired cardiac function will result in improved cardiac function and a decrease or improvement in one or more symptoms or clinical signs of the condition. The present methods can also be used for prophylaxis in subjects at risk of developing impaired cardiac function, i.e., to reduce risk or delay development of impaired cardiac function. Administration of a prophylactically effective amount of a composition described herein comprising an inhibitory nucleic acid targeting lncExACT1 for the treatment of a condition associated with impaired cardiac function will result in reduce risk or delay development of impaired cardiac function and can also produce a decrease or improvement in one or more symptoms or clinical signs of the condition.

In some embodiments, the subjects treated using a method described herein have pathological cardiac hypertrophy, e.g., associated with hypertension and heart valve stenosis. Symptoms can include dyspnea, syncope, palpitations, angina, orthopnea, paroxysmal nocturnal dyspnea, or dizziness. Thus in a subject who has pathological cardiac hypertrophy a treatment as described herein can result in an improvement of one or more of the symptoms or clinical signs described above. In addition, as pathological cardiac hypertrophy can develop into heart failure, the present methods can reduce risk of developing heart failure, as well as reducing risk of MI and sudden cardiac death.

In some embodiments, the subjects have heart failure with reduced ejection fraction (HFrEF, with an EF≤40%) or heart failure with preserved ejection fraction (HFpEF, typically with an EF≥50%). See, e.g., Chen et al., Cells. 2019 December; 8(12):1651. Symptoms and clinical signs of heart failure can include one or more of Exertional dyspnea and/or dyspnea at rest and/or Paroxysmal nocturnal dyspnea (PND); Orthopnea; Acute pulmonary edema; Chest pain/pressure and palpitations; Tachycardia; Fatigue and weakness; Nocturia and oliguria; Anorexia, weight loss, nausea; Exophthalmos and/or visible pulsation of eyes; Distention of neck veins; Weak, rapid, and thready pulse; Rales, wheezing; $S_3$ gallop and/or pulsus alternans; Increased intensity of P2 heart sound; Hepatojugular reflux; Ascites, hepatomegaly, and/or anasarca; or Central or peripheral cyanosis or pallor; see, e.g., Dumitru, "Heart Failure," available at emedicine.medscape.com/article/163062-overview; Updated: May 7, 2018). Heart failure can be diagnosed using the Framingham criteria (see, e.g., Ho et al., J Am Coll Cardiol. 1993; 22(4 Suppl A):6A-13A). In some embodiments, the subjects have heart failure characterized using the New York Heart Association (NYHA) classification system I, II, III, or IV; or American College of Cardiology/American Heart Association (ACC/AHA) staging system stage A, B, C, or D (see, e.g., Yancy et al., Circulation. 2013 Oct. 15. 128(16):e240-327). Thus in a subject who has heart failure a treatment as described herein can result in an improvement of one or more of the symptoms or clinical signs described above, as well as reducing risk of MI and sudden cardiac death.

In some embodiments, the methods are used treat subjects who have or are at risk of developing valvular heart disease and the remodeling caused by valvular heart disease, or atrial and ventricular arrhythmias such as atrial fibrillation or ventricular tachycardia. As shown herein, the present methods reduce fibrosis, which is a contributor to many arrhythmias.

In some embodiments, the methods described herein improve one or more of systolic function or diastolic function; reduce cardiac fibrosis; reduce cardiomyocyte cell death (e.g., via apoptosis or necrosis); and/or increase cardiomyogenesis and regeneration.

In some embodiments, the methods can be used in subjects who are not considered at high enough risk to warrant intervention, e.g., subjects who have apparently normal cardiac function, or subjects who have had a recent (e.g., within the previous 40 or 90 days) cardiac event such as a myocardial infarction (MI), have undergone a recent (e.g., within the previous 40 or 90 days) revascularization procedure (e.g., stent or bypass surgery), who have a left ventricular ejection fraction (LVEF) of greater than 30-35%, and/or who have symptoms and/or a diagnosis of pathologic cardiac hypertrophy or early stages of heart failure. In some embodiments, subjects who can be treated include those who are at high risk of developing heart failure, e.g., who have 1, 2, 3, or more risk factors, e.g., presence of type 2 diabetes, obesity (BIH≥30), older age (e.g., 65 years of age or older), female gender, hypertension, family history of heart disease, or coronary artery disease. In some embodiments, subjects who can be treated include those who are sedentary, or who are unable to exercise.

In some embodiments, the methods can be used in subjects who typically would be considered at high risk, e.g., subjects who have a LVEF of 30-35% or less, and symptoms and/or a diagnosis of heart failure.

The present methods can be used, e.g., in mammalian subjects, e.g., in human and non-human veterinary subjects, e.g., cats, dogs, horses, pigs, cows, goats, and sheep. As one of skill in the art would appreciate, sequences appropriate for other species might be used when the subject is a non-human mammal. One of skill in the art could readily identify sequences for other species.

Inhibitory Nucleic Acids

The present methods and compositions include the use of inhibitory nucleic acids targeting the lncRNA lncExACT1. Exemplary sequences of sequences encoding human and mouse lncExACT1 are shown below. Please note sequence is shown for the cDNA clones; the RNA sequence is identical except that U (uracil) would replace each T (thymine).

Human lncExACT1 lncRNA:
(SEQ ID NO: 1)
GCGACTCCTGCTCCGACCCAGCCTCCGCCGCCTGCCTTCCCCTCCCTGC

CGTGTGATGCGGCGCACACGAGGGCAAACTCCAACCTGCGAGCCGCGCT

CTGCAGCAGGGCGGAAGAGGAGCAAATGCAAAAGCACTGGGAGACGTGC

-continued
ACCGCGGGGCGGGTGGGGGACGCGCAGGCGGGGCGTCTGCCTGGGCTTG

GCCAAGTGCCAAGTGATGATGGGTGCGGGGAGGTGAGAGGAGCGGCCTC

TCCGCGGCCTCCCCCTCCATCCGCTTGACCGTCCCTCTGCAGGCCTGAC

TCTTGGCTCGCGCTGAGCCAAGAGGGTAGAGGTTATCATCACTTTGGGG

TGCCAAACTTGTGTTCTCCATTTGGCGAGAGGGACTCCCGTCCGCAGCG

GAAGGACAGATGGAGTCAAAGGCCGATGCATAGCTGGGGCCAGGATGGC

TTTAAAGGGGAGAAGGCGGAACTTGGAAAAGCCTTCCAGAAAACCCGAG

AAATCTGTGGCACACATGGTGCAAACCACACTTTATTATGCGTGCTACT

ACCCAGCGACGTGTGAGCCTCTTGTCACTCCCCTCTGCCACCAGGAATG

ACGACAATATATCCGCCCTGAGAACCCTTTTTCTACATTCAGCGCCATC

ATAACACTTCCAGGATGTCTGACGATGCTGACTGATGAGCAGAAAGCCC

TGGTGGCTGACACCCCGCAAGCCCTCAGCGCTCCCCCACCACCCCTAGG

CAAGGAAGTGTGCAAGCGGGATAACTCTACGGATACCACTTTCAAAACT

AGCTTCTGTCTGAGCCGAACGCAAATGCCAATAAATAGCCATAGTCGCA

GATTTCCCTTCAATTAACTATAATAATCGGTAGAAACTGATCAATGGCC

TCTAATAAAGTACGCCTGAGAAAAGACTCTCTGGACTCTTAAAAATGGC

TGACCATATTTAGCAAGTGGTTTCTGCAATTTTGCATTTGGGCCTGAGA

GAAGAATTAATTTCCTAGATACCGTTTCTCTCCTTTAGGGAGGACCAAA

AGCCCTGCATAGTGGTTTCTTGCAGCAACAACAAAATGCCTTTTTAAAT

GTGCAACGGAGGTGTATGTAATTGCTAATCCACAGCCACACCGTTATCT

CTACCTGTGACCAAATAACAATAAAATAATTGACTTTGTAGCATATATG

TTACCGAAAATGGGGACATTATTAAAATAAATTCAGCTTTCTTTCCCCC

AATGAACTCTCTTTAACCATTAAAGAGATTTGTTA

Mouse lncExACT1:
(SEQ ID NO: 2)
CTCTGGGTCACCGTCGGCATCGGACACTGAGACTCGAGCCACGTAGTCGC

CTGGGTGGGCGCCCTCAGAGACCTGGACCGCACCTCCCTCGGTGAGGAAG

AGCAGGTGGATGGCAGGAGGGTTGTCATTCACGTCCAGCACGTCAATGGA

CACGCGCACGGTGGCTACCTCTGGCTCGGCGCCCCCGTCGCGGGCCTGGA

CCACCAACTGGTGCCAGGCCTGCTCCTCCCGGTCTAAAGGTCTTTGCACC

CGCACTACGCCGCTCAGCTCCTCCACAGAAAAATAACCCGGATCGCCCAG

TGGCCCACCACCTGCGCTCGCCACGGGCACTTGCCGCTCCCGGATACTGT

AGCGTACCAAGCCATTGGGGCCCAAGTCGCGATCAGTAGCACGCACGCGA

CAAACCTCAGAGCCCGGCTGGGCGTCCTCACGTACTGTGGCGCGGTACTC

GCCCTGCTCGAAAACTGGCGGGTTGTCGTTCTCATCCAACACACGCAGCT

GCACGTGCAGGAGGCCGGTGCGCCGAGGGCTGCCACCGTCCCAAGCTTCA

ATGTGCAGCTCGTCGCGCTGCCGCCGCCTCTCGGTCCAAGCGCCGCAGCAG

CACCAAGTCTAAGGGTTCCAGCGGTGATGAGGACACCGGCAGGGAAGGCG

ACGCCGGTAACCCCGGCGTCCCATAGCGCAATTGGAAGAAGGGTCCTGTG

GGATCCTGGGGCATGTCAGAAGCTTGCAGCAAAGTGTAGCCCTGGATGCT

GAACAGTCCCGCGTCCGGGTCCTGGGCTCCTGGCAGGCGGAACGCTGTCC

CGGGCGGGCTGAGTTCGGACACGTCCAGCTGCAGGGAGTCGCGGGGAAAG

-continued

CGAGGGGAATGGTCGTTCACGTCGTTGACGCGGATCTCCACCTGTACCAC

CTCTCCCAACAGCGTGGCGGCCACGAAGCTATAGTGGTCCTGTCGCTCGC

GGTCCAGACGCCGAGCGGTGCGGATGATACCAGTGTCCGGGTGCACGTGG

AAGTCGTCCAGCAGCGGGGAGTCATCCGAGTCCTCCGAAAGAAAAAAGCC

ATTCCCATCCTGTTGCTGAGCTGCTGGCAACCCCGCGCGAATGTCACCCA

CCAGTGTGTCTGGGGGCAGCCCCTCGTCCACCGAGAGGCTGAGGTTGAAC

ACCTGGGCAGATGAGCCCGAGGCTGCCCACAGCCAGGCGTGGACGAAAAG

CCGGAGCAGGGAGCTCTGCGCCCCGGCGCCGCGGGGCCGCCCACGGGGTG

ACCCAGCCGGCTGACGCCCTTCACCCATCCTTCGCCCAGCAGGGCTCATT

TCTCCTCCAGCTCTTTAGGAAGAAGGCTCCGGCTAGCTGCCAGCTTGTAT

TGGGATCTCAGAGCAACCCAGGAGCCTCTTCAGTATTAAGCCAGGGAAGA

AAAGACTTTGGCAAACAAACGAAAAGACCCGGGAGTTCCCAAGGTGGCAT

CTGCAACTGGTGCAGACGTCCTCTGGCCGCAGCTCACGCAGGCGGGGGCG

GCTCTAGCTGCCTCTGCCTCCGCGGCCACCTCTCCAGCCTCTGGATGTCT

TTAAGGGAGTCCCATCGCTTTTTCTCTCTTCTTCTATTCCTTTTACATCT

GTTCCTTGTTCTGCTCGGCTGGCTGTTTCCCCCTGGTAAAGTCAGGTGCA

TTATTTCTTTTGCCAAAAAGGAGGAAATTATTTAAAGCGCGCACACGGAG

AGGAAGGGGATCCGGCCGGGAAGGGGGTGGAGAAAGGGCGGGGAGGCCGA

GGGGGCGCGGGGCGGGAGGAACGGTGGGAGGGGCCGCTCGGGCAGCAGAC

TGCTACAGGGGCGGCCGCTCCCCCACCCACCCCACTCCACCTCCCGCGTC

TCCCGGCGCTGGGGACTCCGTGGAGCCCCCTCTGACTGGGCCTCCTACTC

CTTAGTCCCCTCCCCGTGCGTGATGCGGCTCGCACCGGGATGAATTCCAA

CCTGCGAGCCTCGGTTCTGTAGAAGGACTAAAAAACGGCTAGCCGGATGG

ACACGCAGCCCCAGACAGTGACGCTGATGGGGTTGTCTGGCTTGGCTTTG

CGTGCAAAGTGTACTGGGTTAGGGAAGAGGCCAGTAGCTTGCCCCTAAGC

TCGCTCTCTCCATCCTCAGAACAGCCCCTGCAGCGAGCCTGCCCATGGCT

CCATGTAAGGTGGGGGTTATATGGTCACTTTAAGGAGACAAACTTGTGCT

CTCTATTTGGCGAGAGAACCCCACCTCCTCAGCGGAAGGACAGATGGAGT

CAAAAGGAGATGCACAGCTGGGGCCAGTTTGACTGTAAAGCAGGGAAGGC

GGAACTTGGAGAAAAAAAAAGAAGAAGAAGAAAGGAGAAAGAAAACTTC

CAGAAATCCCGAAAAAATCTGTGACACACATGGCACGCTTTATTATGCCG

AGCTACTATTTAGCAGCGTGCTAGTGTCTTGTCACTCCCCTCTGCCACCT

GTGATGACAACAATGGATGGAGCTTGCGGACCTTTTTAGGCATCCAGCGC

CATCATACCTGCCAGCATATTTTATGATGATGATTTATGTGCGGATTGAC

CTTGTGGCATAAGCCCCAGCACACGGCTTTACCTCCAGCCCTATGAGAAG

AACCTTGCAGGGATCTGATAGCTCTTCCAAAGTAGCTTAGGGTTGAATCC

AAAGACAATTCACCTCAGCCTGTGTAGTCTCGGGCTTCTCTCCTGCTATC

CACAGCTATAGATGGAAACTGACAAATGGCCTCTAATAAAGTATGCTCCA

CCAGAGGAGTCTGCTCTCTTGAGAGCGGCCAGCCATATGTAGCAAAAGGT

TTCTGCAATTTTGCATTTCAGCCAGAAGGAAGAATTAATTTCCTAGATAC

-continued

TGTTCTGTGCTAGGGGGAGACCAAAAGGCCAGCATACAGTTCCCCAGAAA

CCCCAGTGAAACGCCTTCTTATATTGAGTGGCCTATGCATGCCATTGCTA

ATTAGCAGCCACACCAACCTGTACCCCTGAAAAAATAATAATCAAATGAT

TTTCTTGGCAGTGTTGTATGTAACCAGAGATGCTATTAAAATAATGTCAG

CCTCCCTTTTATCGATCAAGTGCCTTTAAGCATTTGGGAGATCAGGCTTG

AGCCTTTGGAGTCTTCTTTCCAACTTAATGCAAAGGCATCAGGAGTCTTA

CAAAGCACCACAACTACTGCCACCACTGGTCCCTTCTGAGGTGGTTCTCC

ACCAAGCATTCAGACTGTTTCTAAAGCCAACACTAAGCCTTTAACCCCTA

TTCAGAACCTACATGATAGCTTCTTGTTTCAGACTCCTTCCTAAATTGCC

CACCTTGCTCTTCTTCCCTGCTCATTGAAGAATCTTTGAGTTGTTGAGCT

TCCCTGTCTAGATCTCTTTTTGCCCCCCCCCCCAAACAGGCTCCTTCTCC

TTCAGGTCTCATGTAAGATGCCAACTGAGGGGACATCTCCCTGACTACCC

TCCTTCTAGTGGGAGGGTAAACCTAGATCCTCACATTCTATTTCATTCAA

AGTGCCTTTAAGTACCTGAGATCAGCTTGTTTGGTTCATCTGCTTGGTCT

ATTACTCCAATCTTACCCTCTTCATAGACTTAAAGCGCTGCTTTAACCCA

CTCCCCATGAGAGAGTCTGAGAGAGTGTTTGGTGAATAGTAGATCACTCT

TCACTGTATGTATCCAGTGGCTGGAATAACTGATAGGCAGATAAATGGAT

GAACTTTTAAACTGGAACTTGGAAACCACAACTAAAGAGTAACTGGCCCT

GAGGTCCTTCACTGTACTGAGTCCCAGCTTTGCCTTGCTGGTTTTACTCA

TCCTGTGAATCTCCTTTGAACCTTTTCAGCTTATGTGAAACTATCATCGT

CCAATATTTCCTTGGCACTAAGAGAAAAAGCGGATCTTCTTCCTGCACAT

GGCACTGACACGGACTTTGTTAACAGAGGTTTAGTTTTGAACAAATGGGA

AAATAAAGCTTTGGAAACCTG

Inhibitory nucleic acids useful in the present methods and compositions include antisense oligonucleotides, ribozymes, siRNA compounds, single- or double-stranded RNA interference (RNAi) compounds such as siRNA compounds, modified bases/locked nucleic acids (LNAs), peptide nucleic acids (PNAs), and other oligomeric compounds or oligonucleotide mimetics that hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112. In some embodiments, the inhibitory nucleic acids bind to and reduce levels of the target RNA.

In some embodiments, the inhibitory nucleic acids are 10 to 50, 10 to 20, 10 to 25, 13 to 50, or 13 to 30 nucleotides in length. One having ordinary skill in the art will appreciate that this embodies inhibitory nucleic acids having complementary portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the inhibitory nucleic acids are 15 nucleotides in length. In some embodiments, the inhibitory nucleic acids are 12 or 13 to 20, 25, or 30 nucleotides in length. One having ordinary skill in the art will appreciate that this embodies inhibitory nucleic acids having complementary portions of 12, 13, 14, 15, 16, 17, 18, 19, 20, 21, 22, 23, 24, 25, 26, 27, 28, 29 or 30 nucleotides in length, or any range therewithin (complementary portions refers to those portions of the inhibitory nucleic acids that are complementary to the target sequence).

The inhibitory nucleic acids useful in the present methods are sufficiently complementary to the target RNA, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a RNA, then the bases are considered to be complementary to each other at that position. 100% complementarity is not required.

Routine methods can be used to design an inhibitory nucleic acid that binds to the target sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, "gene walk" methods can be used to optimize the inhibitory activity of the nucleic acid; for example, a series of oligonucleotides of 10-30 nucleotides spanning the length of a target RNA can be prepared, followed by testing for activity. Optionally, gaps, e.g., of 5-10 nucleotides or more, can be left between the target sequences to reduce the number of oligonucleotides synthesized and tested. GC content is preferably between about 30-60%. Contiguous runs of three or more Gs or Cs should be avoided where possible (for example, it may not be possible with very short (e.g., about 9-10 nt) oligonucleotides).

In some embodiments, the inhibitory nucleic acid molecules can be designed to target a specific region of the lncRNA sequence. For example, a specific functional region can be targeted, e.g., a region comprising a known RNA localization motif (i.e., a region complementary to the target nucleic acid on which the lncRNA acts). Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

Once one or more target regions, segments or sites have been identified, e.g., within a target sequence known in the art or provided herein, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this disclosure, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a RNA molecule, then the inhibitory nucleic acid and the RNA are considered to be complementary to each other at that position. The inhibitory nucleic acids and the RNA are complementary to each other when a sufficient number of corresponding positions in each molecule are occupied by nucleotides which can hydrogen bond with each other. Thus, "specifically hybridisable" and "complementary" are terms which are used to indicate a sufficient degree of complementarity or precise pairing such that stable and specific binding occurs between the inhibitory nucleic acid and the RNA target. For example, if a base at one position of an inhibitory nucleic acid is capable of hydrogen bonding with a base at the corresponding position of a RNA, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target RNA molecule interferes with the normal function of the target RNA to cause a loss of activity, and there is a sufficient degree of complementarity to avoid non-specific binding of the sequence to non-target RNA sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an RNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Inhibitory nucleic acids that hybridize to an RNA can be identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an RNA. Thus, oligonucleotides are chosen that are sufficiently complementary to the target, i.e., that hybridize sufficiently well and with sufficient specificity, to give the desired effect.

siRNA/shRNA

In some embodiments, the nucleic acid sequence that is complementary to a target RNA can be an interfering RNA, including but not limited to a small interfering RNA ("siRNA") or a small hairpin RNA ("shRNA"). Methods for designing and constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. For example, the siRNA can include one or more glycol nucleic acids (GNAs), e.g., in the seed sequence (residues 2-8 of a 21-23 base long dsRNA). In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific RNA targets within the background of cellular RNA. Such a cleavage event renders the RNA non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Modified Inhibitory Nucleic Acids

In some embodiments, the inhibitory nucleic acids used in the methods described herein are modified, e.g., comprise one or more modifications described herein, e.g., comprise modified bonds or bases. A number of modified bases include phosphorothioate, methylphosphonate, peptide nucleic acids, or locked nucleic acid (LNA) molecules. Some inhibitory nucleic acids are fully modified, while others are chimeric and contain two or more chemically distinct regions, each made up of at least one nucleotide. These inhibitory nucleic acids typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270:1628-1644, 2003; Fluiter et al., Mol Biosyst. 5(8):838-43, 2009; Hagedorn et al., Nucleic Acids Res. 2017 Mar. 17; 45(5): 2262-2282; Papargyri et al., Mol Ther Nucleic Acids. 2020 Mar. 6; 19: 706-717). In some embodiments, a gapmer is 14-20, e.g., 15-18, e.g., 15-16 nucleotides long and is enriched with LNA in the flanking regions and has 7-8 nts of DNA in an LNA-free central gap, e.g., a 16-mer with 7-8 DNA in the middle with LNAs on either end. In some embodiments, the oligonucleotide is a mixmer (includes alternating short stretches of LNA and DNA; Naguibneva et al., Biomed Pharmacother. 2006 November; 60(9):633-8; Orom et al., Gene. 2006 May 10; 372( ):137-41). Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl (2'OMe) modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N ($CH_3$)—$CH_2$, $CH_2$—N($CH_3$)—N($CH_3$)—$CH_2$ and O—N ($CH_3$)—$CH_2$—$CH_2$ backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050. See also U.S. Pat. No. 8,314,227 (Unlocked Nucleobase Analog (UNA)-containing siRNA (UsiRNA)); U.S. Pat. No. 7,371,404 (SAMR-TICLES®); U.S. Pat. Nos. 8,501,824, and 7,959,505 (DiLA2 (Histidine-containing Di-alkylated Amino Acid)).

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, $SCH_3$, F, OCN, $OCH_3OCH_3$, $OCH_3O(CH_2)n\ CH_3$, $O(CH_2)n\ NH_2$ or $O(CH_2)n\ CH_3$ where n is from 1 to about 10; Ci to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al, Helv. Chim. Acta, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide. For example, the inhibitory nucleic acid can include, e.g., five 2'-O-methoxyethyl-modified ribonucleotides at each terminus, a central region of ten 2'-deoxynucleotide residues, a full phosphorothioate modified backbone, and all cytosine residues methylated at position 5 (New Engl. J. Med. 379, 22-31, 2018).

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methyl-cytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothy-mine and 2-thiocytosine, 5-halouracil and cytosine, 5-pro-pynyl uracil and cytosine, 6-azo uracil, cytosine and thy-mine, 5-uracil (pseudo-uracil), 4-thiouracil, 8-halo, 8-amino, 8-thiol, 8-thioalkyl, 8-hydroxyl and other 8-sub-stituted adenines and guanines, 5-halo particularly 5-bromo, 5-trifluoromethyl and other 5-substituted uracils and cyto-sines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclope-dia of Polymer Science And Engineering', pages 858-859, Kroschwitz, J. I., ed. John Wiley & Sons, 1990, those disclosed by Englisch et al., Angewandle Chemie, Interna-tional Edition', 1991, 30, page 613, and those disclosed by Sanghvi, Y. S., Chapter 15, Antisense Research and Appli-cations', pages 289-302, Crooke, S. T. and Lebleu, B. ea., CRC Press, 1993. Certain of these nucleobases are particu-larly useful for increasing the binding affinity of the oligo-meric compounds of the invention. These include 5-substi-tuted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applica-tions', CRC Press, Boca Raton, 1993, pp. 276-278) and are presently preferred base substitutions, even more particu-larly when combined with 2'-O-methoxyethyl sugar modi-fications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by refer-ence. In some embodiments, the inhibitory nucleic acids can include one or more 2'-deoxythymidine overhangs, e.g., 2'-deoxythymidine dinucleotide overhangs at the 3' ends.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glyc-ero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). One example is encapsulation in cationic amino MC3 lipid nanoparticle comprising (6Z,9Z, 28Z,31Z)-heptatriaconta-6,9,28,31-tetraen-19-yl-4-(dimeth-ylamino) butanoate (DLin-MC3-DMA) plus cholesterol, 1,2-distearoyl-sn-glycero-3-phosphocholine (DSPC) and á-(3'-{[1,2-di(myristyloxy)propanoxy] carbonylamino}propyl)-ω-methoxy polyoxyethylene (PEG2000-C-DMG). See also U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as pri-mary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include lipids (e.g. cholesterols or phospholipids), aminosugar, bio-tin, phenazine, folate, phenanthridine, anthraquinone, acri-dine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the com-pounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, the aminosugar N-acetylgalactosamine (GalNAc) (e.g., 1, 2, or 3 or more GalNAc; see, e.g., Springer and Dowdy, Nucleic Acid Ther. 2018 Jun. 1; 28(3): 109-118), lipid moieties such as a cholesterol moiety, cholic acid, a thioether, e.g., hexyl-5-tritylthiol, a thiocholesterol, an aliphatic chain, e.g., dode-candiol or undecyl residues, a phospholipid, e.g., di-hexa-decyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-car-bonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941;

4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

See also, Esmond & Chung, The Patent Landscape of siRNA Nanoparticle Delivery, 11 Nanotechnology Law & Business 15 (Spring 2014).

Locked Nucleic Acids (LNAs)

In some embodiments, the modified inhibitory nucleic acids used in the methods described herein comprise locked nucleic acid (LNA) molecules, e.g., including [alpha]-L-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., RNAs as described herein.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the RNA. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target RNA can be prepared, followed by testing for activity. Optionally, gaps, e.g., of 5-10 nucleotides or more, can be left between the LNAs, e.g., to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of more than four LNA residues, should be avoided where possible (for example, it may not be possible with very short (e.g., about 9-10 nt) oligonucleotides). In some embodiments, the LNAs are xylo-LNAs.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

See also Pendergraff et al., Mol Ther Nucleic Acids. 2017 Sep. 15; 8: 158-168.

Making and Using Inhibitory Nucleic Acids

The nucleic acid sequences described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems. Also provided herein are cells expressing the nucleic acids described herein, e.g., isolated cells in vitro.

Nucleic acid sequences described herein can be inserted into delivery vectors and expressed from transcription units within the vectors, e.g., for use in production of the nucleic acids or in gene therapy protocols. The recombinant vectors can be DNA plasmids or viral vectors. Viral vectors for use in the present methods and compositions can include recombinant retroviruses, adenovirus, adeno-associated virus, alphavirus, and lentivirus. Also provided herein are cells comprising the vectors, and optionally expressing the nucleic acids, e.g., producing the nucleic acids.

Non-native regulatory sequences, gene control sequences, promoters, non-coding sequences, introns, or coding sequences can be included in a vector for expression of a nucleic acid as disclosed herein. The inclusion of nucleic acid tags or signaling sequences, or nucleic acids encoding protein tags or protein signaling sequences, is further contemplated herein. Typically, the coding region is operably linked with one or more regulatory nucleic acid components. A promoter included in a nucleic acid as disclosed herein can be a tissue- or cell type specific promoter, a promoter specific to multiple tissues or cell types, an organ-specific promoter, a promoter specific to multiple organs, a systemic or ubiquitous promoter, or a nearly systemic or ubiquitous promoter. Promoters having stochastic expression, inducible expression, conditional expression, or otherwise discontinuous, inconstant, or unpredictable expression are also included within the scope of the present disclosure. A promoter can include any of the above characteristics or other promoter characteristics known in the art.

Generation of vector constructs can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences described herein can also be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences described herein can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-0 atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

In some embodiments, the inhibitory nucleic acid comprises standard template chemistry (STC), which replaces all of the 2'-OHs with an alternating 2'-F and 2'-OMe pattern (Huang, Mol Ther Nucleic Acids. 2017 Mar. 17; 6( ):116-132) or enhanced stability chemistry (ESC) (Huang and Liang, (2015) Prog Biochem Biophys 42:501-510) that increased the overall 2'-OMe content, while decreasing the 2'-F content (2'-OMe are more stable than 2'-F), as well as adding on two terminal phosphorothioates at each 5' end of the passenger (STC only contained phosphorothioates on the 3' end of the guide strand) (see WO2013074974, WO2016028649).

The inhibitory nucleic acids described herein can include any one, two, three, or more of the modifications described herein.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; *A Laboratory Manual* 3d ed. (2001); *Current Protocols in Molecular Biology*, Ausubel et al., eds. (John Wiley & Sons, Inc., New York 2010); Kriegler, Gene *Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitory nucleic acid sequences designed to target an RNA.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater. Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of (e.g., conjugation to or encapsulation in) lipids, e.g., lipid nanoparticles, e.g., cationic amino MC3 lipid nanoparticle comprising (6Z,9Z,28Z,31Z)-heptatriaconta-6, 9,28,31-tetraen-19-yl-4-(dimethylamino) butanoate (DLin-MC3-DMA) plus cholesterol, 1,2-distearoyl-sn-glycero-3-phosphocholine (DSPC) and α-(3-{[1C-di(myristyloxy) proponoxy]carbonylamino}propyl)-ω-methoxy, polyoxyethylene (PEG2000-C-DMG); or XTC (2,2-Dilinol-eyl-4-dimethylaminoethyl-[1,3]-dioxolane). See also U.S. Pat. Nos. 8,283,333, 8,058,069, 7,982,027, 7,901,708, and 7,799,565 (stable nucleic acid-lipid particle (SNALP)); 8,501,930 (Dynamic PolyConjugate (DPC); Witzigmann et al., Adv Drug Deliv Rev. 2020 Jul. 2; U.S. Pat. Nos. 10,053,689; 10,653,780; 9,029,338; US 20200138955; U.S. Pat. Nos. 10,456,473; 10,561,732; US 20190167800; US 20190167800; and WO 2010105209. In some embodiments, the nanoparticles comprise phospholipids and cholesterol.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is need of reduced triglyceride levels, or who is at risk of or has a disorder described herein, in an amount sufficient to cure, alleviate or partially arrest the clinical manifestations of the disorder or its complications; this can be called a therapeutically effective amount.

For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington: The Science and Practice of Pharmacy, 21st ed., 2005.

Various studies have reported successful mammalian dosing using complementary nucleic acid sequences. For example, Esau C., et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Kratzfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histopathological changes in the study animals.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

EXAMPLES

The invention is further described in the following examples, which do not limit the scope of the invention described in the claims.

Methods

The following materials and methods were used in the Examples below.

Animal Model

All mice were maintained and studied using protocols in accordance with the Guide for the Use and Care of Laboratory Animals and approved by MGH Animal Care and Use Committees (protocol numbers 2015N000029 and 2015N000070). Two- to three-month-old male C57BL/6J mice were purchased from the Jackson Laboratory.

Human Subjects

Heart tissue was from transplant patients with non-ischemic cardiomyopathy and reduced systolic function (EF=22.3±9.0%) and nonfailing (unused donor) hearts (EF=67.7±7.2%) from otherwise similar subjects (50% female and mean age 57 years for both). Plasma was from patients with HF with preserved ejection fraction (HFpEF, EF=64.7±7.76%), HF with reduced ejection fraction (HFrEF, EF=22.3±8.92%) and patients without HF and with structurally normal hearts who presented with supraventricular tachycardia (SVT, EF=60.8±2.3%). Human studies were approved by the Partners Institutional Review Board or the Colorado Multicenter Institutional Review Boards. Informed consent was obtained from all transplant patients and study participants, and from the family member or authorized representative of all organ donors.

Running Exercise Protocol

Two-month-old mice were subjected to running exercise as previously described.[1] Briefly, mice were individually housed in plexiglass cages (36L×20W×15H cm) that contained a stainless steel running wheel (diameter 11.4 cm; Mini-Mitter, Starr Life Science, USA) equipped with a tachometer. Mice ran voluntarily. Mouse activity was recorded daily. The sedentary control mice were kept in the same cage system lacking running wheels.

Transverse Aortic Constriction

Sham and transverse aortic constriction (TAC) surgeries were performed as previously described.[2,3] Briefly, thoracotomy was performed in anesthetized animals, and TAC was performed by ligating the transverse aortic arch with a 27-gauge needle between the innominate and left common carotid arteries. Subsequently, mice were followed weekly using echocardiography and sacrificed at 2 weeks or at fractional shortening lower than 30%.

Ischemia Reperfusion Model

Mice were subjected to ischemia reperfusion as previously described.[4] Briefly, the left anterior descending artery (LAD) was ligated with 7-0 silk. Following 30 min LAD occlusion, the LAD ligature was released, and reperfusion was confirmed visually. Sham mice served as controls. All surgeries and analysis were performed by investigators blinded to treatments. LNA-GapmeR (Qiagen) targeting lncExACT1 (LNA-GapmeR, 5'-T*A*A*A*G*G*C*A*C*T*T*G*A*T*C*G-3'; SEQ ID NO:3) or scrambled control (LNA-Control, 5'-A*A*C*A*C*G*T*C*T*A*T*A*C*G*C-3'; SEQ ID NO:4) reconstituted in saline was injected immediately at the end of ischemia at 10 mg/kg (phosphorothioate internucleotide linkages). Mice were injected for three consecutive days followed by weekly injection throughout the experiments.

Echocardiographic Studies

Cardiac echocardiography was performed on unanesthetized mice using a Vivid E90 cardiac ultrasound system (GE Healthcare) equipped with an L8-l8i-D transducer, as described.[3,5] The heart was first visualized in long and short axis views followed by M-mode analysis of short axis. Care was taken to obtain symmetrical short axis images at the level of the papillary muscles. Images were analyzed using EchoPACS software (version 201, GE Healthcare). At least three measurements were obtained and averaged for every data point from each mouse.

RNA Sequencing

RNA sequencing was performed by the MGH NextGen Sequencing Core. Total RNA was extracted from murine hearts using RNA prep kit. Libraries were constructed from polyA-selected RNA and sequenced on an Illumina HiSeq 2500 instrument in High-Output mode as paired end 100. Raw sequence files were converted to the FASTQ format using STAR aligner and were annotated using custom non-coding RNA annotation database combining list of lncRNAs from ENSEMBL, NONCODE, and lincRNAdb. R package DESeq2 was used for gene expression analysis. Genes were considered differentially expressed if fold-change >1.5 or <−1.5 with p value<0.05.

Quantitative Real-Time Polymerase Chain Reaction

RNA was isolated using RNA prep kit (Zymo Research). Polymerase chain reaction (PCR) reactions were performed using SYBR green and standard amplification protocols. Gene expression was normalized to RPS 18 or GAPDH and calculated using the $\Delta\Delta C_t$ method. Primer sequences are listed in Table A.

TABLE A

| List of primers used in QPCR and ddPCR, and guide RNA sequencing used in CRISPR/dCAS9 system | | | | |
| --- | --- | --- | --- | --- |
| Primer name | Forward | # | Reverse | # |
| mlncExACT 1 | GCGAGCCTCG GTTCTGTA | 6. | CCCATCAGCGTCAC TGTCT | 7. |
| rlncExACT 1 | TGGCCAGCCA TATGTAGGGA | 8. | TTTTGTCAGGGGTA CAGGGTG | 9. |
| hlncExACT 1 | GGCCAAGTGC CAAGTGATGA | 10. | AGCTATGCATCGGC CTTTGA | 11. |
| mlncExACT 2 | GGCATAAAGG GAACGAGGGA | 12. | GCACAATTCTGAGC TTGGACC | 13. |
| mlncExACT 3 | CGTGGAAGGA CCCTAGTGAA G | 14. | TGCAAGGGACAGAA CACCAT | 15. |

TABLE A-continued

List of primers used in QPCR and ddPCR, and
guide RNA sequencing used in CRISPR/dCAS9
system

| Primer name | Forward | # | Reverse | # |
|---|---|---|---|---|
| mlncExACT 4 | TGCAGTGGGA AGAGCATACC | 16. | CAGTTCCCTTGTGC AGGGTT | 17. |
| mlncExACT 5 | TCTGCAGGAC TGATTGTTTT ATGCT | 18. | TGTCTGTCTGTCTC TCTCTCTCT | 19. |
| mDCHS2 | CATCTCTTCA GATTATCCTG CTC | 20. | TCATGTGAAAGGAT CGAGGT | 21. |
| rDCHS2 | TGCAGGTAAA AGCCTCGGAC | 22. | CTCCACTTCCACCC GAACAA | 23. |
| hDCHS2 | GAGTTTGAAA GGCCTAAGTA CAC | 24. | CTGAGGAGTTCAAG GGCTC | 25. |
| ANP | GTAGGATTGA CAGGATTGGA | 26. | TCCTCCTTGGCTGT TATC | 27. |
| BNP | GCTGCTGGAG CTGATAAGAG AA | 28. | GTTCTTTTGTAGGG CCTTGGTC | 29. |
| αMHC | ACATCAGTCA GCAGAACA | 30. | TTCCTCTAGCCTCT CACT | 31. |
| βMHC | GCTGTTATTG CTGCCATT | 32. | TTATCATTCCGAAC TGTC | 33. |
| PGC1α | TGATGTGAAT GACCTGGACA CAGACA | 34. | GCTCATTGTTGTAC TGGTTGGATATG | 35. |
| mC/EBPβ | ATATGAATTC GCCACCATGC ACCGCCTGCT GGCCTGGGAC GCA | 36. | GCACCTCGAGTCAA GTCCCGAAACCCGG TGCGCTGTG | 37. |
| ETS1 | CCTGCAGAAA GAGGATGTG | 38. | TAATCCGAGGTGTA ACGGG | 39. |
| MCM10 | GCAAGGGACT GTCATAGGG | 40. | TCGATAGATAAGCA CACCTCC | 41. |
| MYBL1 | TATTGAATCG GATCCTGTAG C | 42. | GTAGACTTGACAGG AGAAGC | 43. |
| BUB1 | ACAACAATAC AGGCTATTCC AG | 44. | CTATGCAAAGGTTC TGAGGT | 45. |
| CDCA8 | TTGACTACTT TGCCCTAGGA | 46. | TGTTTATCTCTGTG ATGTCTCG | 47. |
| KLF23 | AGAATCGCCA ACTGGTAGTC | 48. | GTCCATTCAGACTC TGTACCA | 49. |
| U6 | CTCGCTTCGG CAGCACA | 50. | AACGCTTCACGAAT TTGCGT | 51. |
| GAPDH | ACAGCAACAG GGTGGTGGAC | 52. | TTTGAGGGTGCAGC GAACTT | 53. |
| hGAPDH | GGAGCGAGAT CCCTCCAAAA T | 54. | GGCTGTTGTCATAC TTCTCATGG | 55. |

TABLE A-continued

List of primers used in QPCR and ddPCR, and
guide RNA sequencing used in CRISPR/dCAS9
system

| Primer name | Forward | # | Reverse | # |
|---|---|---|---|---|
| RPS18 | CATGCAGAAC CCACGACAGT A | 56. | CCTCACGCAGCTTG TTGTCTA | 57. |
| hRPS18 | CAACACCAAC ATCGATGGGC | 58. | GGTGATCACACGTT CCACCT | 59. |
| Beta-Actin | GGCTGTATTC CCCTCCATCG | 60. | CCAGTTGGTAACAA TGCCATGT | 61. |
| HOTAIR | CTTTCAAGGC CTGTCTCCTG | 62. | CAACATTCTAGCTG CACGGA | 63. |
| hlncExACT 1-ddPCR | GGCCAAGTGC CAAGTGATGA | 64. | AGCTATGCATCGGC CTTTGA | 65. |
| Probe: | CCGTCCCTCT GCAGGCCTGA C | 66. | | |
| Guide RNA for DCHS2 | | | AAACCCATTGAGCA CTGAGGAGTCC | 67. |
| Guide RNA for Control | | | GCACTCACATCGCT ACATCA | 68. |

, SEQ ID NO:

Droplet Digital Polymerase Chain Reaction

Droplet digital polymerase chain reaction (ddPCR) was performed in QX200 (Bio-Rad) as described[6]. Briefly, total RNA was isolated from human plasma using miRNease Serum/Plasma kit (Qiagen). Total amount of RNA extracted from plasma (500 ul) was used for reverse transcription using standard amplification protocol from High Capacity Reverse Transcription (RT) Kit (Applied Biosystems). PCR reactions were performed using ddPCR Supermix for Probes (Bio-Rad), Taqman primers (listed in Table A) and RT reactions as template. Reactions (40 ul) were loaded into DG8 cartridges with QX200 droplet Generation Oil for Probes (70 ul, Bio-Rad) then subjected to QX200 droplet Generator for droplet generation. Droplet suspensions were then transferred to ddPCR plates. Readout was done using the QX200 Droplet Reader and Quantasoft Software (Bio-Rad) to determine the total number of droplets. Only genes that had at least 10,000 droplets were considered robustly detectable by ddPCR in plasma and subsequently underwent further analysis.

Cardiomyocytes Isolation, Culture, and Transfection

Cardiomyocytes and non-cardiomyocytes were isolated from adult mice as previously described[4]. Briefly, after Langendorff perfusion, left ventricles were harvested and dissected into small pieces to dissociate in transfer buffer. After filtering, cell solution was settled to sedimentation for several minutes in a Falcon tube. The cell pellet and supernatant were transferred to individual Falcon tubes for further separation. The cell pellet was resuspended in transfer buffer and settled to precipitation. After the second precipitation, the cell pellet was checked for typical rod-shaped morphology before RNA extraction to confirm expression of cardiomyocyte markers (Troponin I and troponin T). The initial supernatant was centrifuged first at 50×g for 3 min and then 300×g for 5 min before confirmation of non-cardiomyocyte identity of pelleted cells by QRT-PCR for cardiomyocytes markers (Troponin I and troponin T).

Primary neonatal rat ventricular cardiomyocytes (NRVMs) were prepared as described[7]. Isolated NRVMs were purified by pre-plating and plated in 60 mm dishes at $1 \times 10^6$ cells per well and cultured in DMEM supplemented with 5% FBS and 10% horse serum for 24 hours. Before treatment, NRVMs were synchronized and cultured in DMEM containing 0.2% FBS. Twenty-four hours after plating, cells were transfected with negative control (20 mM; LG00000002-DDA, Qiagen) or LNA-GapmeR (20 mM; LG00235955-DDA, Qiagen); or scramble control (20 mM; 129351000, Invitrogen) or DCHS2 siRNA (20 mM; RSS318591, Invitrogen); or scramble controls or miR-222 inhibitor[4] (20 mM) or miR-222 precursor[4] (0.4 mM) for forty-eight hours, using Lipofectamine RNAiMAX (Invitrogen) according to the manufacturer's instruction.

Primary neonatal mouse ventricular cardiomyocytes were prepared using Pierce Primary Cardiomyocyte Isolation Kit (Thermo Scientific) according to the manufacturer's instruction.

Transfection of GapmeR in 293T Cells 293T cells were plated in 60 mm dishes at $1 \times 10^6$ cells per well and cultured in DMEM supplemented with 10% FBS for 24 hours. Before treatment, 293T cells were synchronized and cultured in DMEM containing 10% FBS. Twenty-four hours after plating, cells were transfected with negative control (20 mM; LG00000002-DDA, Qiagen) or LNA-GapmeR (20 mM; 5'-T*C*A*T*T*C*C*T*G*G*T*G*G*C*A*G-3'; SEQ ID NO:5, Qiagen) for forty-eight hours, using Lipofectamine RNAiMAX (Invitrogen) according to the manufacturer's instruction.

Isolation of Cytosolic and Nuclear Fractions

Isolated adult cardiomyocytes were suspended and washed with PBS and harvested for isolation of cytosolic and nuclear fractions according to the manufacturer's protocol as described in PARIS kit (Life Technologies) followed by RNA extraction and QRT-PCR. Beta-actin was used as cytosolic marker and U6 was used as nuclear marker. Previously described lncRNA HOTAIR[8], predominantly expressed in the nucleus, was used as positive control.

Hearts from mice were cleared of blood by washing thoroughly in Tyrode buffer and aortic and atrial sections removed from the ventricles. Ventricular tissues were fractionated to isolate cytosolic and nuclear fractions according to the manufacturer's protocol as described in the Nuclear and Cytoplasmic Extraction Kit (Thermo Fisher Scientific).

Fluorescence In Situ Hybridization

Stellaris fluorescence in situ hybridization (FISH) was performed as described[9]. Briefly, after isolation, adult mouse cardiomyocytes were cultured on 18 mm round coverglass slips in a 12-well plate and cultured for 6 hours. Cells were fixed with 3.7% (v/v) formaldehyde followed by permeabilized with 70% ethanol for 1 hour at 4° C. Cells were washed with Buffer A (Biosearch Technologies) then hybridized with probes recognizing mouse lncExACT1 (SMF-1001-5) labeled with TAMRA (Biosearch Technologies) in Stellaris RNA FISH Hybridization Buffer (Biosearch Technologies) for 16 hours in the dark at 37° C. in a humidified chamber, followed by incubation with primary antibody α-Actinin (ab9465, Abcam) and secondary antibody goat-anti-mouse 488 (A11001, Life Technology) for 2 hours in the dark at room temperature. After removing the staining solution and washed with Buffer B (Biosearch Technologies), the coverslips were mounted in ProLong Gold Antifade Mountant with DAPI mounting medium (Invitrogen) and images were taken.

Luciferase Assays

Fragments containing the miR-876- and miR-222-binding sites of lncExACT1 were inserted downstream of Renilla luciferase in a dual luciferase reporter plasmid with firefly luciferase expression driven by a separate promotor (psiCHECK-2, Promega). Control constructs contained the same fragments but with the putative binding sites mutated. HEK293T cells were co-transfected with the reporter plasmid or the mutated construct (100 ng) and miR-876 precursor (1 μM, Qiagen), miR-222 precursor (1 μM, Qiagen) or scrambled control (1 μM, Qiagen) according to the lipofectamine 3000 transfection procedures (Invitrogen). Forty-eight hours after transfection, cells were lysed. Relative (Renilla/firefly) luciferase expression was measured on a multi-mode multi-format reader SpectraMax M5 (Molecular Devices). To examine the effect of lncExACT1 on DCHS2 transcription, the DCHS2 promoter region was divided into different fragments. Fragments were synthesized by IDT and inserted into the same dual luciferase reporter plasmid psiCHECK-2 (Promega). A scrambled control that did not match the mouse genome was inserted into psiCHECK-2 and used as negative control. Mouse neonatal cardiomyocytes were co-transfected with the reporter plasmid or the control construct (100 ng) with or without lncExACT1 LNA-GapmeR or lentivirus overexpressing lncExACT1 according to the lipofectamine 3000 transfection procedures (Invitrogen). Forty-eight hours after transfection, cells were lysed and relative luciferase expression was measured.

5-Ethynyl-2'-Deoxyuridine Incorporation Labeling

Isolated NRVMs were plated into a 6 cm diameter BD Primaria tissue culture dish. Twenty-four hours after plating, cells were subjected to various treatments. Forty-eight hours after treatments, cells were labeled with 20 μM 5-Ethynyl-2'-deoxyuridine (EdU, Invitrogen) for 24 hours. Collected cells were stained using the Click-iT Plus EdU Pacific Blue Flow Cytometry Assay protocol (Thermo Fisher Scientific) and cardiac troponin T (Alexa Fluor 647, BD Bioscience, 565744) as cardiomyocyte marker. Stained cells were analyzed in a 5-laser LSR II machine in the MGH flow cytometry core facility. At least 10,000 events were recorded by flow cytometry in each treatment. Flowjo 10 was used to analyze flow data. To quantify cardiomyocyte proliferation in vivo in mice, EdU (50 mg/kg) was subcutaneously injected every 2 days for the last two weeks after LNA-GapmeR or AAV injections. At the end of experiments, hearts were snap frozen in OCT in liquid nitrogen, sectioned and processed for EdU staining according to the of Click-iT EdU Flow Cytometry Assay (Invitrogen) protocol with PCM1 (HPA023370, Sigma-Aldrich) as cardiomyocyte marker.

Generation and Transfection of Lentivirus Overexpressing lncExACT1

The full-length lncExACT1 genomic sequence was cloned and inserted into a modified pLVX-Tight-Puro vector (TER promoter was replaced by EF1a promoter from pLVX-Tight-Puro) at BclI and MluI sites for generating lncExACT1 overexpression lentivirus vector. Lentiviral construct was transfected into the HEK293T cells along with lentiviral packaging plasmids psPAX2 and VSVG using Lipofectamine 3000 (Invitrogen). Virus-containing supernatant was collected and cellular debris was removed by syringe filtration (0.22 μm pore size; Millipore). Filtered supernatant was concentrated using lenti-X Concentrator (Clontech). The viral pellet was resuspended in serum-free DMEM. For infection in NRVMs, 24 hours after plating, NRVMs were incubated with DMEM medium containing lentivirus over-expressing lncExACT1 and polybrene (6 μg/ml, Millipore) for 48 hours.

CRISPR/dCAS9 and sgRNA Construct Design

For transcriptional activation of DCHS2 in NRVMs, single guide RNAs targeting the DCHS2 promoter were designed using IDT crRNA design tool and analyzed for specificity (idtdna.com/site/order/designtool/index/CRISPR_CUSTOM). Three guide RNAs targeting the DCHS2 promoter and one guide RNA not targeting rat genome (as control), sequences of guide RNAs were listed in Table A. Guide RNA was inserted into the lentiGuide-Puro vector (52963, Addgene)[10] at the BsmBI site. lentiGuide-Puro vector and lenti-dCAS-VP64_Blast vector (61425, Addgene)[11] were packaged as lentivirus using psPAX2 and VSVG. lentiGudie-Puro lentivirus and lenti-dCAS-VP64_Blast lentivirus were infected into NRVMs for 48 hours to activate DCHS2 transcription.

RNA Pulldown

RNA pulldown was performed as previously described[12]. Briefly, a mixture of twenty-five 3'-end-labelled DNA oligonucleotide probes targeting lncExACT1 was synthesized (IDT), listed in Table B. Forty-eight hours after infection with lncExACT1-overexpressing lentivirus, mouse neonatal cardiomyocytes were rinsed with PBS, fixed with 1% paraformaldehyde, and cross-linked under agitation for 10 min at room temperature, then quenched by adding 1/10 volume of glycine. After two PBS washes, cells were collected. Cells were then lysed (50 mM Tris-HCl pH 7.0, 10 mM EDTA, 1% SDS supplemented with 200 U/mL of a RNAse inhibitor solution (Invitrogen, 10777019), and a cocktail of protease inhibitors 5 μL/mL (Thermo Scientific, 78442)) and processed to a series of sonication. Supernatants were then hybridized with biotinylated probes for 6 hours under moderate agitation at room temperature followed by incubation with magnetic streptavidin beads (Invitrogen) supplemented with 200U/ml of RNAse inhibitor and protease inhibitor cocktail, overnight at room temperature. Beads were collected using a magnetic stand and washed five times with wash buffer (0.5% SDS, SSC 2×) and digested with proteinase K for 45 min at 50° C., then 10 min at 95° C. Beads were then removed and supernatant was processed for RNA extraction using standard protocol.

TABLE B

List of probes for RNA pulldown
(Biotinylated modification at the 3'
end for each probe)

| ID | Antisense | # | Sense | # |
|----|-----------|---|-------|---|
| 1 | TCCTAAAGAGCTGGAGGAGA | 69. | CTGAGATCCCAATACAAGCT | 70. |
| 2 | GATGGGACTCCCTTAAAGAC | 71. | AGCCGAGCAGAACAAGGAAC | 72. |
| 3 | TCCTCCTTTTTGGCAAAAGA | 73. | TTTCCTCCTTTTTGGCAAAA | 74. |
| 4 | GTACACTTTGCACGCAAAGC | 75. | CTGTTCTGAGGATGGAGAGA | 76. |
| 5 | CTGTTCTGAGGATGGAGAGA | 77. | GCACAAGTTTGTCTCCTTAA | 78. |
| 6 | GGCATAATAAAGCGTGCCAT | 79. | GTGTCACAGATTTTTTCGGG | 80. |

40

TABLE B-continued

List of probes for RNA pulldown
(Biotinylated modification at the 3'
end for each probe)

| ID | Antisense | # | Sense | # |
|----|-----------|---|-------|---|
| 7 | TGGATGCCTAAAAAGGTCCG | 81. | CGCTGCTAAATAGTAGCTCG | 82. |
| 8 | TTGGATTCAACCCTAAGCTA | 83. | TGGATGCCTAAAAAGGTCCG | 84. |
| 9 | GCATACTTTATTAGAGGCCA | 85. | TTGGATTCAACCCTAAGCTA | 86. |
| 10 | CCTAGCACAGAACAGTATCT | 87. | TCAGTTTCCATCTATAGCTG | 88. |
| 11 | ATGCATAGGCCACTCAATAT | 89. | CCTAGCACAGAACAGTATCT | 90. |
| 12 | TGGTTACATACAACACTGCC | 91. | ATGCATAGGCCACTCAATAT | 92. |
| 13 | GTAGTTGTGGTGCTTTGTAA | 93. | ATGCCTTTGCATTAAGTTGG | 94. |
| 14 | GATTCTTCAATGAGCAGGGA | 95. | GTAGTTGTGGTGCTTTGTAA | 96. |
| 15 | CTCAGTTGGCATCTTACATG | 97. | AAAGGCTTAGTGTTGGCTTT | 98. |
| 16 | TGTGAGGATCTAGGTTTACC | 99. | GAAGAGCAAGGTGGGCAATT | 100. |
| 17 | CAAGCTGATCTCAGGTACTT | 101 | CTCAGTTGGCATCTTACATG | 102. |
| 18 | ACCAAACACTCTCTCAGACT | 103 | CTAGAAGGAGGGTAGTCAGG | 104. |
| 19 | TAGTIGTGGTTTCCAAGTTC | 105 | TGTGAGGATCTAGGTTTACC | 106. |
| 20 | CAAAGCTGGGACTCAGTACA | 107 | CAAGCTGATCTCAGGTACTT | 108. |
| 21 | ACCTCTGTTAACAAAGTCCG | 109 | GGGTTAAAGCAGCGCTTTAA | 110. |
| 22 | CTGAGATCCCAATACAAGCT | 111 | ACCAAACACTCTCTCAGACT | 112. |
| 23 | AGCCGAGCAGAACAAGGAAC | 113 | TAGTTGTGGTTTCCAAGTTC | 114. |
| 24 | TCCTCCTTTTTGGCAAAAGA | 115 | CAAAGCTGGGACTCAGTACA | 116. |

, SEQ ID NO:

Generation and Injection of Adeno-Associated Virus

AAV9 vector with cardiomyocyte-specific troponin I promoter was provided by the Seidman Lab[13]. AAV9-lncExACT1 was constructed by subcloning the full-length mouse lncExACT1 genomic fragment into an AAV9 vector at NcoI and BsrGI sites. Recombinant AAV9-GFP and AAV9-lncExACT1 were produced using a triple transfection approach in HEK293T cells in 15 cm dishes with polyethylenimine and were harvested after 60 hours incubation, purified by filtration and iodixanol gradient ultracentrifugation, and quantified as described[14]. A total amount of 2×10^12 GC/mouse of AAV9-GFP or AAV9-lncExACT1 was delivered by tail vein injection to 12-week-old C57BL/6J mice.

Locked Nucleic Acid-GapmeR Injection

Locked nucleic acid (LNA) treatment was performed as described[4,15]. Briefly, 12-wk-old C57BL/6 male mice at baseline or 3 days before TAC surgery were injected subcutaneously with 10 mg/kg of LNA-GapmeR (Qiagen) targeting lncExACT1 (LNA-GapmeR, 5'-TAAAGGCACTTGATCG-3'; SEQ ID NO:3) or scrambled control (LNA-Control, 5'-AACACGTC-TATACGC-3'; SEQ ID NO:4) reconstituted in saline. Mice were injected for three consecutive days followed by weekly injection throughout the experiments.

Histology and Immunohistochemistry

Mid-ventricular sections were stained with Wheat Germ Agglutinin (WGA), Alexa Fluor™ 594 (W11262, Thermo Fisher Scientific) for cell size measurement and Masson's Trichrome staining was carried out for fibrosis analysis, according to manufacturer's instruction (HT15, Sigma-Aldrich). WGA and Masson's Trichrome stained slides were scanned by a digital slide scanner, NanoZoomer 2.0-RS (Hamamatsu, Japan). For cardiomyocyte proliferation analysis, immunofluorescent double staining was performed. Anti-PCM1 antibody (HPA023374, Sigma-Aldrich) was incubated at 4° C. overnight and a biotinylated secondary antibody followed by streptavidin-DyLight 594 (BA1000 and SA-5594, Vector Laboratories) were used for cardiomyocyte identification. For a proliferation marker, Click-iT™ Plus EdU Cell Proliferation Kit for Imaging, Alexa Fluor™488 dye (C10337, Thermo Fisher Scientific) was used. As another proliferation maker, anti-Ki67 antibody (clone: SolA15, 14-5698-82, Thermo Fisher Scientific) and Alexa Fluor 488 goat anti-rat IgG secondary antibody (A-11006, Thermo Fisher Scientific) were applied. Nuclei were counterstained with DAPI (D21490, Thermo Fisher Scientific) and the slides were imaged on a Leica DM500B Microscope. Cardiomyocyte cross-sectional area (~250 cells per heart) were measured from six randomly selected sections per heart using ImageJ (NIH). Fibrosis, EdU and PCM1 double positive cardiomyocytes, and Ki67 and PCM1 double positive cardiomyocytes were quantified from full mid-ventricular section (Keyence BZ-X Analyzer for fibrosis, ImageJ for others). Image analysis was blinded.

Immunoblotting

Protein was isolated using radioimmunoprecipitation assay (RIPA) buffer and processed using standard Western blotting protocols. Image quantification was performed with the ChemiDoc system (Bio-Rad). Cytosolic phosphorylation of Yap1 protein expression was normalized to GAPDH, nuclear total Yap1 protein expression was normalized to Histone H3. The following primary antibodies were used: rabbit-anti-mouse phosphor-Yap1 (Ser127) (1:2000; 13008, Cell Signaling Technology), rabbit-anti-mouse Yap1 (1:2000; NB110-58358, Novus Biologicals), rabbit-anti-mouse GAPDH (1:3000; 2118, Cell Signaling Technology), rabbit-anti-mouse Histone H3 (1:5000; 9715, Cell Signaling Technology).

Statistical Analysis

Figure 1A:
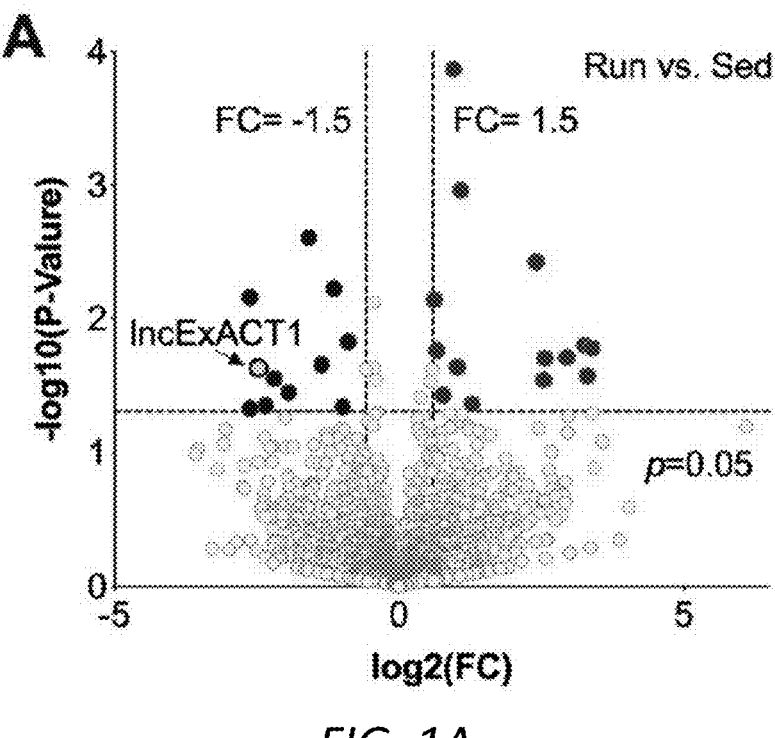
FIGS. 1A-E. Identification of exercise-associated cardiac lncRNAs. A. Volcano plot showing lncRNA RNAseq result from exercised compared with sedentary hearts. B. Venn diagram showing overlap in differentially regulated lncRNAs from exercised (Run) hearts, transverse aortic constriction (TAC)-induced left ventricular hypertrophic (TAC-LVH) and heart failure hearts (TAC-HF). C. Expression of lncExACT1 in hearts from control (Ctrl), exercised (Run), TAC-LVH, and TAC-HF. D. lncExACT1 expression in the heart from heart failure patients (HF) and controls. E. lncExACT1 expression in plasma from individuals without heart failure who presented with supraventricular tachycardia (SVT) and patients with HF with preserved ejection fraction (HFpEF) and HF with reduced ejection fraction (HFrEF). *p<0.05 vs. Ctrl, **p<0.01 vs. Ctrl, n=4-5 per groups in A and C. Data are shown as mean±SEM.
Figure 1B:
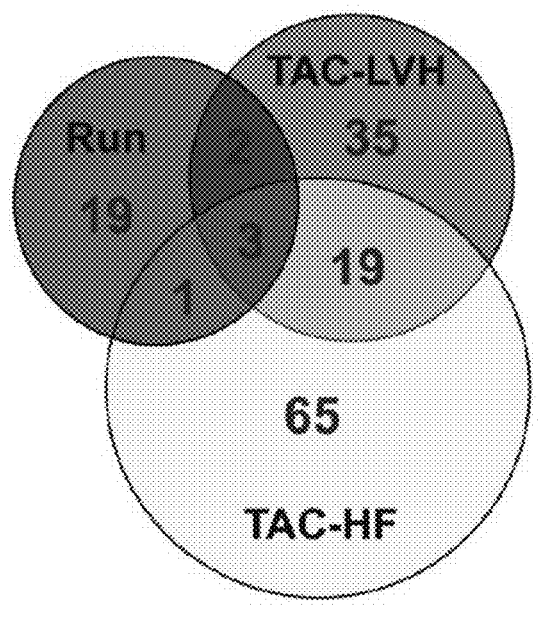
Figure 1C:
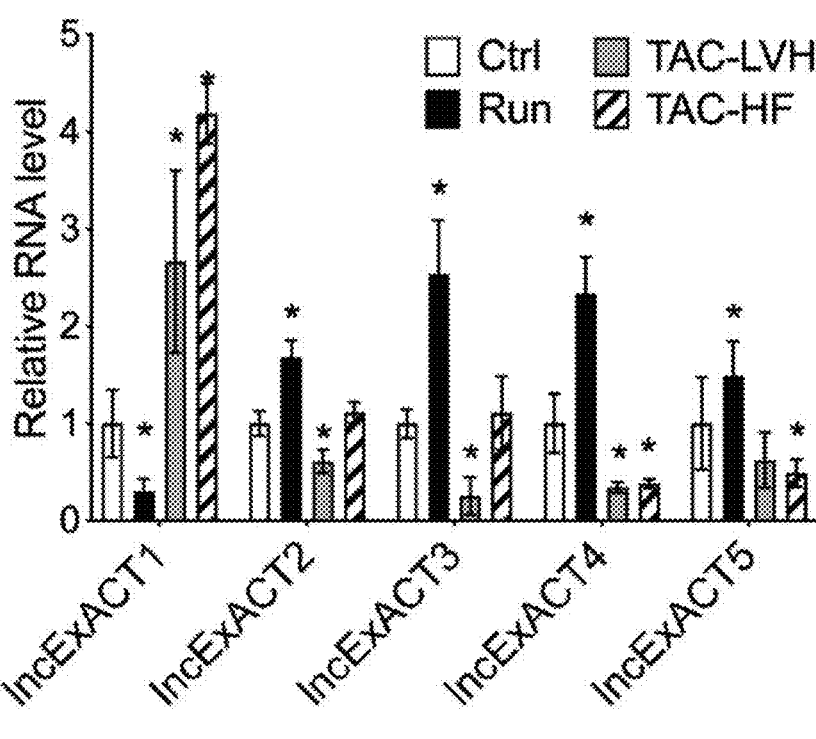

Data are presented as mean±SEM unless otherwise indicated. Unpaired, two-tailed Student's t test was used when indicated with $p<0.05$ considered significant. When assessing multiple groups, one-way ANOVA was utilized with Tukey's post hoc test. In FIG. 1E, pairwise Wilcoxon rank sum test with Bonferroni correction was used when indicated with $p<0.05$ considered significant. The statistical software used was GraphPad Prism 8 (GraphPad Software).

References for Methods:
1 Vujic, A. et al. Exercise induces new cardiomyocyte generation in the adult mammalian heart. Nat Commun 9, 1659, doi:10.1038/s41467-018-04083-1 (2018).
2 Bostrom, P. et al. C/EBPbeta controls exercise-induced cardiac growth and protects against pathological cardiac remodeling. Cell 143, 1072-1083, doi:10.1016/j.cell.2010.11.036 (2010).
3 Roh, J. D. et al. Activin type II receptor signaling in cardiac aging and heart failure. Sci Transl Med 11, doi:10.1126/scitranslmed.aau8680 (2019).
4 Liu, X. et al. miR-222 is necessary for exercise-induced cardiac growth and protects against pathological cardiac remodeling. Cell Metab 21, 584-595, doi:10.1016/j.cmet.2015.02.014 (2015).
5 Bezzerides, V. J. et al. CITED4 induces physiologic hypertrophy and promotes functional recovery after ischemic injury. JCI Insight 1, doi:10.1172/jci.insight.85904 (2016).
6 Engreitz, J. M. et al. Local regulation of gene expression by lncRNA promoters, transcription and splicing. Nature 539, 452-455, doi:10.1038/nature20149 (2016).
7 Matsui, T. et al. Akt activation preserves cardiac function and prevents injury after transient cardiac ischemia in vivo. Circulation 104, 330-335, doi:10.1161/01.cir.104.3.330 (2001).
8 Gupta, R. A. et al. Long non-coding RNA HOTAIR reprograms chromatin state to promote cancer metastasis. Nature 464, 1071-1076, doi:10.1038/nature08975 (2010).
9 Kenneweg, F. et al. Long Noncoding RNA-Enriched Vesicles Secreted by Hypoxic Cardiomyocytes Drive Cardiac Fibrosis. Mol Ther Nucleic Acids 18, 363-374, doi:10.1016/j.omtn.2019.09.003 (2019).
10 Sanjana, N. E., Shalem, O. & Zhang, F. Improved vectors and genome-wide libraries for CRISPR screening. Nat Methods 11, 783-784, doi:10.1038/nmeth.3047 (2014).
11 Konermann, S. et al. Genome-scale transcriptional activation by an engineered CRISPR-Cas9 complex. Nature 517, 583-588, doi:10.1038/nature14136 (2015).
12 Torres, M. et al. RNA Pull-down Procedure to Identify RNA Targets of a Long Non-coding RNA. J Vis Exp, doi:10.3791/57379 (2018).
13 Jiang, J., Wakimoto, H., Seidman, J. G. & Seidman, C. E. Allele-specific silencing of mutant Myh6 transcripts in mice suppresses hypertrophic cardiomyopathy. Science 342, 111-114, doi:10.1126/science.1236921 (2013).
14 Pleger, S. T. et al. Cardiac AAV9-S100A1 gene therapy rescues post-ischemic heart failure in a preclinical large animal model. Sci Transl Med 3, 92ra64, doi:10.1126/scitranslmed.3002097 (2011).
15 Viereck, J. et al. Long noncoding RNA Chast promotes cardiac remodeling. Sci Transl Med 8, 326ra322, doi:10.1126/scitranslmed.aaf1475 (2016).

Example 1. Identification and Characterization of Exercise Associated Cardiac lncRNAs To identify cardiac lncRNAs dynamically regulated by exercise, RNAseq was performed on hearts from sedentary mice and mice subjected to voluntary running for 8 weeks, a model of physiological cardiac growth with a robust increase in cardiomyogenesis[11]. For comparison, RNAseq was also performed on hearts from mice subjected to transverse aortic constriction (TAC) to induce either pathological cardiac hypertrophy (2 weeks after TAC) or HF (8 weeks after TAC). Exercised mice ran 5-7 km/day and developed cardiac hypertrophy with normal cardiac function and a physiological hypertrophic gene expression pattern (FIGS.

8A-D). We previously demonstrated that this exercise regimen induces a robust increase in cardiomyogenesis[11]. Two weeks after TAC, mice also developed cardiac hypertrophy with preserved systolic function but manifested a gene expression pattern consistent with pathological hypertrophy (FIGS. 8E-H). By eight weeks after TAC, mice had developed cardiac dysfunction and increased lung weights consistent with HF (FIGS. 8I-L). Comparing RNAseq results from exercised and sedentary mice, we found 25 lncRNAs that were differentially expressed (11 downregulated and 14 upregulated) in hearts from exercised compared with sedentary mice (FIG. 1A). We named these long noncoding Exercise-Associated Cardiac Transcripts (lncExACTs). Of these, six were also changed in the pathological models; in each case in a direction opposite to that seen with exercise (FIG. 1B). Five of these validated by QPCR in independent cohorts (FIG. 1C). Among them, lncExACT1 was chosen for further detailed study because it was the only lncExACT altered in both the physiological and pathological models that was downregulated in exercised hearts, suggesting antisense inhibition that could be exploited therapeutically[26].

Figure 9A:
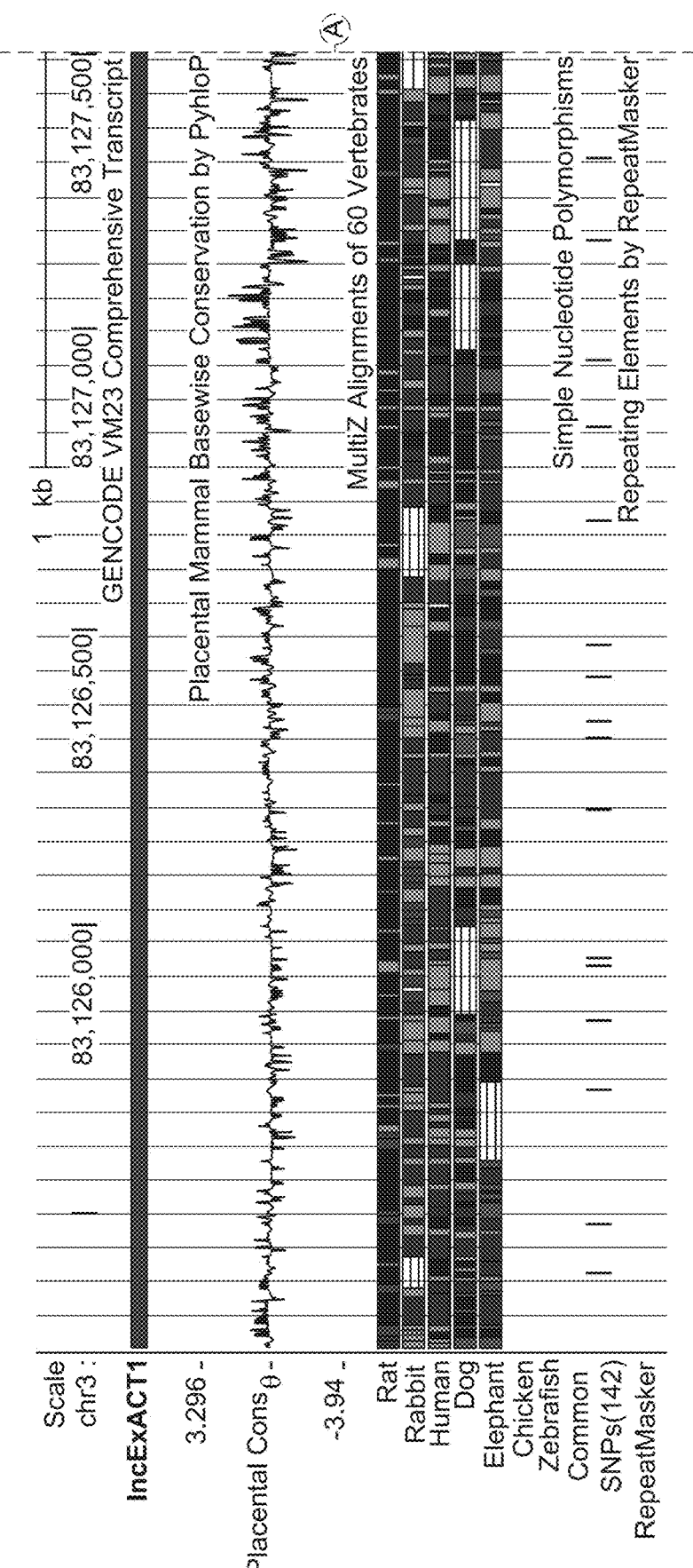
Figure 9A:
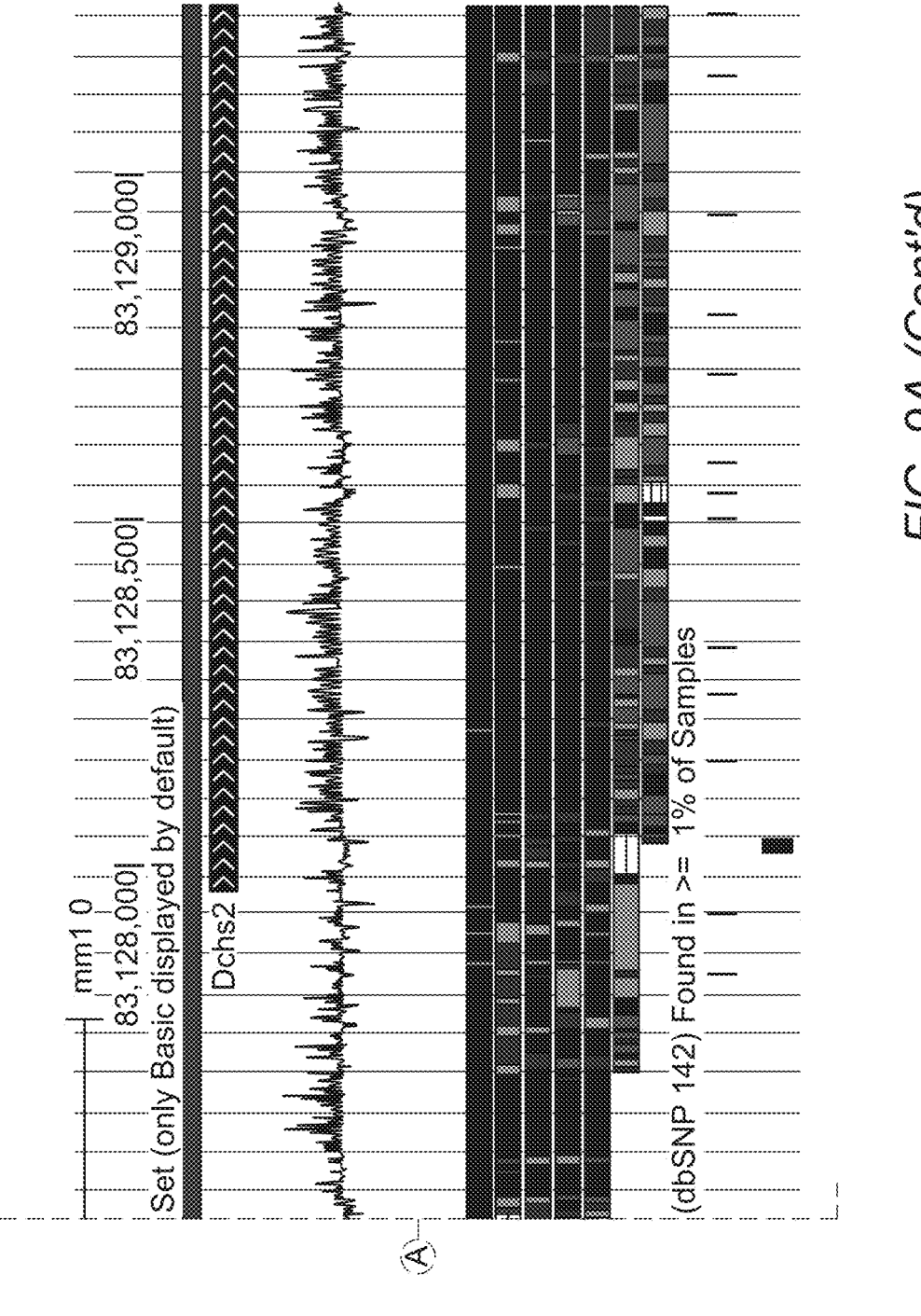
Figure 9D:
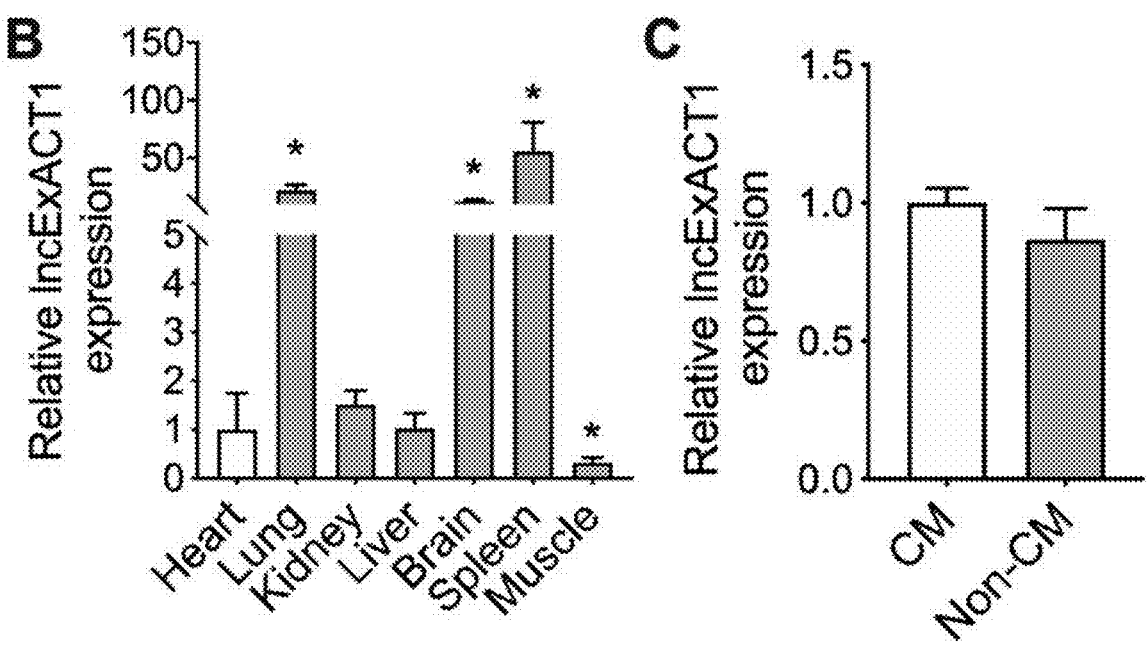
Figure 9D:
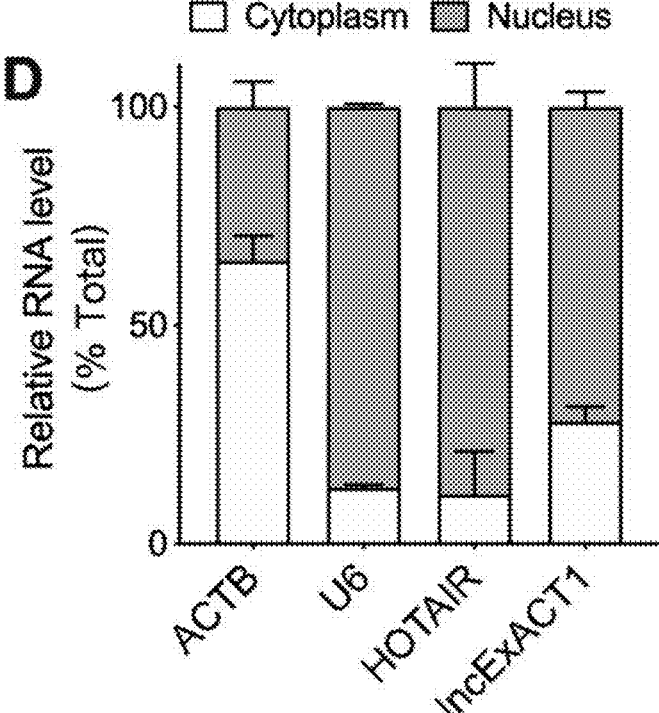

The full-length sequence of lncExACT1 was confirmed by 3' and 5' rapid amplification of cDNA ends (RACE). lncExACT1 is highly conserved across mammalian species (FIG. 9A), and the mouse ortholog of lncExACT1 (SEQ ID NO:2) exhibits 67% nucleotide identity with its human counterpart (SEQ ID NO:1). Analysis using the Coding Potential Assessment Tool (lilab.research.bcm.edu/cpat/) failed to identify any major open-reading frames (ORF) with translational potential longer than 100 amino acids. lncExACT1 is expressed by many tissues (FIG. 9B), including the heart, in which expression is comparable in cardiomyocytes and non-cardiomyocytes (FIG. 9C). In cardiomyocytes, lncExACT1 is predominantly but not exclusively present in the nucleus as indicated by QPCR and in situ hybridization in isolated mouse cardiomyocytes (FIGS. 9D-E).

Figure 1D:
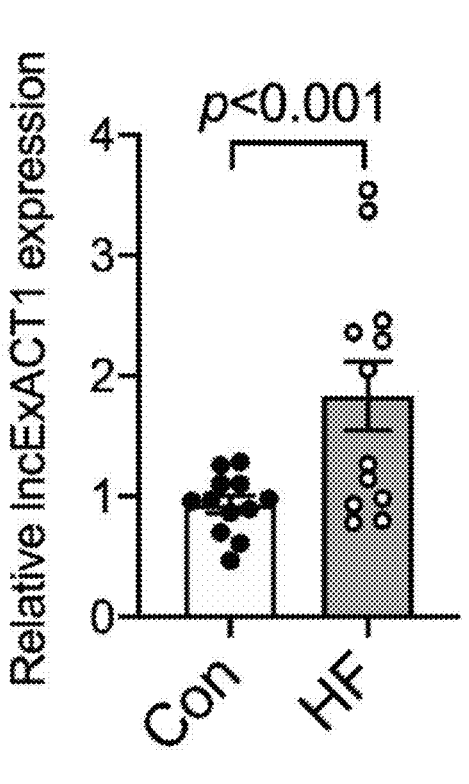
Figure 1E:
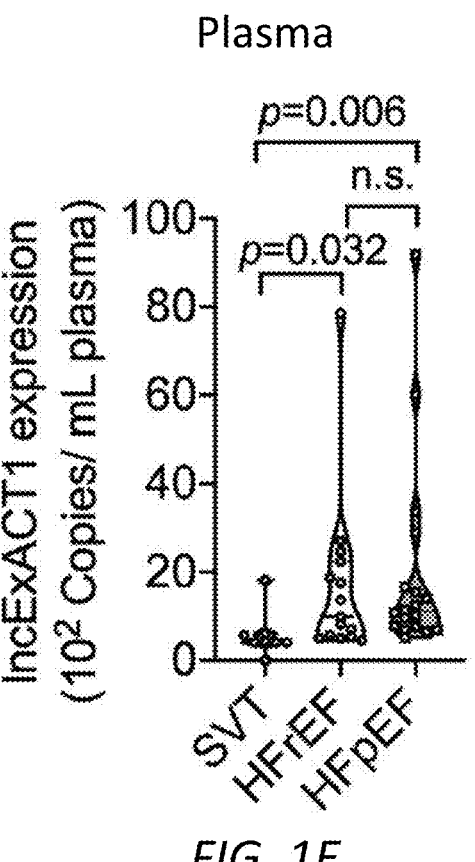

To see if lncExACT1 is also regulated in human heart failure, we examined explanted hearts from patients with non-ischemic cardiomyopathy and reduced systolic function (EF=22.3±9.0%, n=12) in comparison to nonfailing (unused donor) hearts (EF=67.7±7.2%, n=12, p<10$^{-11}$) from otherwise similar subjects (50% female and mean age 57 years for both, p>0.7). lncExACT1 expression was increased ~1.8-fold by QPCR in failing hearts (FIG. 1D,p<0.001). In separate cohorts, we examined circulating lncExACT1 levels by ddPCR in plasma from patients with HF with preserved ejection fraction (HFpEF, n=18, EF=64.7±7.76%) and HF with reduced ejection fraction (HFrEF, n=16, EF=22.3±8.92%, p<10$^{-14}$) in comparison to plasma from patients without HF and structurally normal hearts who presented with supraventricular tachycardia (SVT, n=8, EF=60.8±2.3%). Circulating lncExACT1 increased 2.9-fold in plasma from HFrEF patients (p=0.032 vs SVT) and increased 3.4-fold in HFpEF patients (p=0.006 vs SVT) (FIG. 1E). Together these data underscore the potential clinical relevance of lncExACT1.

Example 2. lncExACT1 Overexpression Induces Pathological Cardiac Hypertrophy

Figure 2A:
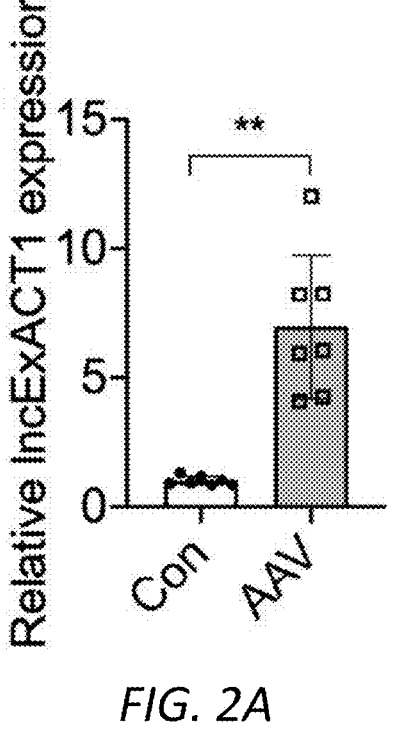
FIGS. 2A-I. lncExACT1 overexpression induces pathological cardiac hypertrophy. A. lncExACT1 expression in hearts from mice at 16 weeks after injection of control (Con) or AAV B. Heart weight (HW) to tibial length (TL) ratio. C. Lung weight (LW) to tibial length (TL) ratio. D. Fractional shortening (FS). E. Left ventricular end diastolic internal dimension (LVIDd). F. Relative wall thickness (RWT). G. Gene expressions of ANP, BNP, β/αMHC ratio, and PGC1α in the heart. H. Quantification of cardiomyocyte area from heart sections with wheat germ agglutinin (WGA) staining. I. Quantification of EdU (Green) and PCM1 (Red) double-positive cardiomyocytes from heart sections. *p<0.05, **p<0.01, Data are shown as mean±SEM.
Figure 2B:
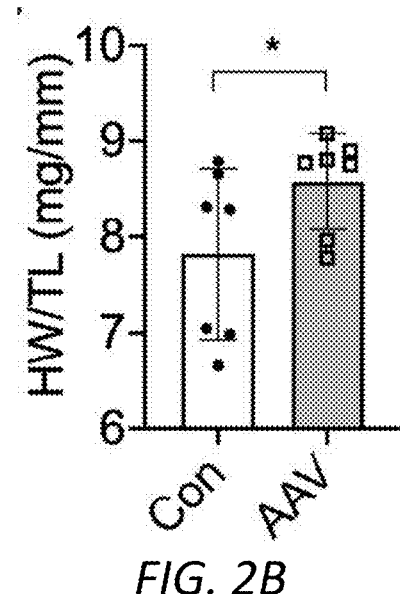
Figure 2C:
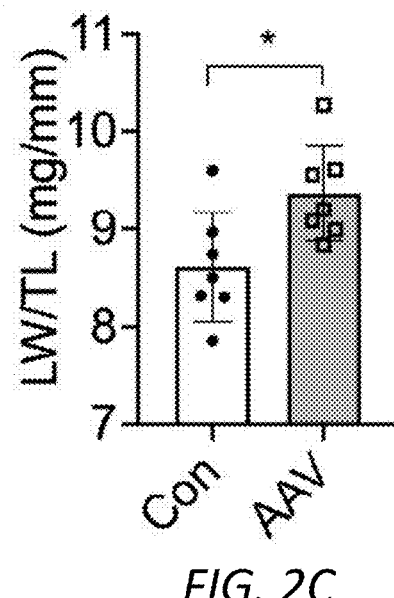
Figure 2D:
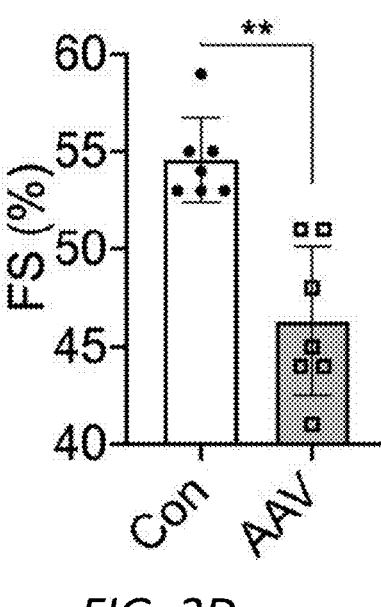
Figure 2E:
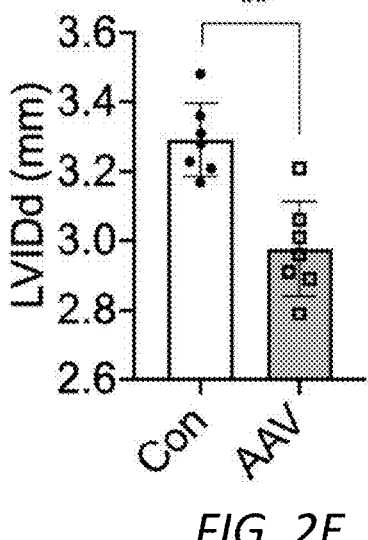
Figure 2F:
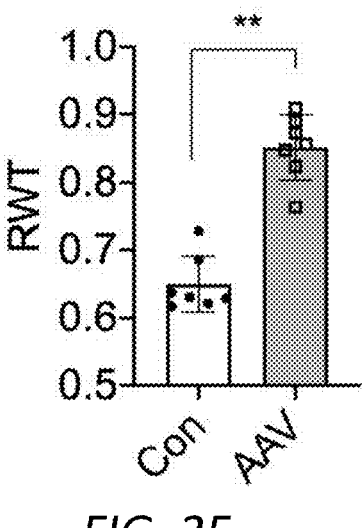
Figure 2G:
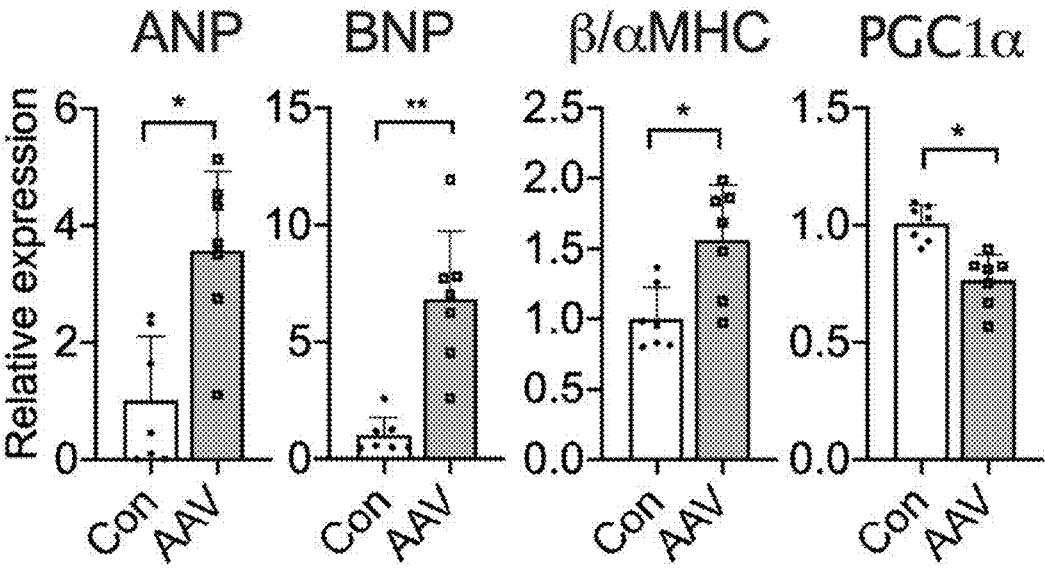
Figure 2H:
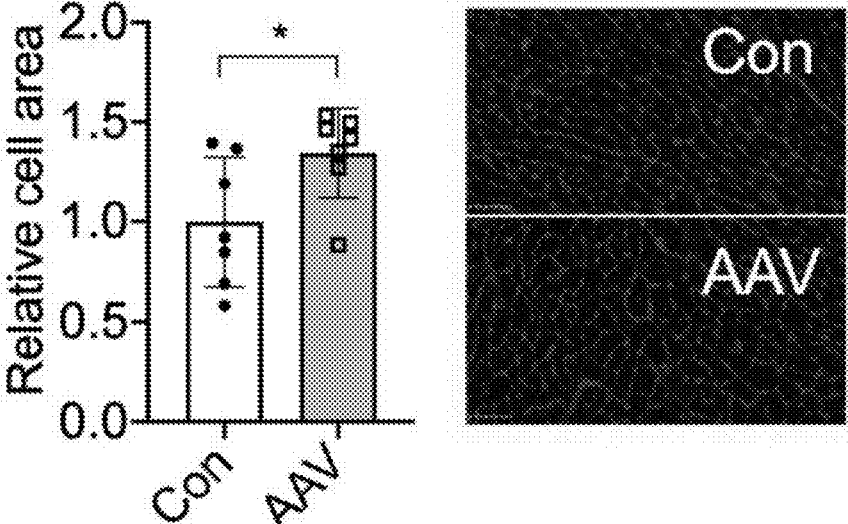
Figure 2I:
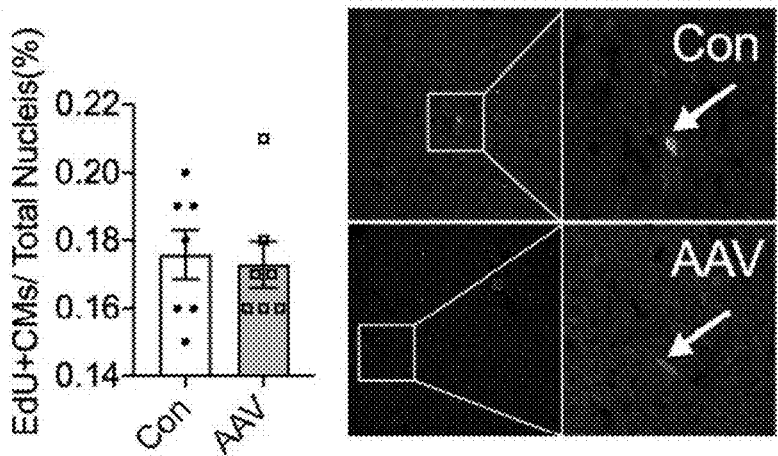
Figure 10A:
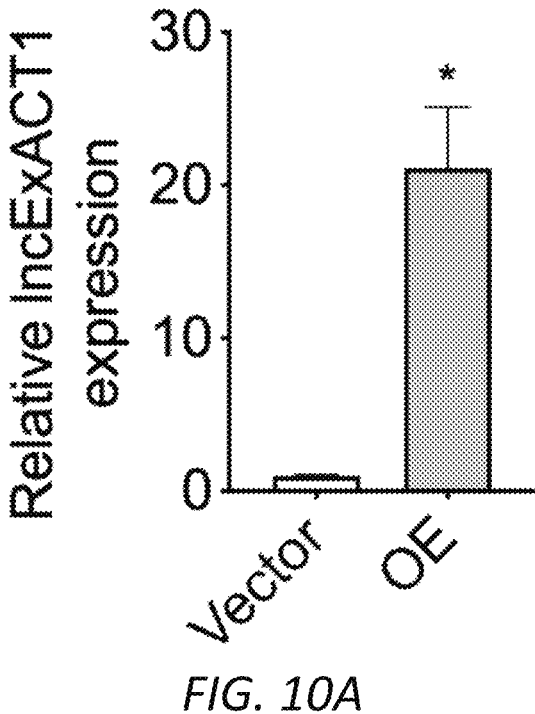
Figure 10B:
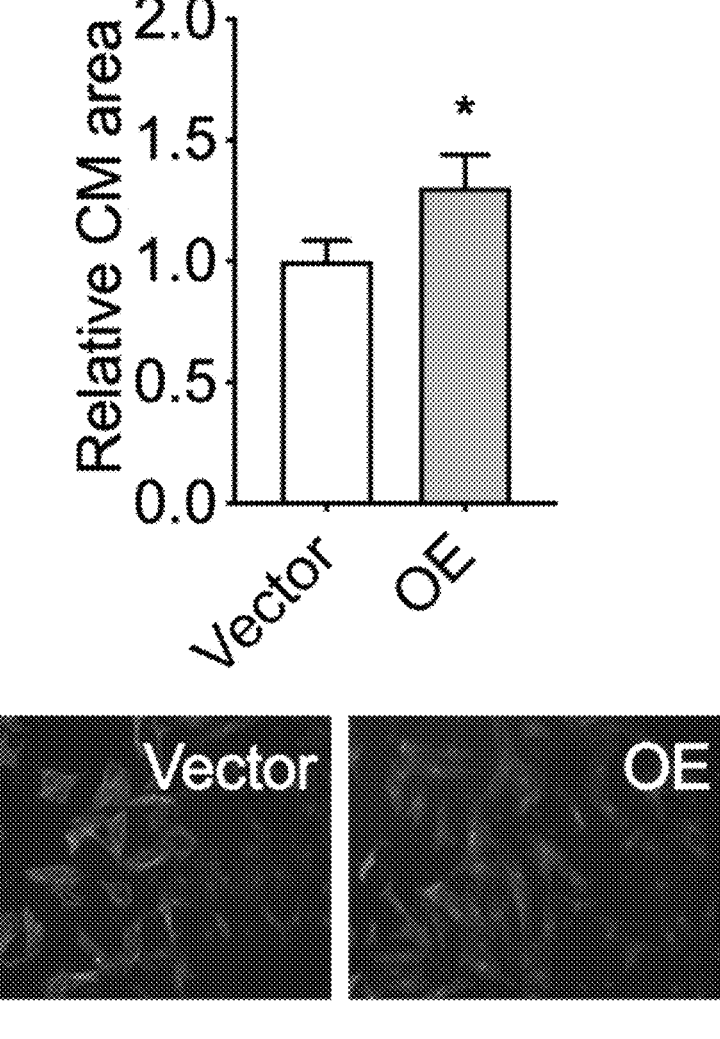

To examine the functional effects of lncExACT1, we expressed lncExACT1 in primary cardiomyocytes. Lentiviral expression of lncExACT1 increased cardiomyocyte size and induced a gene expression pattern characteristic of pathological hypertrophy including increased atrial natriuretic peptide (ANP), brain natriuretic peptide (BNP), β/α myosin heavy chain (MHC) ratio, CCAAT/Enhancer Binding Protein (C/EBP) β, and decreased peroxisome proliferator-activated receptor gamma coactivator (PGC)1α (FIGS. 10A-C). Overexpression of lncExACT1 did not alter cardiomyocyte proliferation but enhanced proliferation of non-CMs, predominantly made up of fibroblasts (FIGS. 10D-E). In vivo tail vein injection of a cardiotropic adeno-associated virus (AAV, 2*10$^{12}$ GC/mouse) encoding lncExACT1 driven by a cardiac-specific promoter increased cardiac lncExACT1 gene expression ~7-fold at 16 weeks in comparison to control vector-injected mice (FIG. 2A), which is similar to the increase seen in pathological hypertrophy and HF. AAV-mediated lncExACT1 expression was sufficient to increase both heart (HW/TL) (FIG. 2B), and lung weight relative to tibial length (LW/TL) (FIG. 2C), reduce fractional shortening (FS) and chamber size, and increase relative wall thickness (FIGS. 2D-F and Table 1). These changes were associated with a gene expression pattern consistent with pathological hypertrophy as evidenced by increased ANP, BNP, β/αMHC ratio and reduced PGC1α (FIG. 2G). Moreover, induction of lncExACT1 increased cardiomyocyte size but did not affect markers of cardiomyocyte proliferation (FIG. 2H-I). These data indicate that overexpression of lncExACT1 at levels comparable to those seen after TAC is sufficient to induce pathological cardiac hypertrophy and heart failure.

TABLE 1

| Echocardiography analysis of cardiac function of mice 16 weeks after AAV infection | | |
| --- | --- | --- |
| | Con (Male, n = 7) | AAV (Male, n = 7) |
| IVSd (mm) | 1.01 ± 0.04 | 1.29 ± 0.04* |
| IVSs (mm) | 1.79 ± 0.05 | 1.98 ± 0.04* |
| LVIDd (mm) | 3.28 ± 0.04 | 2.99 ± 0.06* |
| LVIDs (mm) | 1.52 ± 0.05 | 1.45 ± 0.02 |
| LVPWd (mm) | 1.14 ± 0.03 | 1.36 ± 0.06* |
| LVPWs (mm) | 1.81 ± 0.03 | 2.03 ± 0.09* |
| FS (%) | 54.59 ± 0.81 | 46.30 ± 1.44* |

IVSs: systolic interventricular septum; IVSd diastolic interventricular septum; LVIDd: left ventricular end diastolic internal dimension; LVIDs: left ventricular end systolic dimension; LVPWd: left ventricular end diastolic posterior wall; LVPWs: left ventricular end systolic posterior wall dimension; FS (%): fractional shortening.
*p < 0.05.
Data are shown as mean ± SEM.

Example 3. lncExACT1 Inhibition Induces Physiological Cardiac Hypertrophy

Figure 3A:
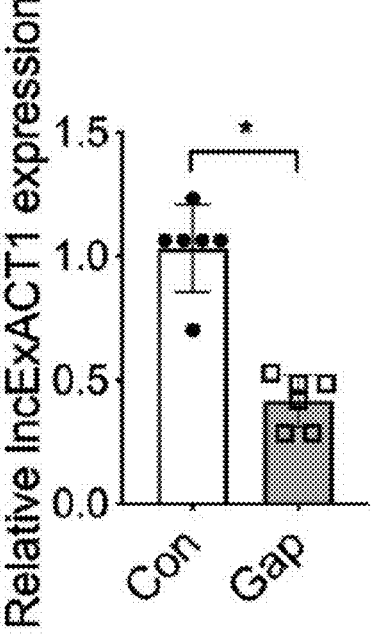
FIGS. 3A-J. lncExACT1 inhibition induces physiological cardiac hypertrophy. A. lncExACT1 expression in the hearts from mice at 2 weeks after injection of control (Con) or LNA-GapmeR (Gap). B. Heart weight (HW) to tibial length (TL) ratio. C. Lung weight (LW) to tibial length (TL) ratio. D. Fractional shortening (FS). E. Left ventricular end diastolic internal dimension (LVIDd). F. Relative wall thickness (RWT). G. Gene expressions of ANP, BNP, β/αMHC ratio, and PGC1α in the heart. H. Quantification of cardiomyocyte area from heart sections with wheat germ agglutinin (WGA) staining. I. Quantification of EdU (Green) and PCM1 (Red) double positive cardiomyocytes from heart sections. J. Relative lncExACT1 expression in 293T cells transfected with control or lncExACT1-GapmeR (Gap). *p<0.05, **p<0.01, Data are shown as mean±SEM.
Figure 3B:
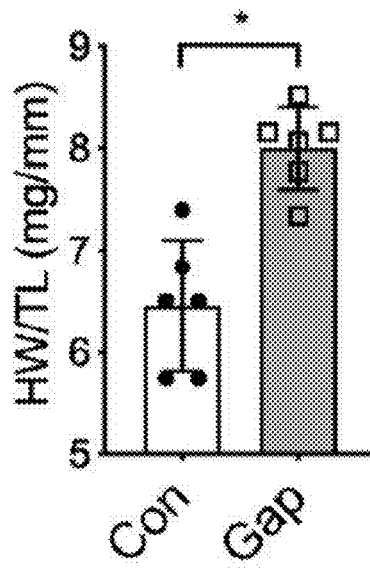
Figure 3C:
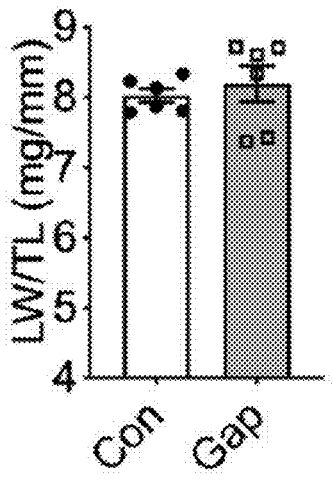
Figure 3D:
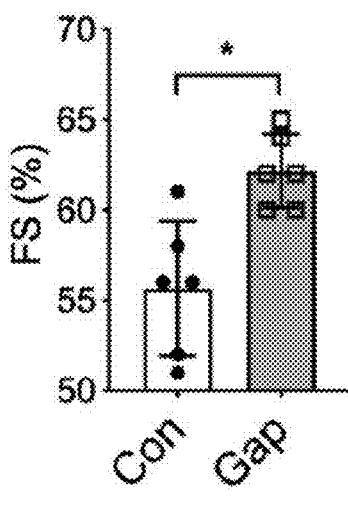
Figure 3E:
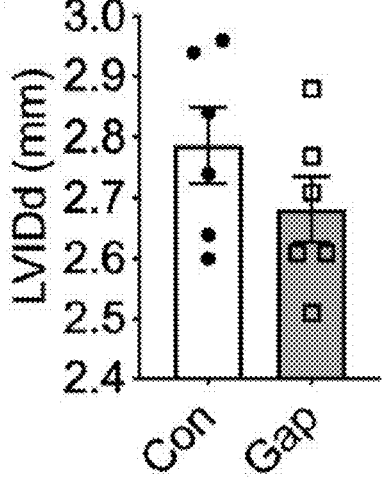
Figure 3F:
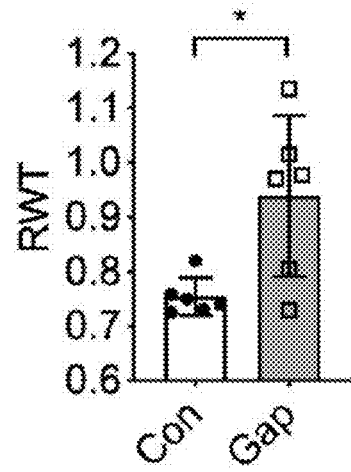
Figure 3G:
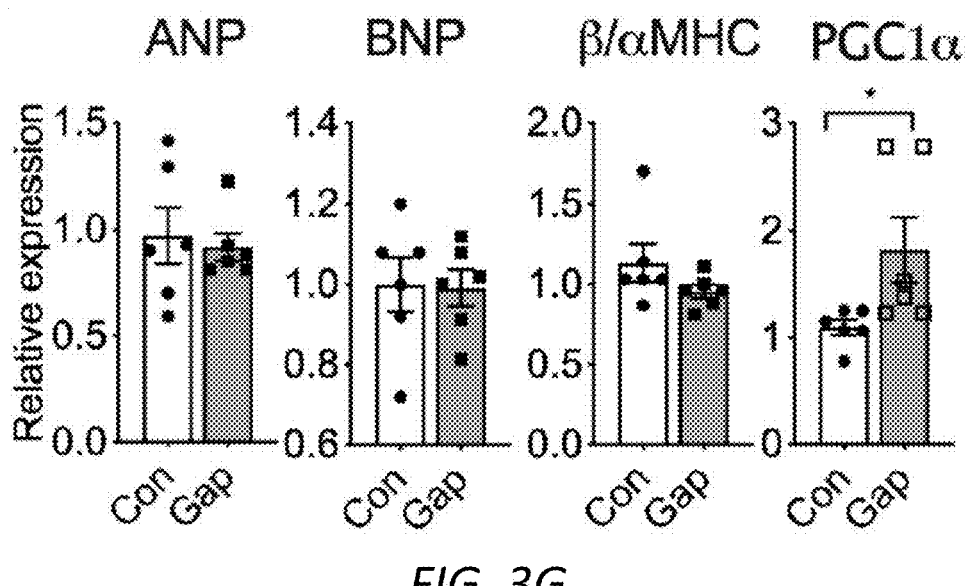
Figure 3H:
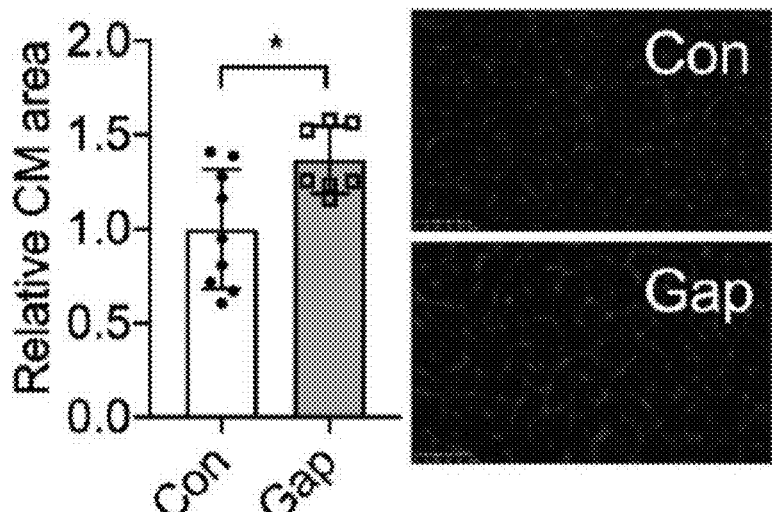
Figure 3I:
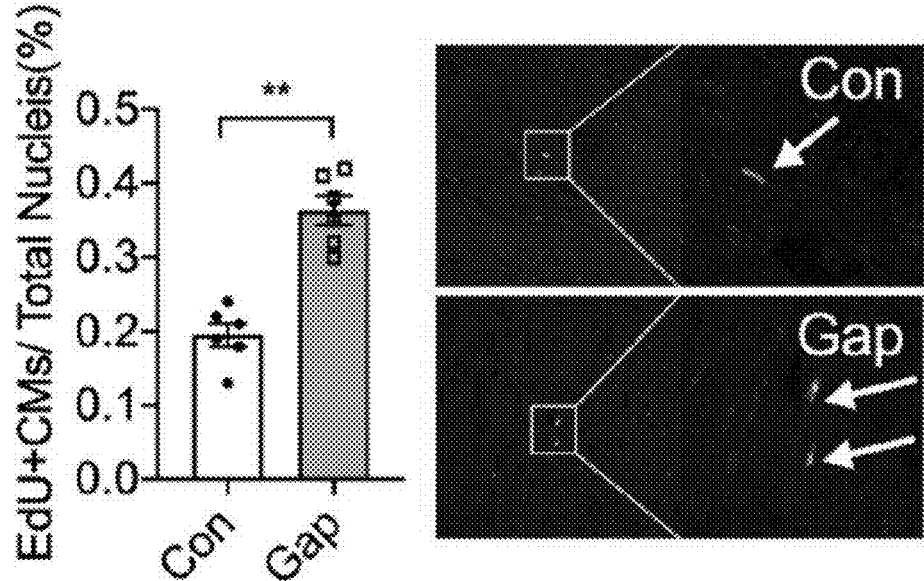
Figure 3J:
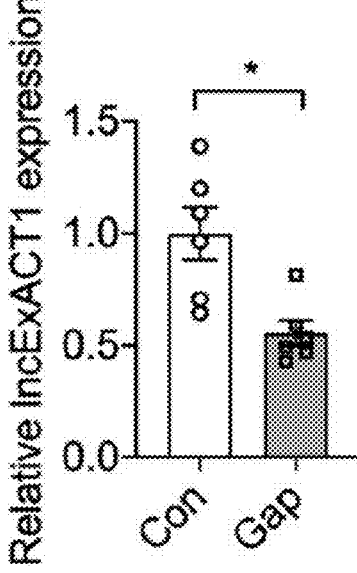
Figure 11A:
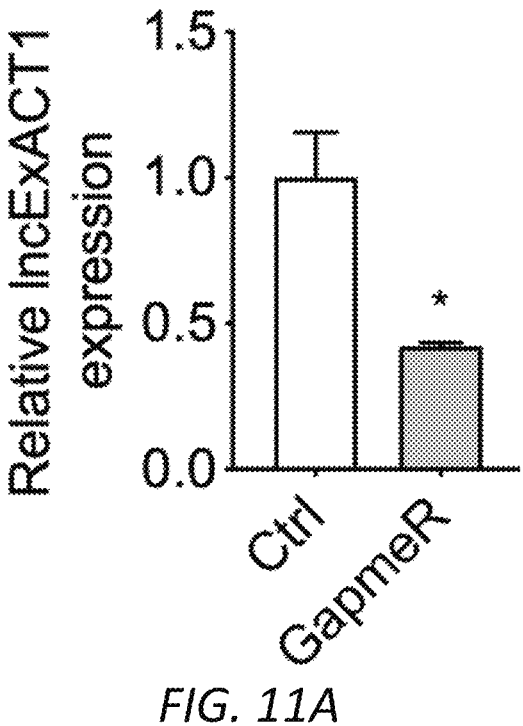
FIGS. 11A-E. Inhibition of lncExACT1 induces physiological hypertrophy in cardiomyocytes in vitro. A. Relative lncExACT1 expression in NRVMs transfected with scramble control (Ctrl) or LNA-GapmeR targeting lncExACT1 (GapmeR). B. Quantification of cardiomyocyte (CM) area for NRVMs stained with α-Actinin (red) and DAPI (blue). C. Relative mRNA expression of ANP, BNP, β/αMHC ratio, PGC1α, and C/EBPβ. D-E. Quantifications of EdU-positive CMs and non-CMs. n=3 independent replicates per group. *p<0.05 vs Ctrl. Data are shown as mean±SEM.
Figure 11B:
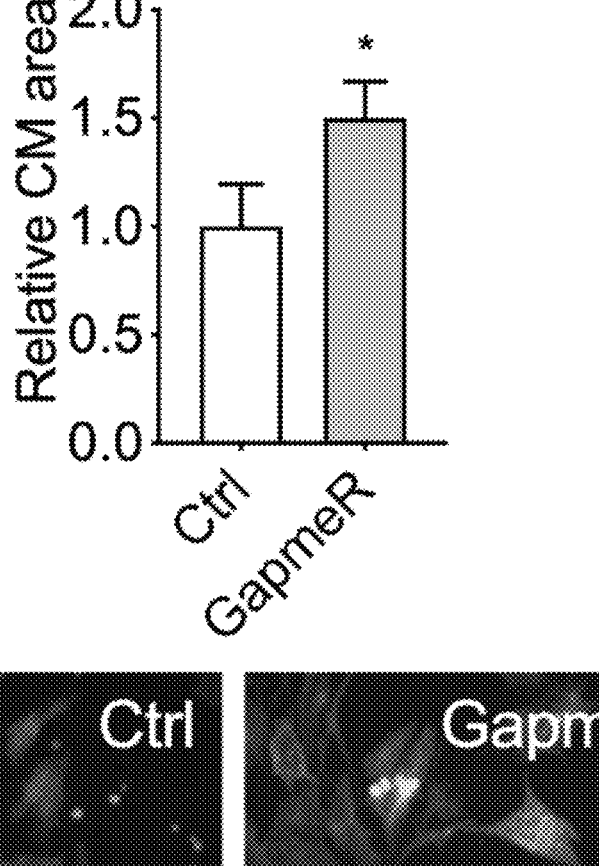
Figure 11C:
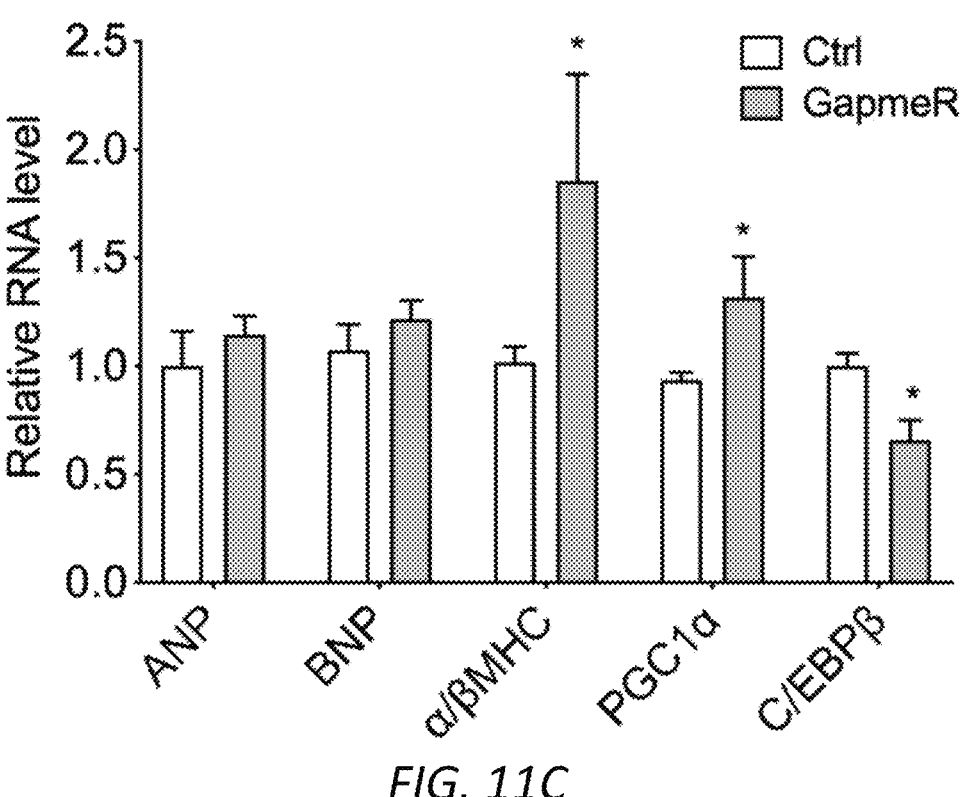
Figure 11D:
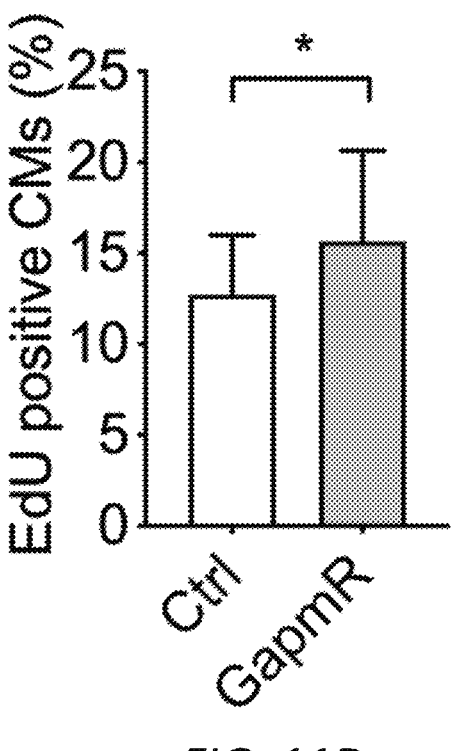
Figure 11D:
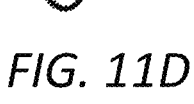
Figure 11E:
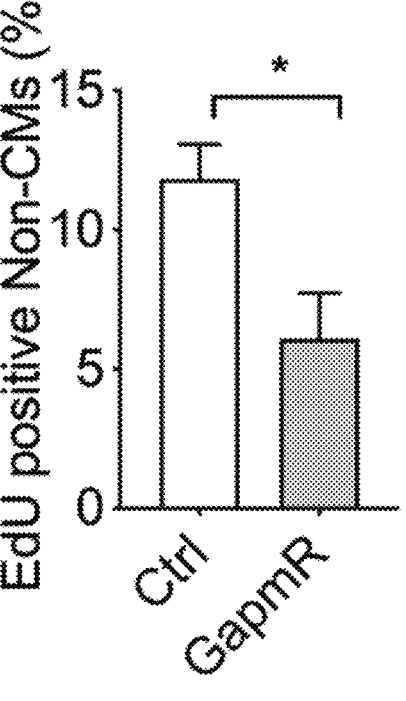

Since lncExACT1 is reduced in the exercised heart, we next examined whether knockdown of lncExACT1 could mimic exercise-induced physiological cardiac growth. In primary cardiomyocytes, transfection with a locked nucleic acid (LNA) antisense oligonucleotide (GapmeR) specific to lncExACT1 led to a 55% reduction in transcript levels (FIG. 11A). lncExACT1 knockdown also increased cardiomyocyte size as with overexpression but induced a gene expression pattern consistent with physiological hypertrophy, including increased PGC1α, and decreased β/αMHC ratio and C/EBPβ, with no change in ANP or BNP expression (FIGS. 11B-C). Moreover, inhibition of lncExACT1 enhanced markers of proliferation in cardiomyocytes while suppressing these markers in non-cardiomyocytes (FIGS. 11D-E). In vivo injection of lncExACT1 GapmeR for 2 weeks reduced cardiac lncExACT1 expression by ~50%, similar to the reduction seen in exercised hearts (FIG. 3A). Inhibition of lncExACT1 increased HW/TL (FIG. 3B) without affecting LW/TL (FIG. 3C), improved cardiac function (FIG. 3D), and increased relative wall thickness (FIG. 3E and Table 2) without a significant change in chamber dimension (FIG. 3F). Moreover, inhibition of lncExACT1 induced a gene expression pattern most consistent with physiological hypertrophy with no change in ANP, BNP, or β/αMHC ratio but an increase in PGC1α (FIG. 3G). Inhibition of lncEx-ACT1 increased cardiomyocyte size (FIG. 3H) to a degree comparable to that seen with lncExACT1 overexpression (FIG. 2H). However, lncExACT1 inhibition also increased markers of cardiomyocyte proliferation as evidenced by increased 5-ethynyl-2'-deoxyuridine (EdU) in pericentriolar material 1 (PCM1) positive cells (FIG. 3I). Taken together these data demonstrate that while lncExACT1 is sufficient to cause pathological cardiac hypertrophy and HF, lncExACT1 also acts as an inhibitor of physiological cardiac growth and its inhibition is sufficient to induce physiological cardiac hypertrophy and other cardiac exercise phenotypes. In order to see if GapmeR was effective in inhibiting human lncEx-ACT1, GapmeR specifically targeting human lncExACT1 was synthesized and transfected into human embryonic kidney 293T cells. At 48 hours, expression of lncExACT1 was reduced by 48% (FIG. 3J), suggesting that GapmeR was sufficient to inhibit human lncExACT1.

TABLE 2

Echocardiography analysis of cardiac function of mice 2 weeks after GapmeR injection

|  | Con (Male, n = 6) | GapmeR (Male, n = 6) |
|---|---|---|
| IVSd (mm) | 0.97 ± 0.04 | 1.15 ± 0.05 |
| IVSs (mm) | 1.55 ± 0.05 | 1.80 ± 0.04* |
| LVIDd (mm) | 2.79 ± 0.06 | 2.68 ± 0.05 |
| LVIDs (mm) | 1.28 ± 0.17 | 1.23 ± 0.07 |
| LVPWd (mm) | 1.16 ± 0.03 | 1.34 ± 0.08* |
| LVPWs (mm) | 21.97 ± 0.06 | 2.07 ± 0.05* |
| FS (%) | 55.81 ± 1.88 | 62.18 ± 1.11* |

IVSs: systolic interventricular septum; IVSd diastolic interventricular septum; LVIDd: left ventricular end diastolic internal dimension; LVIDs: left ventricular end systolic dimension; LVPWd: left ventricular end diastolic posterior wall; LVPWs: left ventricular end systolic posterior wall dimension; FS (%): fractional shortening.
*p < 0.05.
Data are shown as mean ± SEM.

Figures 4A, 4B, 4C, 4D, 4E:
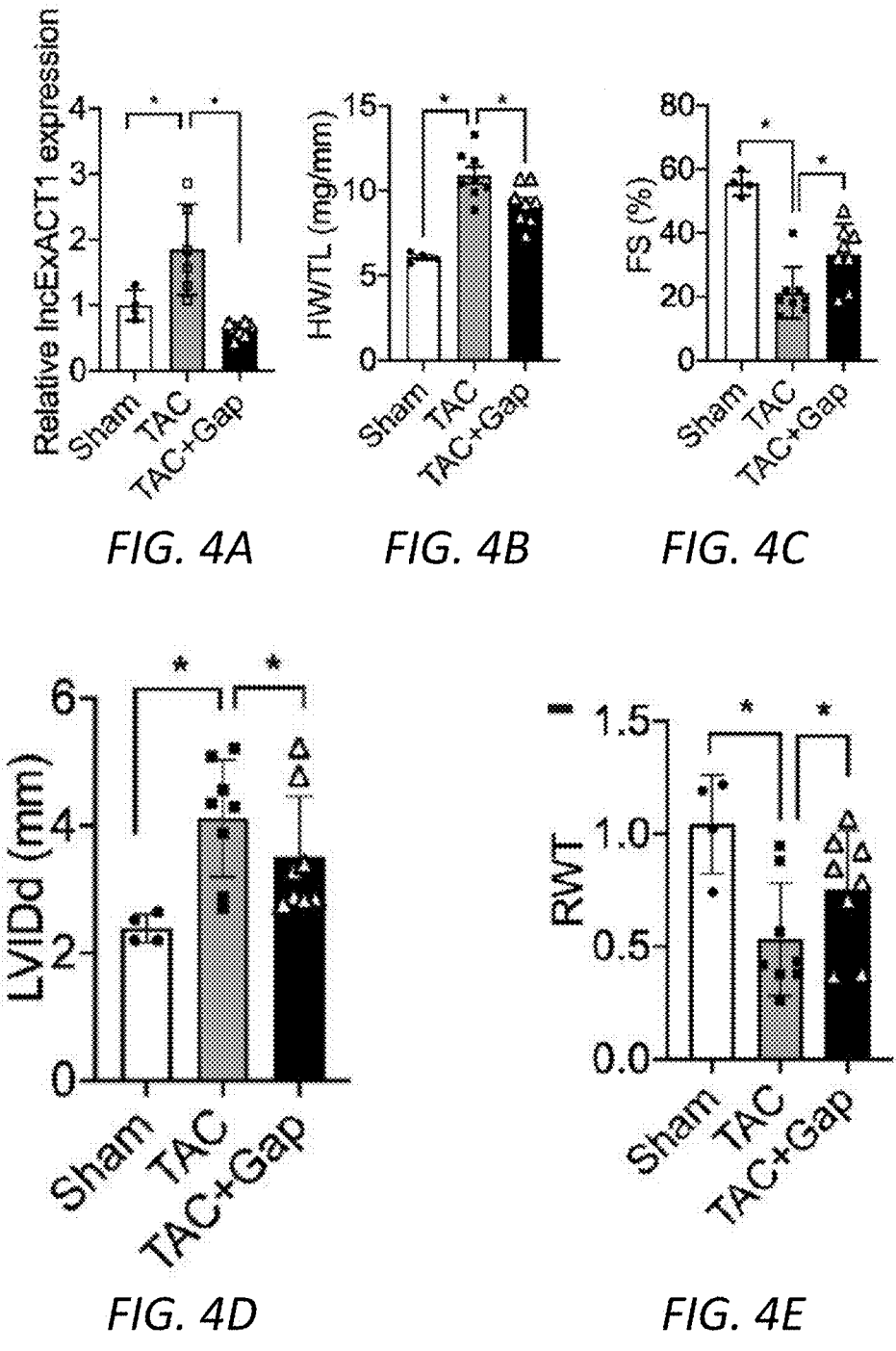
FIGS. 4A-J. lncExACT1 inhibition protects the heart against pathological hypertrophy and ischemia reperfusion injury. A. lncExACT1 expression in hearts from mice subjected to sham operation (Sham), transverse aortic constriction (TAC), or TAC with LNA-GapmeR injection (TAC+Gap). B. Heart weight (HW) to tibial length (TL) ratio. C. Fractional shortening (FS). D. Left ventricular end diastolic internal dimension (LVIDd). E. Relative wall thickness (RWT). F. Gene expression of ANP, BNP, β/αMHC ratio, and PGC1α in the heart. G. Quantification of fibrosis formation from heart sections with masson trichrome staining H. Quantification of cardiomyocyte area from heart sections with wheat germ agglutinin (WGA) staining. I. Quantification of Ki67 and PCM1 double positive cardiomyocytes from heart sections. J. FS in mice receiving sham-operation, or ischemia reperfusion (IR), or IR with lncExACT1 GapmeR. *p<0.05, **p<0.01; in I *p<0.05 vs. Sham, #p<0.05 vs. TAC. Data are shown as mean±SEM.
Figure 4F:
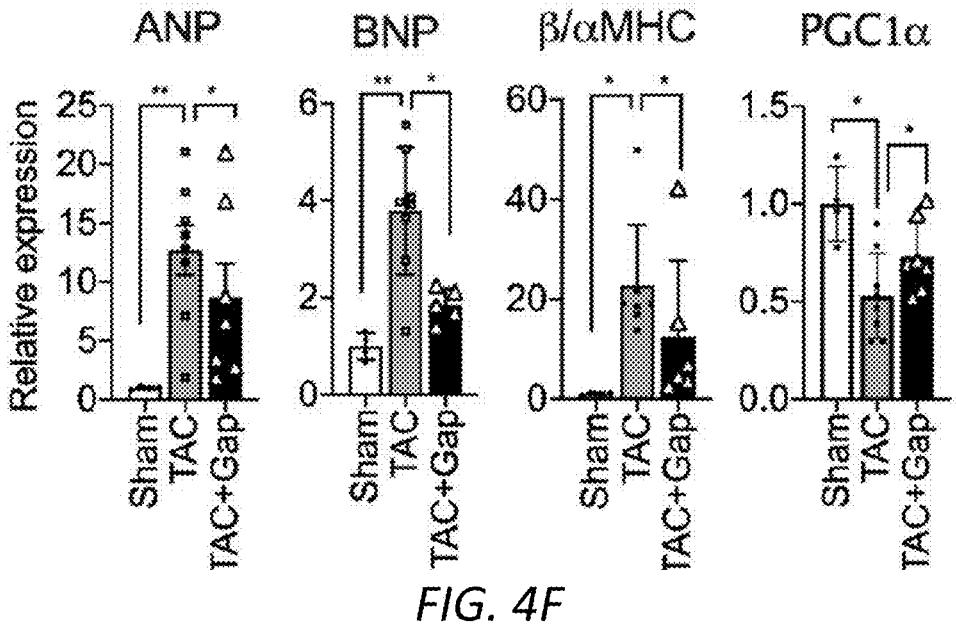
Figure 4G:
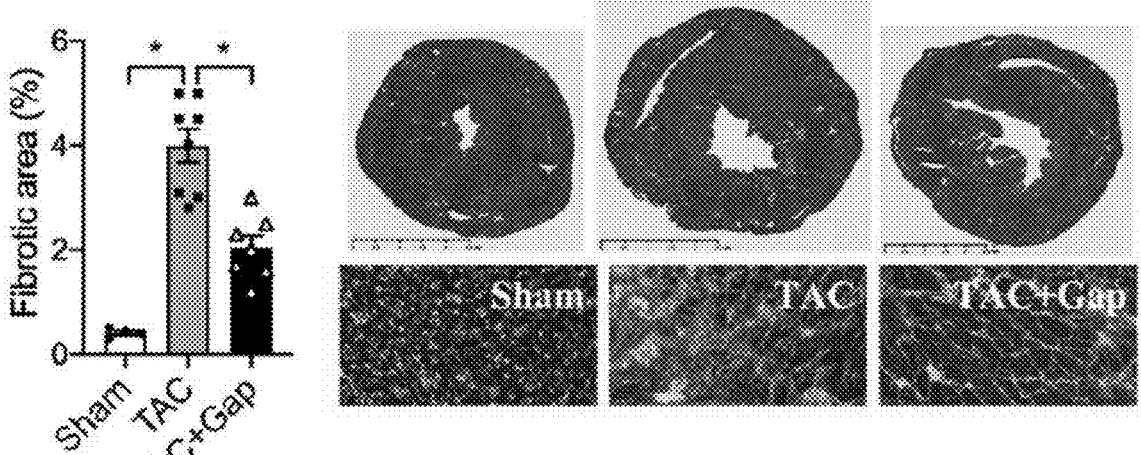
Figure 4H:
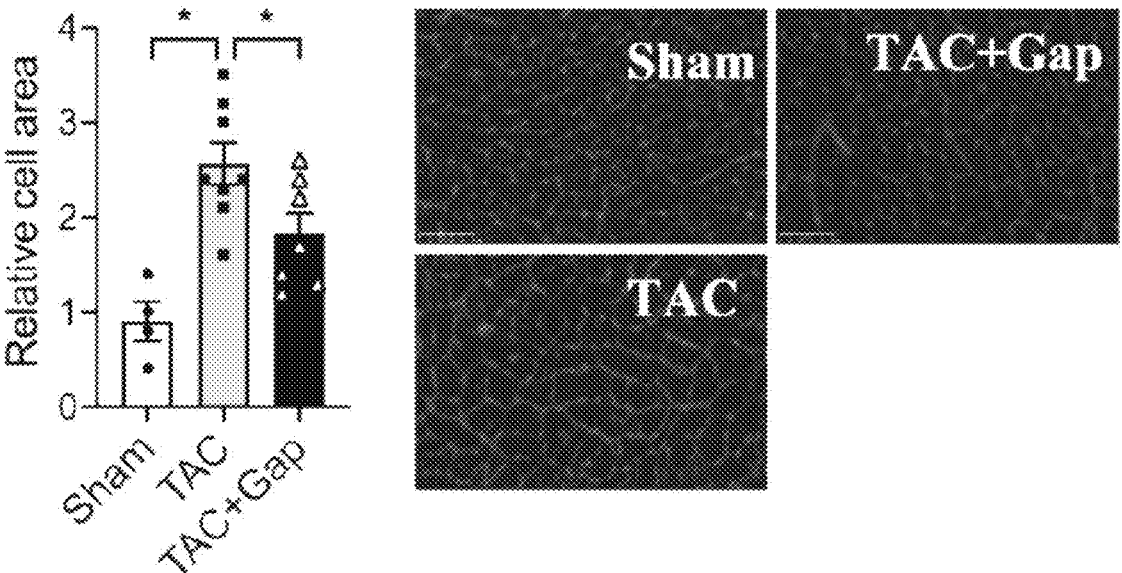
Figure 4I:
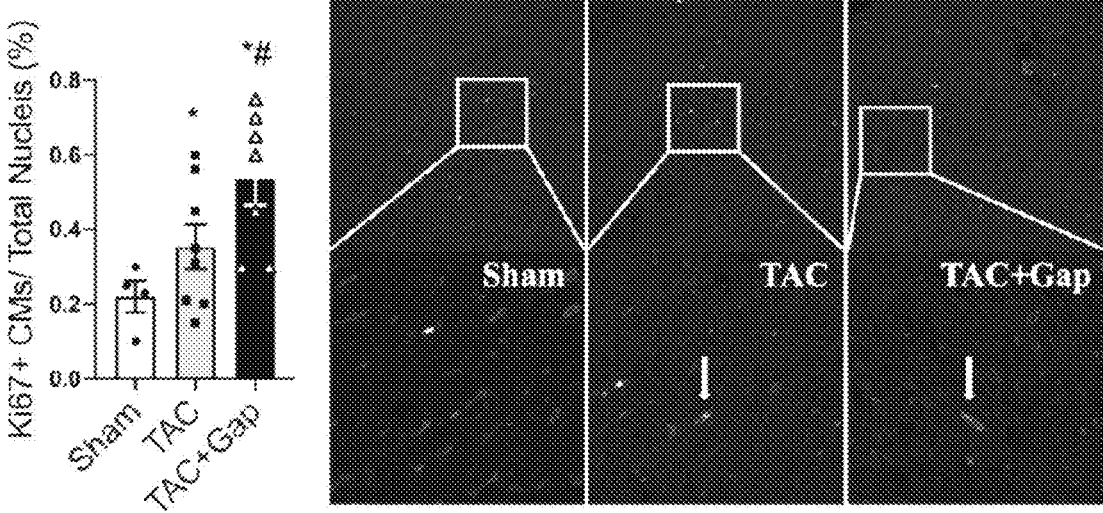

Example 4. lncExACT1 Inhibition Protects the Heart Against Adverse Remodeling and Ischemia Reperfusion Injury Given that exercise protects the heart against pathological stress[27-29], we asked whether the physiological cardiac growth state induced by lncExACT1 inhibition was also protective against heart failure induced by pressure-overload (TAC). Injection of mice with lncExACT1-specific GapmeR for 6 weeks completely blocked the TAC-induced increase in cardiac lncExACT1 in comparison to control GapmeR-injected mice (FIG. 4A). lncExACT1 inhibition also mitigated the TAC-induced increase in heart weight (FIG. 4B), and improved cardiac function (FIG. 4C), while reducing chamber dilatation and wall thinning (FIGS. 4D-E and Table 3). Inhibition of lncExACT1 also reduced cardiac fibrosis and cardiomyocyte size after TAC (FIG. 4G-H) while partially reversing pathological gene expression (FIG. 4F). Interestingly, Ki67, a marker of proliferation, was increased in cardiomyocytes after TAC and was further increased by lncExACT1 inhibition (FIG. 4I). These results indicate that inhibition of lncExACT1 is sufficient to protect the heart against pathological hypertrophy, fibrosis, and cardiac dysfunction.

Figure 4J:
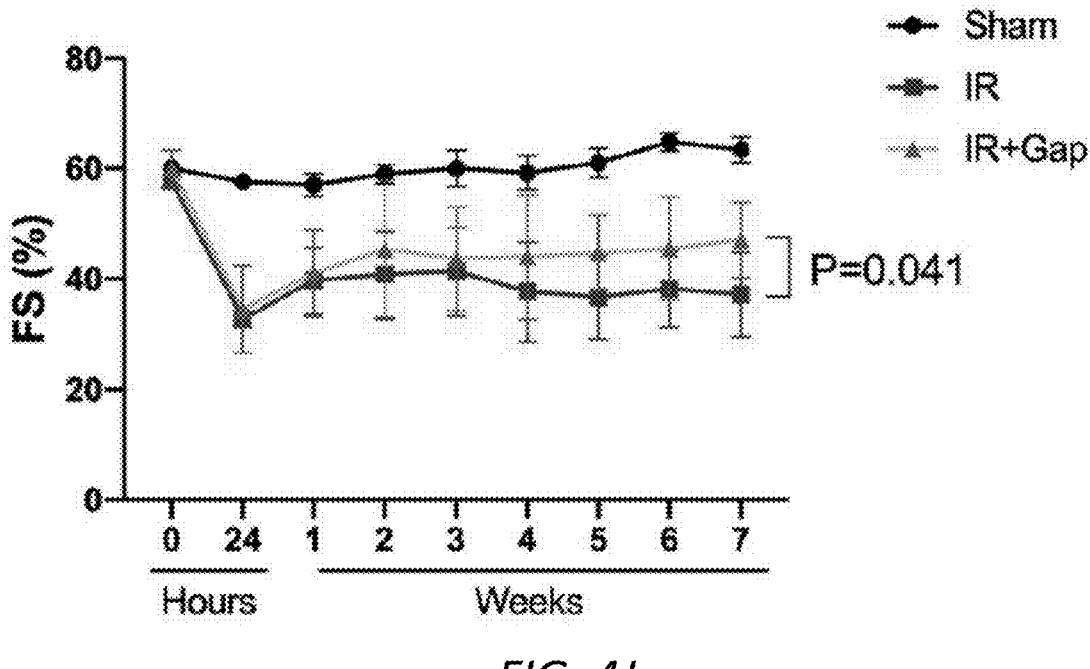

Exercise reduces adverse remodeling and attenuates cardiac dysfunction after infarction[30, 31]. Thus, we examined whether lncExACT1 inhibition is sufficient to mimic the cardioprotective effects of exercise against myocardial ischemic injury. Ischemia reperfusion (IR) injury was induced by subjecting mice to 30 minutes of left coronary artery ligation followed by reperfusion. Immediately after ischemia, one group of mice received a subcutaneous injection of lncExACT1-specific GapmeR, while a second group received scrambled-GapmeR as control. Fractional shortening at 7 weeks was higher in the IR+GapmeR group than in the IR group (FIG. 4J). This result indicates that inhibition of lncExACT1 is sufficient to protect the heart against IRI.

TABLE 3

Echocardiography analysis of cardiac function of mice 6 weeks after TAC

|  | Con (Male, n = 6) | TAC (Male, n = 6) | TAC + GapmeR (Male, n = 6) |
|---|---|---|---|
| IVSd (mm) | 1.24 ± 0.13 | 0.98 ± 0.07* | 1.22 ± 0.08# |
| IVSs (mm) | 1.51 ± 0.04 | 1.37 ± 0.08* | 1.69 ± 0.07# |
| LVIDd (mm) | 2.39 ± 0.11 | 4.12 ± 0.33* | 3.51 ± 0.34*# |
| LVIDs (mm) | 1.05 ± 0.08 | 3.20 ± 0.34* | 2.41 ± 0.36*# |
| LVPWd (mm) | 1.23 ± 0.07 | 1.02 ± 0.08* | 1.23 ± 0.07# |
| LVPWs (mm) | 1.26 ± 0.03 | 1.01 ± 0.03* | 1.21 ± 0.05# |
| FS (%) | 55.50 ± 1.85 | 21.25 ± 2.85* | 33.23 ± 3.36*# |

IVSs: systolic interventricular septum; IVSd diastolic interventricular septum; LVIDd: left ventricular end diastolic internal dimension; LVIDs: left ventricular end systolic dimension; LVPWd: left ventricular end diastolic posterior wall; LVPWs: left ventricular end systolic posterior wall dimension; FS (%): fractional shortening.
*p < 0.05. vs Con;
p < 0.05 vs TAC.
Data are shown as mean ± SEM.

Figure 5A:
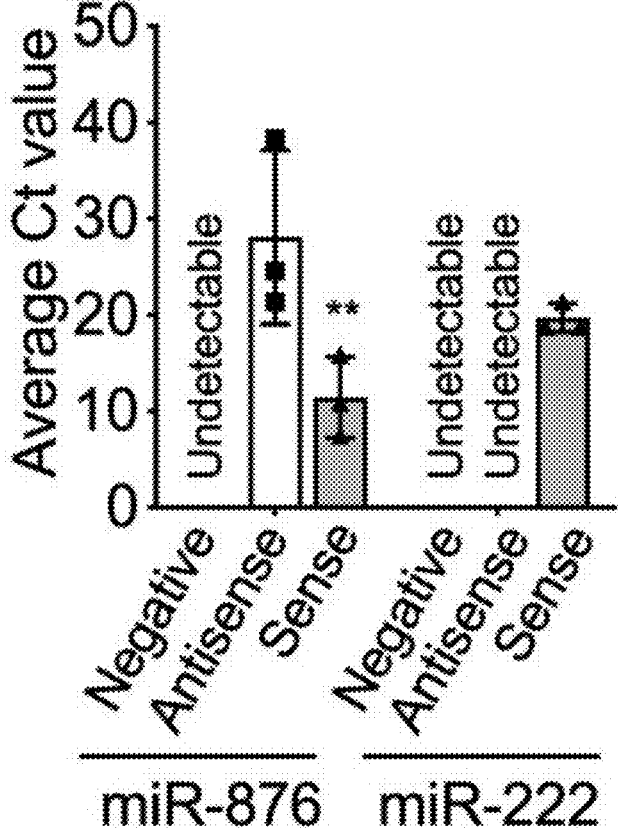
FIGS. 5A-D. lncExACT1 binds miR-222. A. Ct value of QPCR for miR-876 and miR-222 in pulldown with negative control (negative) or probes targeting antisense or sense sequence of lncExACT1. B. Luciferase activity of 293T cells transfected with wildtype (wt) or mutant (mut) vector with or without miR-876 or miR-222 mimic. C. Gene expression of ANP, BNP, β/αMHC ratio, PGC1α, and C/EBPβ in neonatal rat cardiomyocytes (NRVMs) transfected with lncExACT1 LNA-GapmeR and/or miR-222 inhibitor. D. Gene expression of ANP, BNP, β/αMHC ratio, PGC1α, and C/EBPβ in neonatal rat cardiomyocytes (NRVMs) transfected with lncExACT1 overexpression (OE) and/or miR-222 mimic. *p<0.05, **p<0.01; in C, *p<0.05 vs. Control, #p<0.05 vs. lncExACT1 KD. Data are shown as mean±SEM.
Figure 5B:
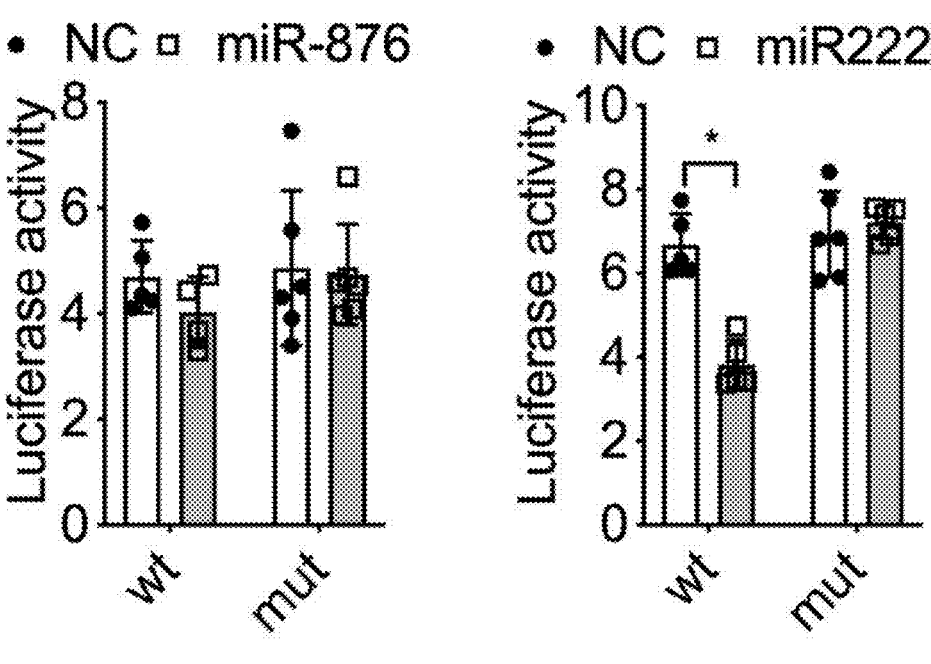
Figure 12B:
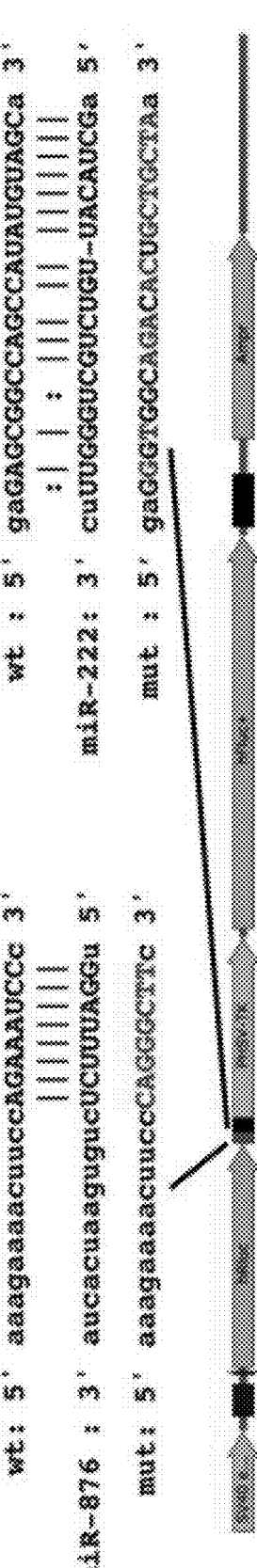

Example 5. lncExACT1 Binds miR-222 lncRNAs can exert their effects by acting as competitive endogenous RNAs (ceRNAs) that bind miRNAs to inhibit their actions. Bioinformatic analyses (starbase.sysu.edu.cn) identified five miRNAs as potentially binding lncExACT1 (FIG. 12A). We examined which of these bound lncExACT1 in primary cardiomyocytes by QPCR after pulldown of biotinylated probes specific for the sense or anti-sense strands of lncExACT1. Only miR-876-5p and miR-222-3p demonstrated detectable binding to lncExACT1. miR-876-5p, but not miR-222-3p, also bound the lncExACT1 anti-sense sequence though at a lower level (FIG. 5A). Sequences corresponding to the predicted wild-type or mutated miRNA binding sites of lncExACT1 were inserted 3' of a luciferase reporter and co-transfected into cardiomyocytes with the related miRNA, miR-876-5p or miR-222-3p (FIG. 12B). The miR-222-3p mimic reduced luciferase activity of the construct with wild-type (wt) but not mutated (mut) putative miR-222 binding sites. In contrast, mutation of the binding site did not affect luciferase activity after transfection with miR-876-5p (FIG. 5B). Together these findings suggest that lncExACT1 binds miR-222-3p, which we previously demonstrated is necessary for exercise-induced cardiac growth[12].

Figure 5C:
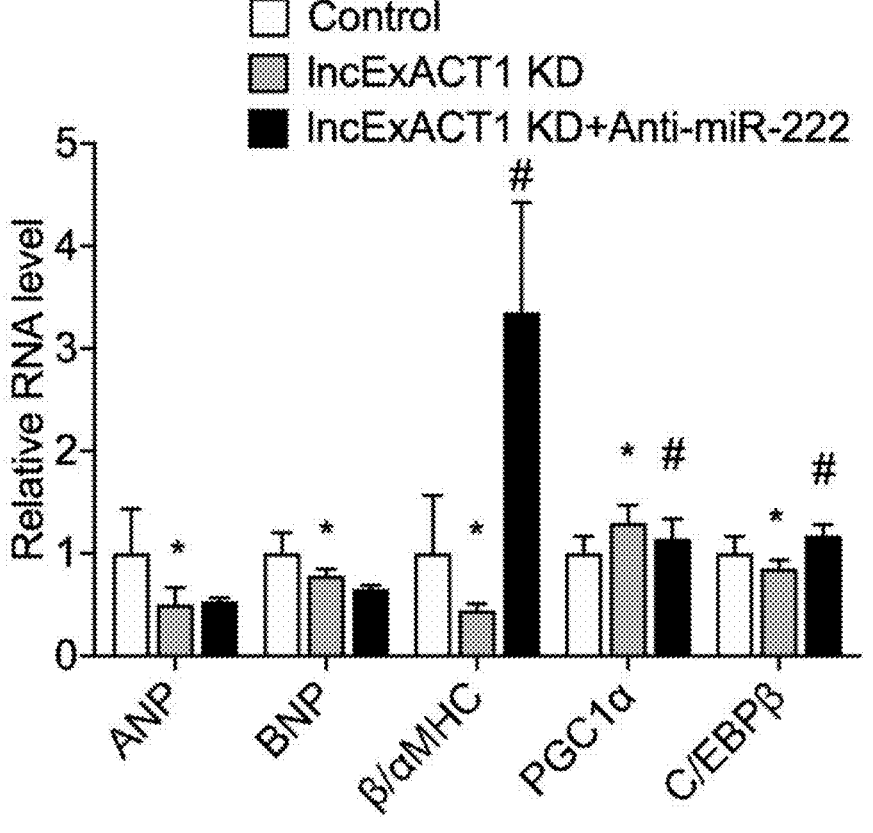
Figure 5D:
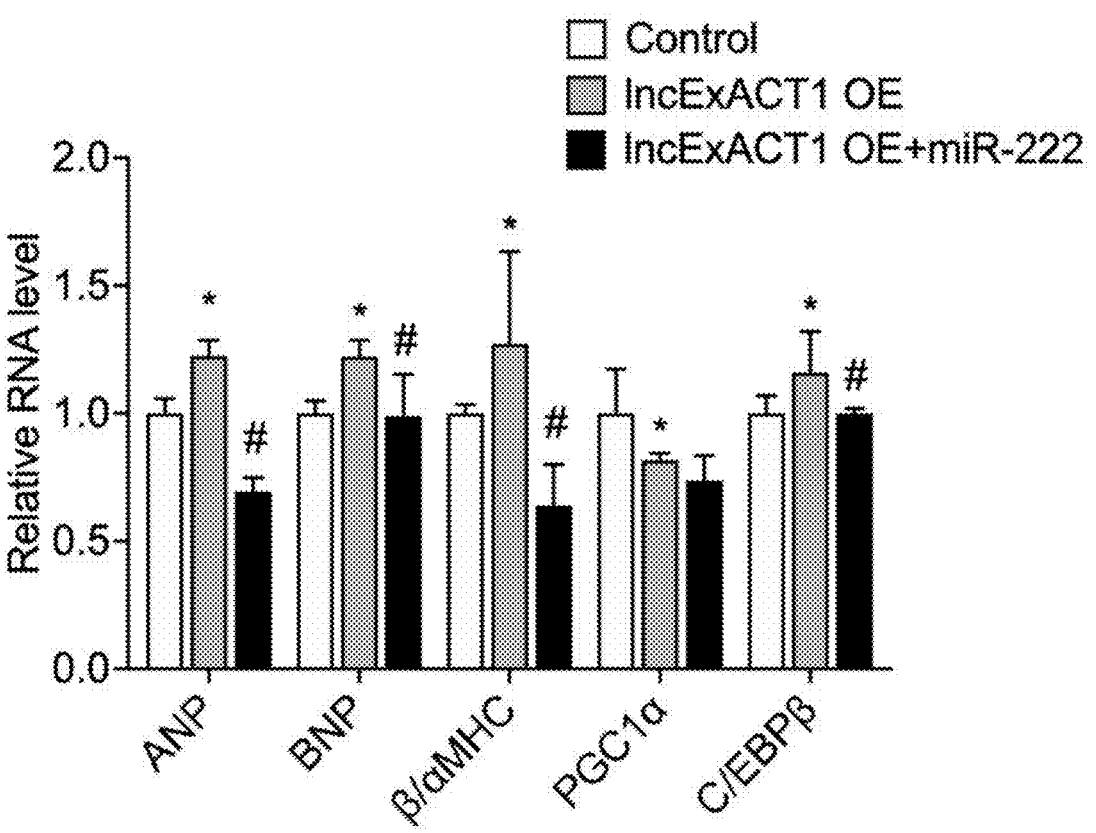

To determine if miR-222 contributes to the effects of lncExACT1, we examined the effects of combining miR-222 knockdown or overexpression with manipulation of lncExACT1 expression in primary cardiomyocytes. Inhibition of lncExACT1 induced a physiological cardiac hypertrophy gene expression pattern, as evidenced by reduced ANP, BNP, and β/αMHC ratio, increased PGC1α, and reduced C/EBPβ, and this pattern was partially reversed by miR-222 inhibition (FIG. 5C). Consistent with this, overexpression of lncExACT1 induced a pathological cardiac hypertrophy gene expression pattern, which was largely reversed by overexpression of miR-222 (FIG. 5D). These results suggest that lncExACT1 confers its effects, in part, by acting as a ceRNA for miR-222.

Example 6. lncExACT1 Regulates DCHS2 and Hippo Signaling

Figure 6A:
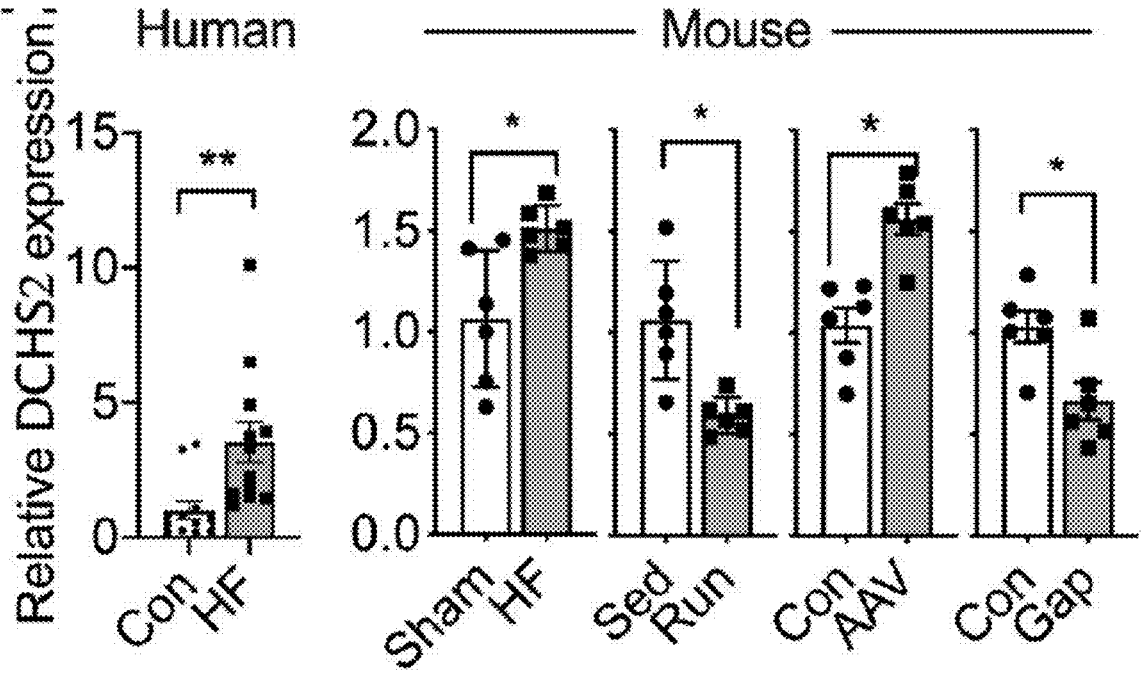
Figure 6B:
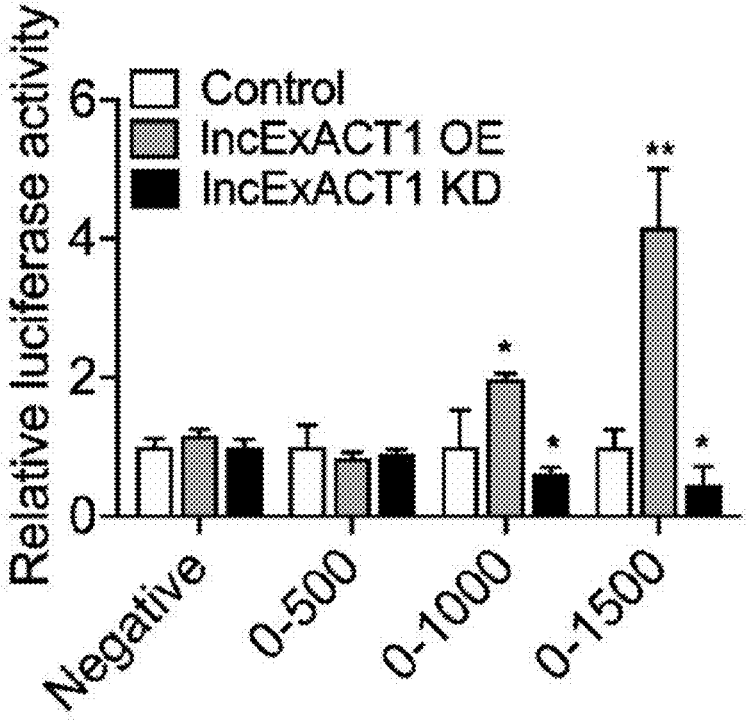
Figure 13A:
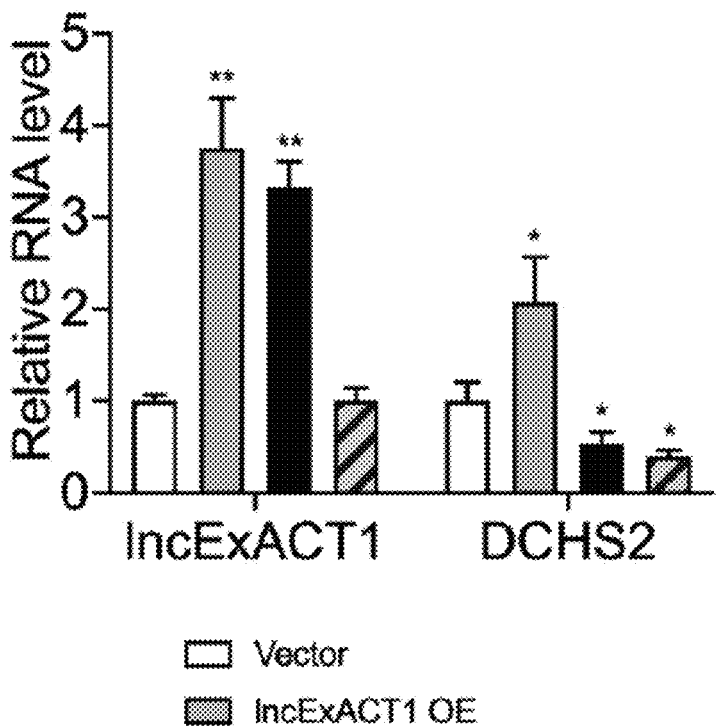
FIGS. 13A-H. lncExACT1 regulates DCHS2 in cardiac hypertrophy. A. Relative expression of lncExACT1 and DCHS2 transcripts in NRVMs with lncExACT1 overexpression (OE) in the presence or absence of DCHS2 siRNA (KD). B. Relative mRNA expression of lncExACT1 and DCHS2 in NRVMs with lncExACT1 inhibition (KD) in the presence or absence of DCHS2 overexpression (OE). C-D. Relative DCHS2 transcript levels in NRVMs with DCHS2 siRNA (KD) or DCHS2 overexpression using CRISPR/dCAS9 system with single guide RNA (sgRNA). E. Relative mRNA expression of ANP, BNP, β/αMHC ratio, PGC1α, and C/EBPβ in NRVMs with DCHS2 overexpression (sgRNA). F-G. Quantification of cell size and EdU positive in NRVMs with DCHS2 overexpression (sgRNA). H. Relative mRNA expression of ANP, BNP, β/αMHC ratio, PGC1α, and C/EBPβ in NRVMs with lncExACT1 KD and/or DCHS2 OE. *p<0.05, **p<0.01 vs Control/Vector. n=3 independent replicates per group. Data are shown as mean±SEM.
Figure 13B:
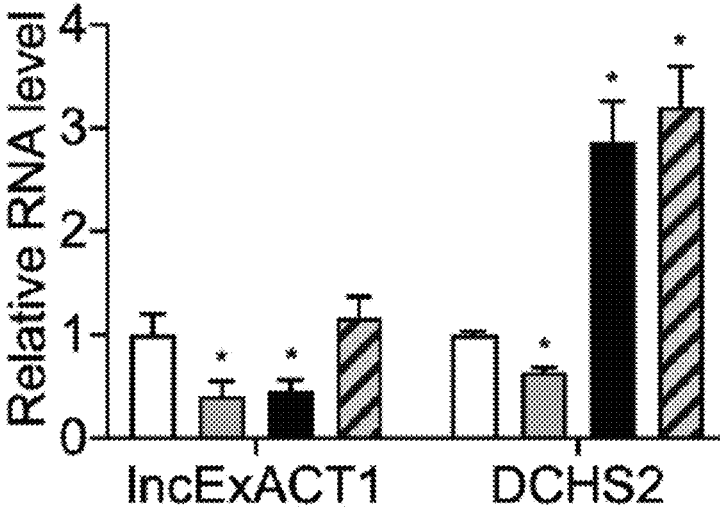

Although gene expression studies suggested miR-222 contributes to lncExACT1's effects in cardiomyocytes, our prior work demonstrated that miR-222—unlike inhibition of lncExACT1—is not sufficient to recapitulate the cardiac effects of exercise in vivo[12], underscoring the potential importance of miR-222-independent mechanisms. lncRNAs often regulate expression of nearby genes[32], and we investigated DCHS2 (Dachsous cadherin-related 2), a protein-coding gene of the cadherin superfamily, which is the protein-coding gene closest to lncExACT1. Similar to lncExACT1, cardiac DCHS2 expression was increased in patients and mice with HF but decreased in exercised mice (FIG. 6A). Moreover, cardiac DCHS2 decreased in mice after lncExACT1 knockdown but increased with AAV-lncExACT1 expression (FIG. 6A). Similar effects were seen in primary cardiomyocytes with lncExACT1 overexpression or inhibition, while DCHS2 expression or knockdown did not affect lncExACT1 expression (FIGS. 13A-B). These data suggest DCHS2 expression is regulated by lncExACT1. To determine if lncExACT1 directly regulates DCHS2 transcription, we performed analyses of the DCHS2 promoter region. Sequences corresponding to the 500, 1000, or 1500 base pairs upstream of the DCHS2 transcriptional start site were inserted into a luciferase reporter and transfected into primary cardiomyocytes in combination with either lncEx-ACT1 overexpression or inhibition. lncExACT1 expression increased, while lncExACT1 knockdown decreased, the activity of all the promoter constructs that included 1000 and 1500 bp 5' of DCHS2 but not the construct including 500 bp alone (FIG. 6B). This suggests lncExACT1 positively regulates DCHS2 transcription through sequences lying between 500-1500 bp upstream of the DCHS2 start site.

Figure 6C:
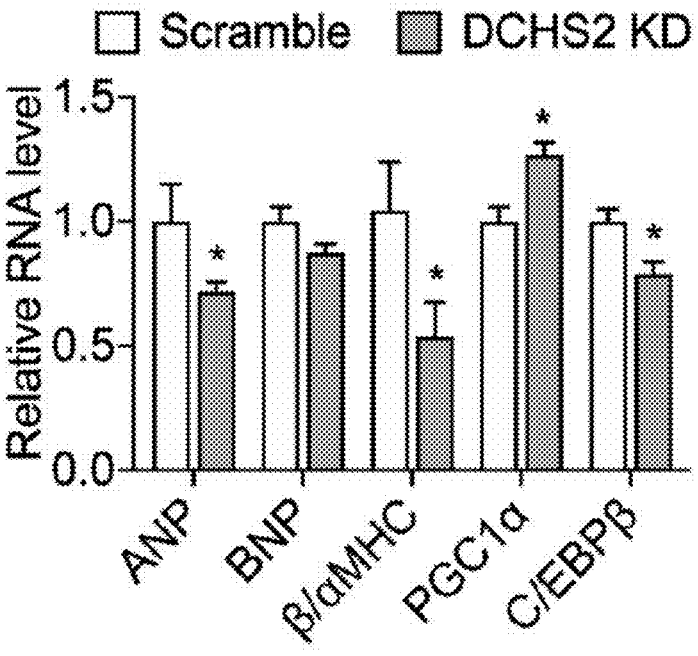
Figure 13C:
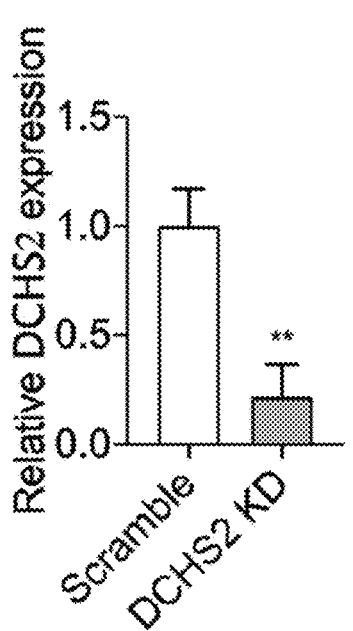
Figure 13D:
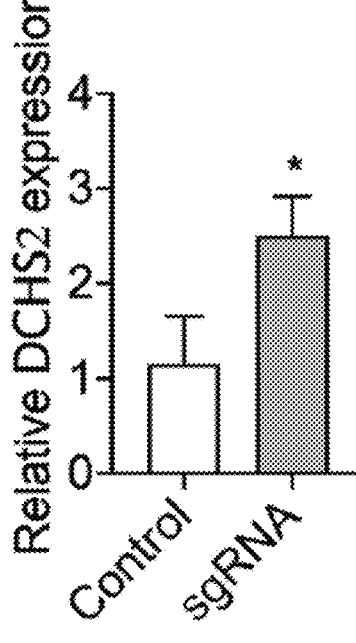
Figure 13E:
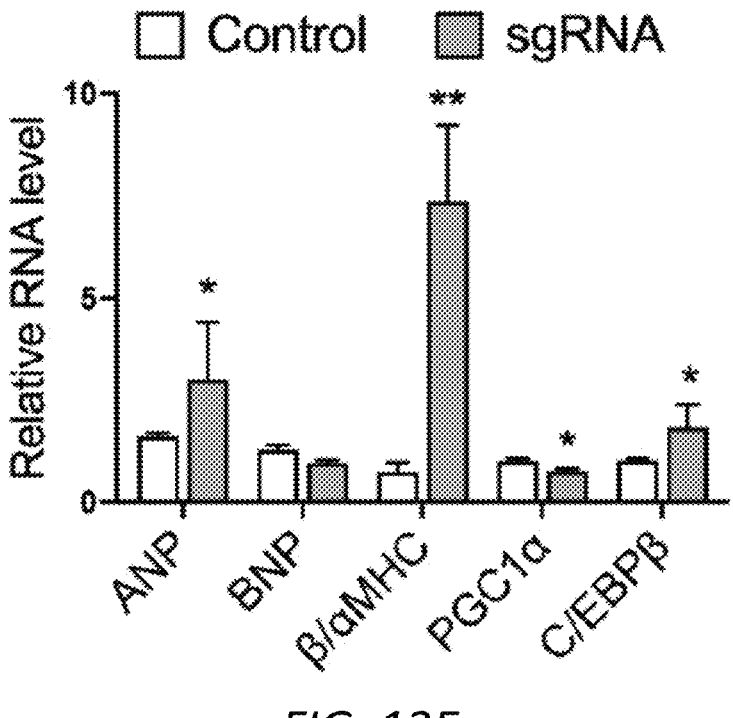
Figure 13F:
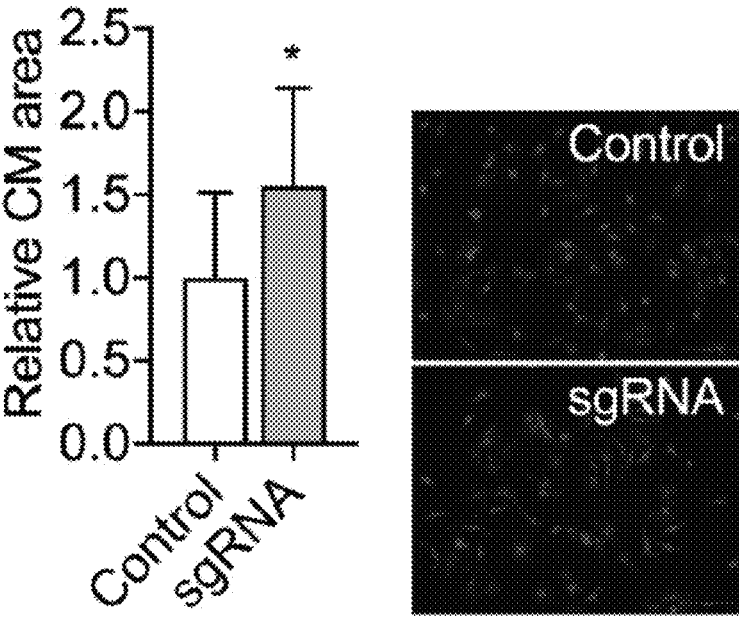
Figure 13G:
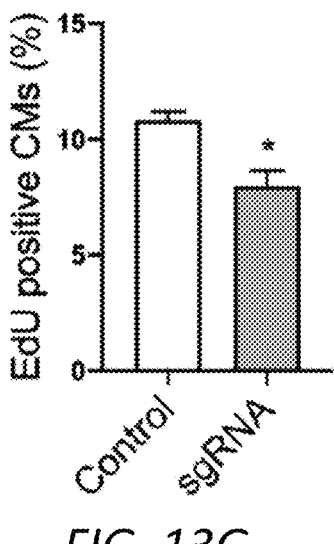
Figure 13H:
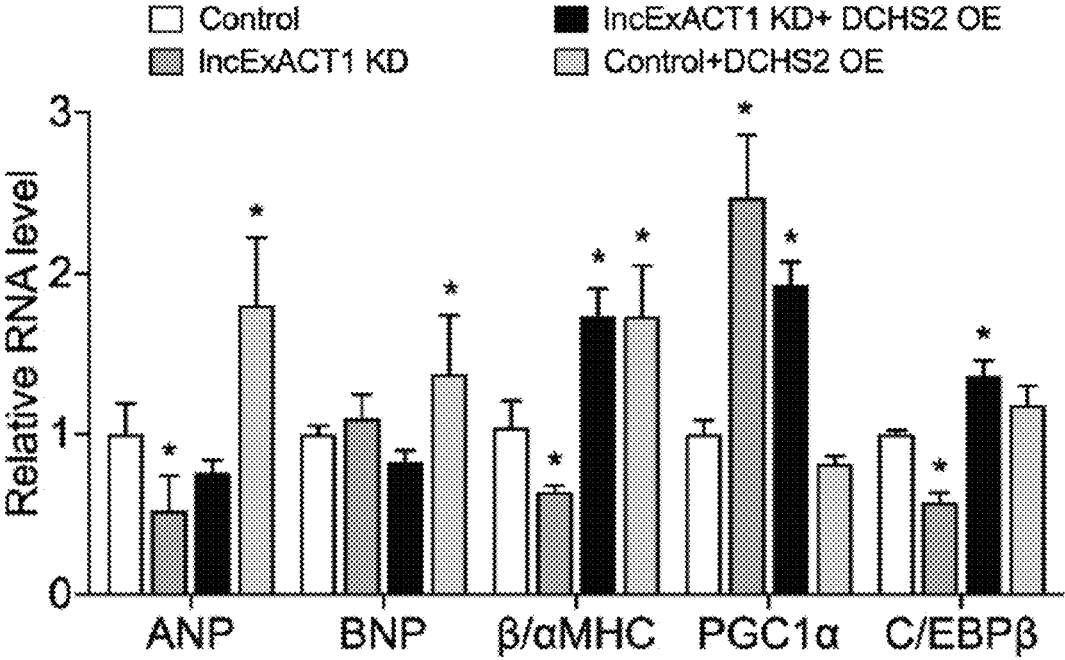

In primary cardiomyocytes, siRNA knockdown of DCHS2 (FIG. 13C) induced an increase in cardiomyocyte size with a physiological gene expression pattern and markers of proliferation (FIGS. 6C-E). In contrast, while overexpression of DCHS2 using CRISPR/dCas9 activation system also increased cardiomyocyte size this was associated with a pathological hypertrophy gene expression pattern and reduced markers of cardiomyocyte proliferation (FIGS. 13D-G). Thus, similar to lncExACT1, DCHS2 inhibition induces physiological cardiomyocyte hypertrophy and proliferation while its overexpression induces pathological cardiomyocyte hypertrophy. We then examined the interacting effects of DCHS2 and lncExACT1 in cardiomyocytes. DCHS2 knockdown prevented the pathological gene expression pattern otherwise seen with lncExACT1 overexpression (FIG. 6F) and DCHS2 expression blocked the physiological hypertrophy gene expression pattern seen with lncExACT1 knockdown (FIG. 13H). Together these data suggest DCHS2 contributes to the effects of lncExACT1 in cardiomyocytes.

Figure 6G:
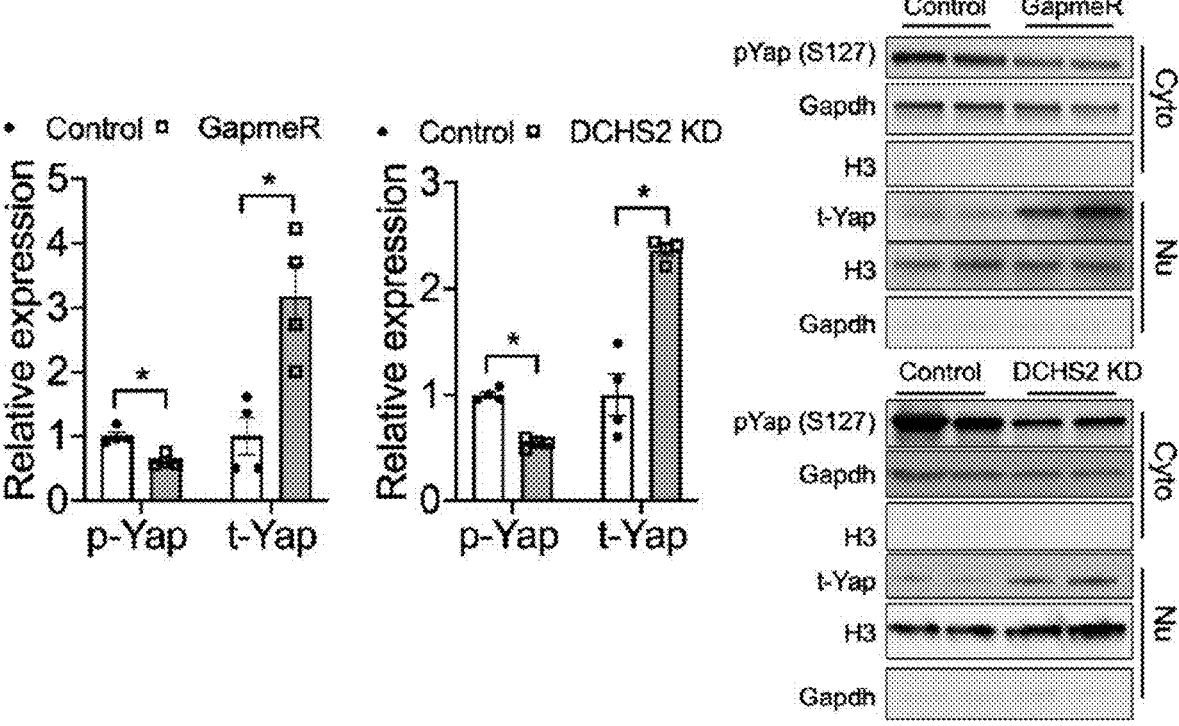
Figure 14A:
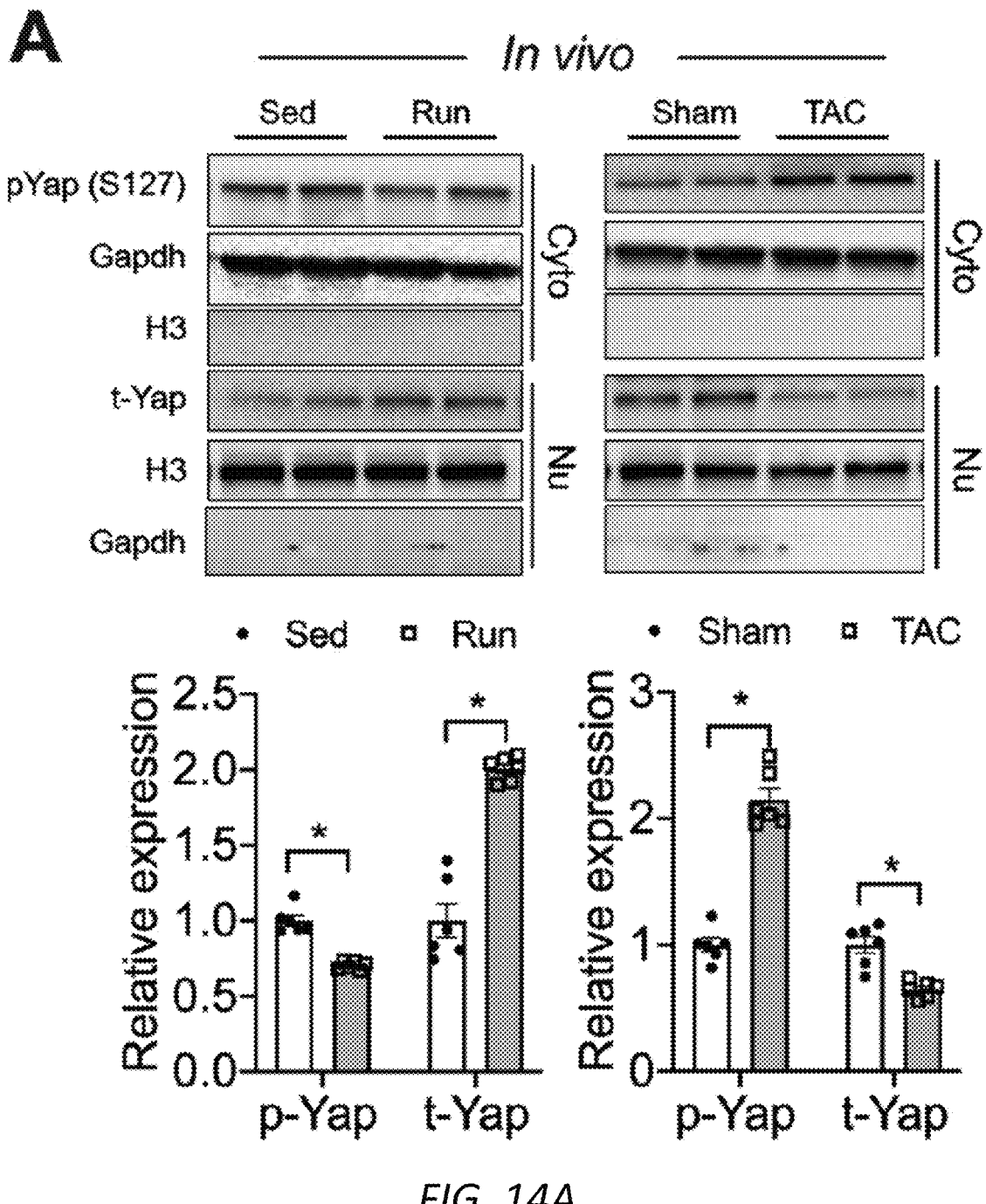
Figure 14D:
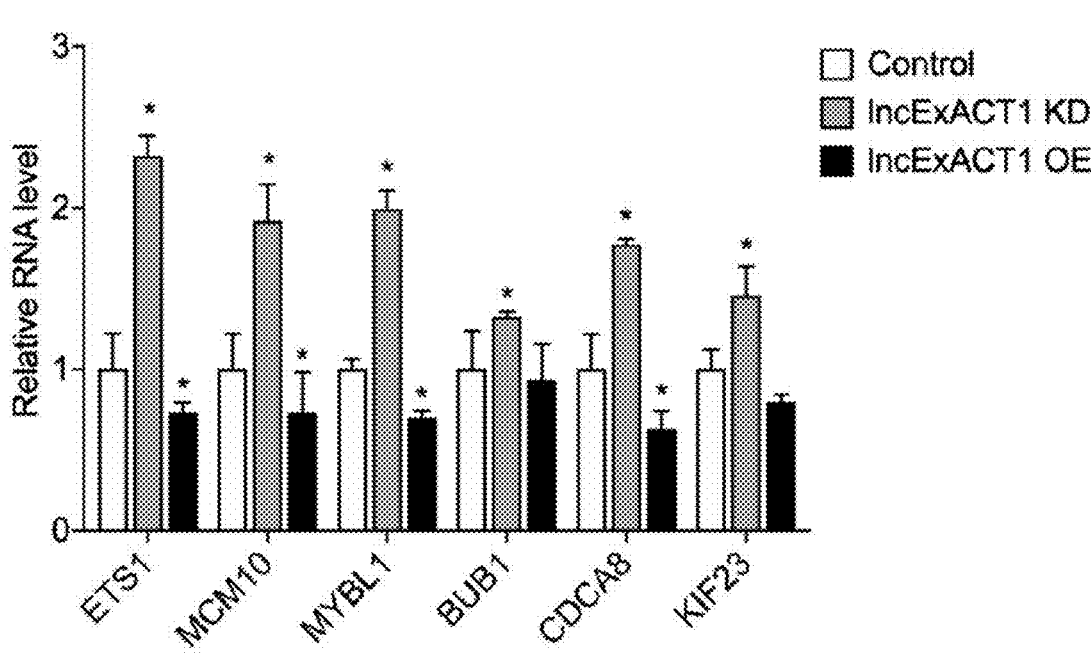
Figure 14E:
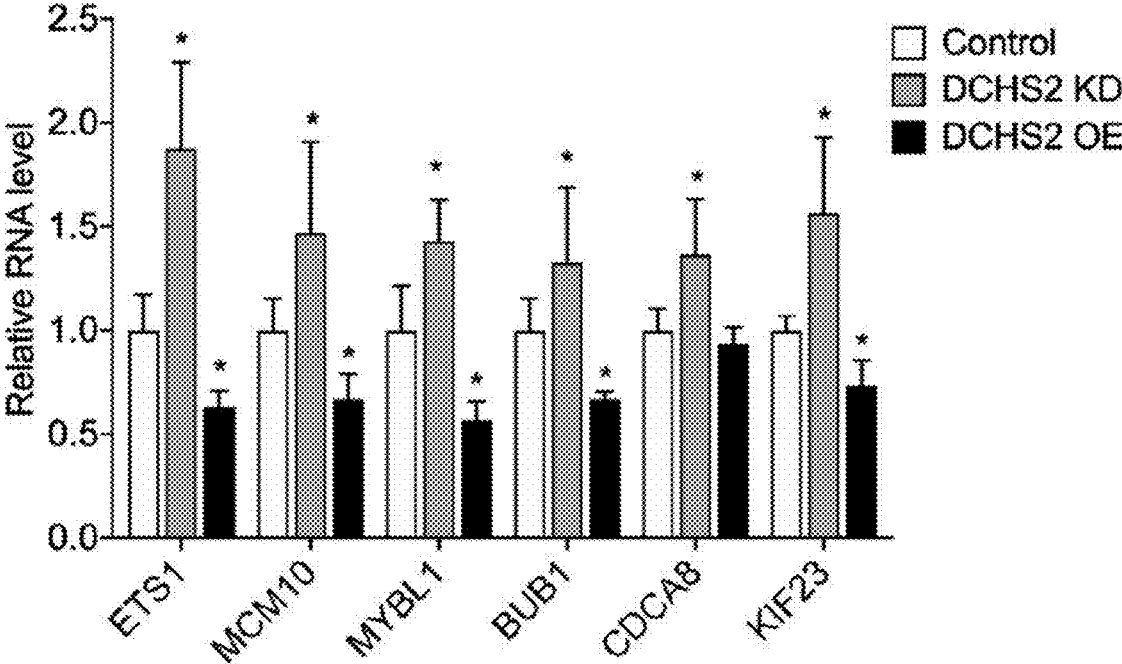

Although it has no known role in the heart, in other systems, DCHS2 is an upstream positive regulator of Hippo signaling[33], a highly conserved regulator of size and proliferation in many organs including the heart.[34, 35] Hippo activation ultimately induces phosphorylation and cytoplasmic sequestration of Yap1, which reduces proliferation, while its inhibition culminates in dephosphorylation and nuclear translocation of Yap1 driving cell cycle progression[36]. Total nuclear Yap1 was increased while phosphorylation of cytoplasmic Yap1 at ser127 (p-Yap1) was reduced in exercised hearts while the reverse was seen in failing hearts after TAC[37, 38] (FIG. 14A). lncExACT1 inhibition in vivo also increased total nuclear Yap1 and reduced cytoplasmic p-Yap1; conversely lncExACT1 overexpression increased cytoplasmic p-Yap1 and decreased total nuclear Yap1 (FIG. 14B). Similarly, either lncExACT1 or DCHS2 inhibition in primary cardiomyocytes reduced cytoplasmic p-Yap1 and increased nuclear total Yap1 (FIG. 6G). In contrast, lncExACT1 or DCHS2 overexpression increased cytoplasmic p-Yap1 and reduced total nuclear Yap1 in primary cardiomyocytes (FIG. 14C). These data suggest that physiological hypertrophy enhances while pathological hypertrophy inhibits Yap1 transcriptional activity through lncExACT1-DCHS2. Consistent with this model, knockdown of either lncExACT1 or DCHS2 in cardiomyocytes increased expression of multiple downstream targets of Yap1[36, 39], while lncExACT1 or DCHS2 expression had the opposite effect (FIGS. 14D-E). Taken together these data implicate lncExACT1-DCHS2 as novel regulators of cardiac Yap1, which likely contributes to exercise-induced heart growth and cardiomyogenesis.

Figure 15A:
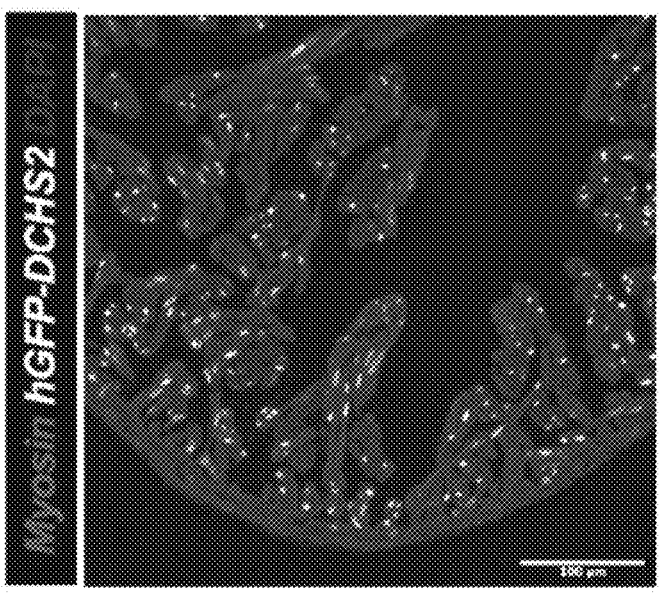
FIGS. 15A-G. DCHS2 overexpression induces pathological cardiac hypertrophy and reduces regenerative capacity in zebrafish. A. Representative image from apex region of an adult transgenic zebrafish heart immunostained for tropomyosin (Red), GFP (Green), and nuclei (DPAI, Blue). B. Representative image and quantification of cardiomyocytes size isolated from wild-type control (CTRL, white arrow) or DCHS2 overexpression (hGFP-DCHS2, yellow arrow) zebrafishes. C. QRT-PCR measurement of ANP and BNP in hearts from CTRL and hGFP-DCHS2 zebrafishes. D. Representative images and quantification of nkx2.5 and PCNA double positive cardiomyocytes in hearts at 7 days post injury (dpi) from CTRL and hGFP-DCHS2 zebrafish. E. Representative images and quantification of fibrosis in hearts at 60 days post injury (dpi) from CTRL and hGFP-DCHS2 zebrafish. F and G. Representative images and quantification of nuclear total Yap1 and cytoplasmic p-Yap1 protein expression in hearts from CTRL and hGFP-DCHS2 zebrafish. *p<0.05, **p<0.01 by Student's ttest. Data shown as mean±SEM.
Figure 15B:
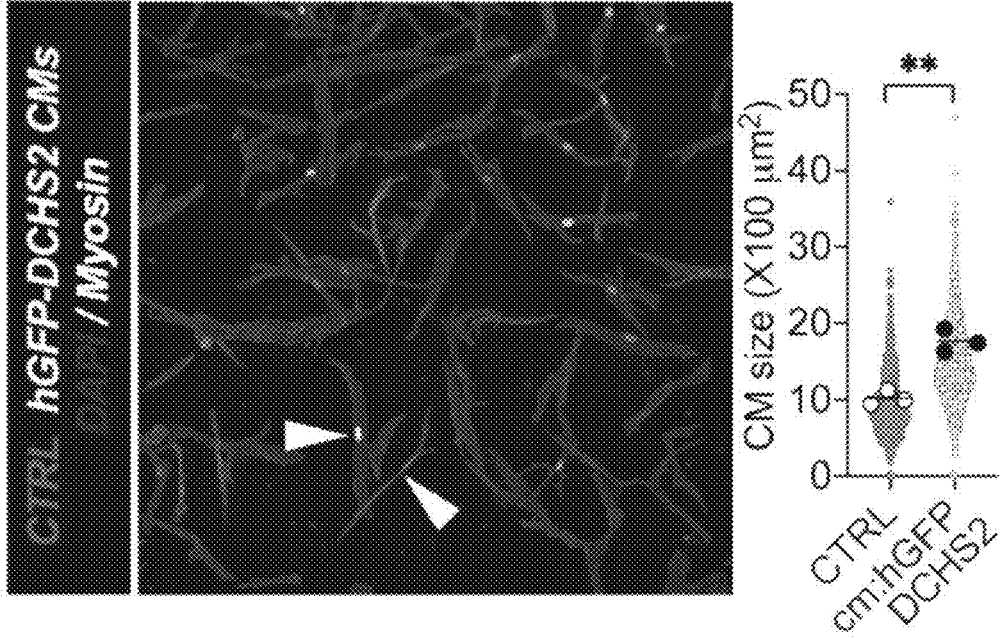
Figure 15C:
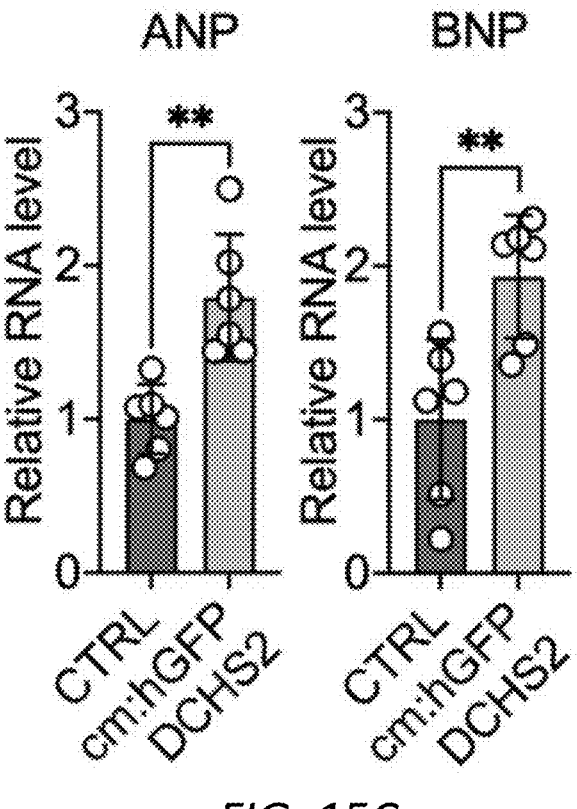
Figure 15D:
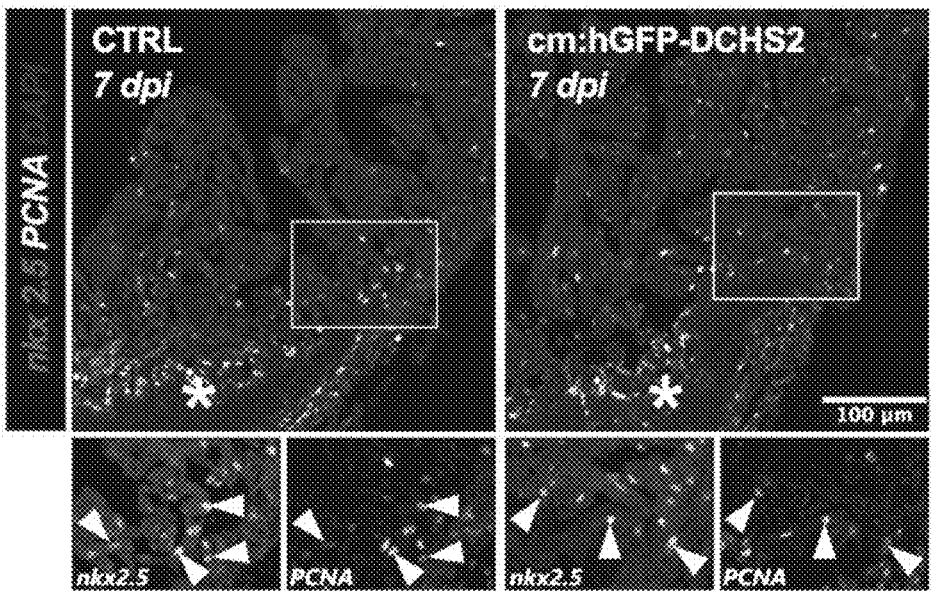
Figure 15D:
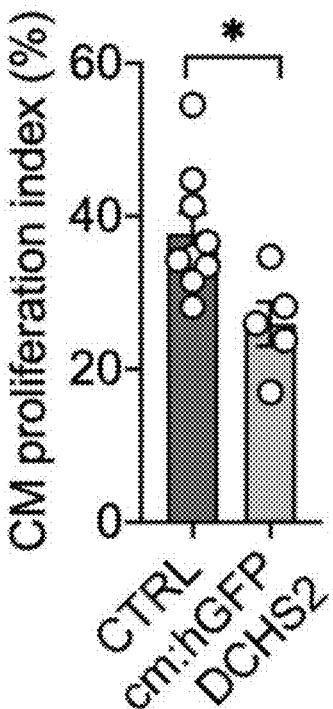
Figure 15E:
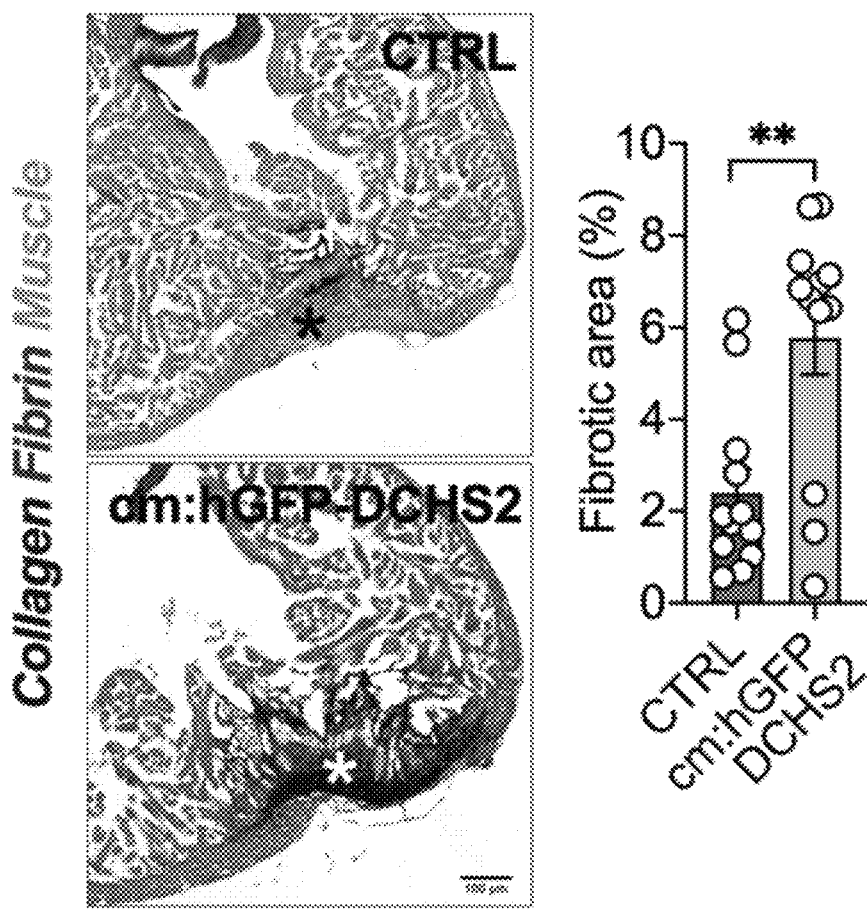
Figure 15F:
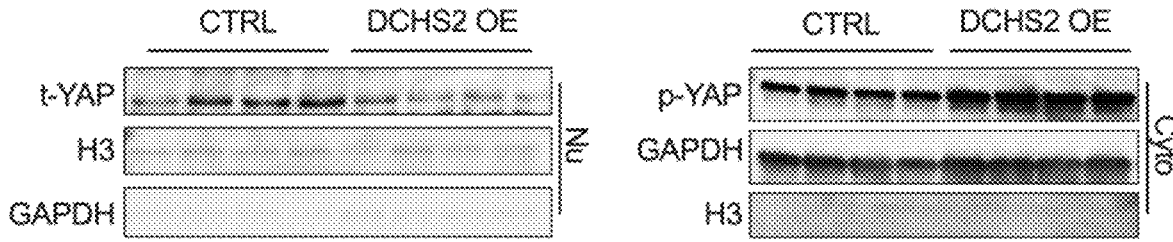
Figures 15G, 16A:
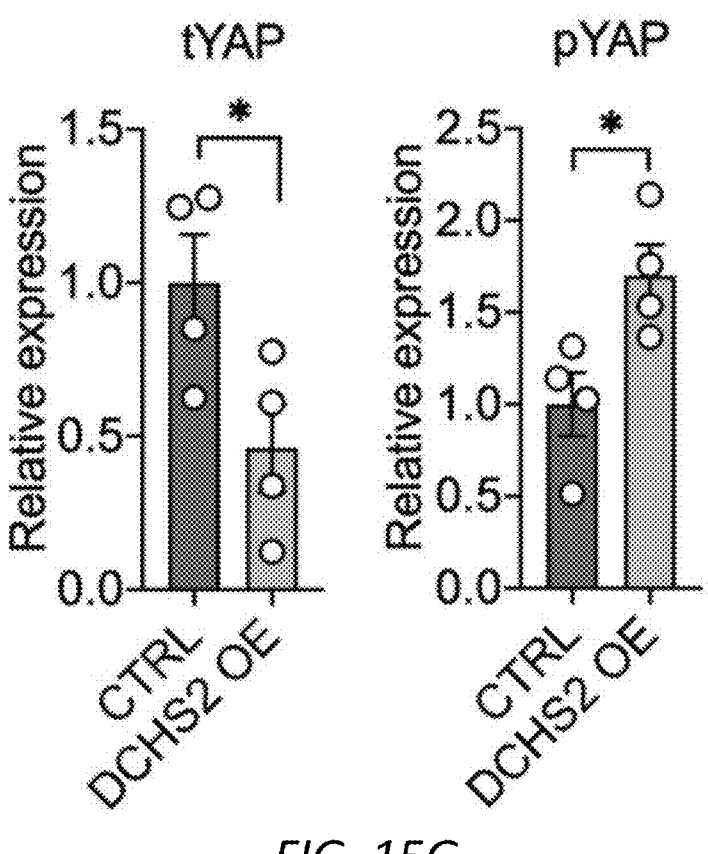
FIGS. 16A-L. DCHS2 knockdown promotes physiological cardiac hypertrophy. A. Schematic of experimental strategy employed to knockdown DCHS2 in the hearts in vivo. B. QRT-PCR measurement of cardiac DCHS2 in Cas9 knockin mice with injection of AAV9 carrying gRNA1 or gRNA2. C. Heart weight (HW) relative to tibial length (TL). D. Quantification of cardiomyocyte area from wheat germ agglutinin (WGA)-stained heart sections. E. Lung weight (LW) relative to tibial length (TL). F. Fractional shortening (FS). G. Relative wall thickness (RWT). H. Left ventricular end diastolic internal dimension (LVIDd). I. QRT-PCR measurement of hypertrophy gene markers. J. Quantification of Ki67, PCM1 double-positive cardiomyocytes in stained heart sections. K and L. Representative images and quantification of nuclear total Yap1 and cytoplasmic p-Yap1 protein expressions in hearts from mice injected with AAV9 carrying control, or gRNA1, or gRNA2. *p<0.05 by one-way analysis of variance (ANOVA) with post hoc Tukey. Data shown as mean±SEM.

Example 7. DCHS2 Overexpression Induces Pathological Cardiac Hypertrophy and Impairs Cardiac Regeneration in Zebrafish In vitro studies in primary cardiomyocytes suggested that overexpression of DCHS2 induced pathological cardiomyocyte hypertrophy and inhibited cardiomyocyte proliferation. To gain insight into the function of DCHS2 overexpression in the heart in vivo, we turned to the zebrafish model, known for its remarkable ability to regenerate the heart after cardiac injury[47] through cardiomyocyte proliferation[48]. We generated a zebrafish line constitutively expressing human DCHS2 in cardiomyocytes (FIG. 15A). Compared to adult wild-type controls, cardiac overexpression of DCHS2 increased cardiomyocyte size and expression of ANP and BNP, consistent with pathological cardiac hypertrophy (FIGS. 15B-C). Seven days post cardiac cryoinjury (dpi), many proliferating cardiomyocytes (nxk2.5 and PCNA double positive) were evident in the injury area and border zone in wild-type animals. In contrast, significantly fewer were seen in DCHS2-expressing animals (FIG. 15D). We then asked whether the DCHS2-induced defect in cardiomyocyte proliferation would translate into long-term regeneration defects. At 90 dpi, all hearts (12 of 12) from wild-type animals had repaired the myocardial wall and showed only minimal residual fibrosis. In contrast, animals overexpressing DCHS2 developed substantially more fibrosis (FIG. 15E). These results indicate that DCHS2 impairs cardiac regeneration and promotes scarring after injury in zebrafish. Cardiac DCHS2 overexpression also reduced total nuclear Yap1 and increased cytoplasmic p-Yap1 (FIGS. 15F-G). Altogether, these results indicate that cardiac overexpression of DCHS2 in zebrafish promotes pathological cardiac hypertrophy in unperturbed hearts, and impairs cardiomyocyte proliferation and regeneration, increasing fibrosis after cryoinjury. Consistent with the mammalian studies, it seems likely that these effects are mediated through suppression of nuclear Yap1.

Example 8. DCHS2 Knock-Down Promotes Physiological Cardiac Hypertrophy

Figures 16B, 16C:
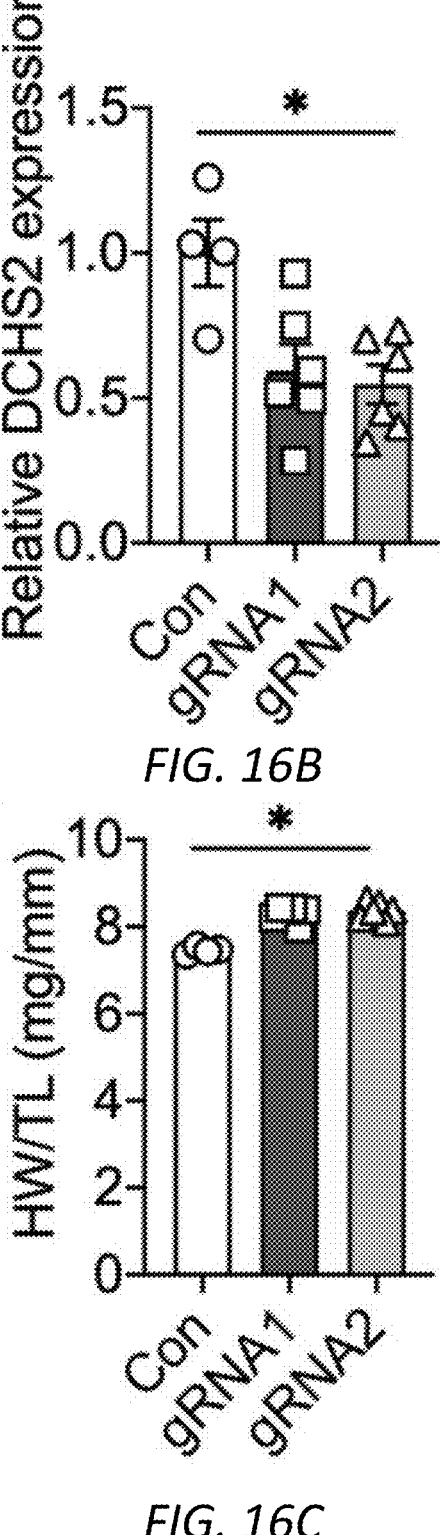
Figure 16D:
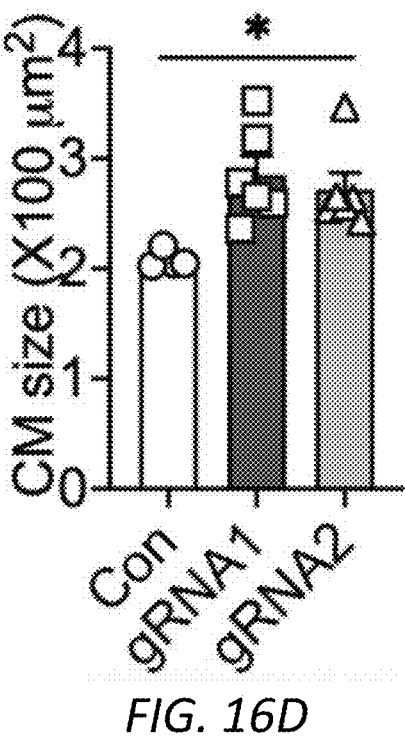
Figure 16E:
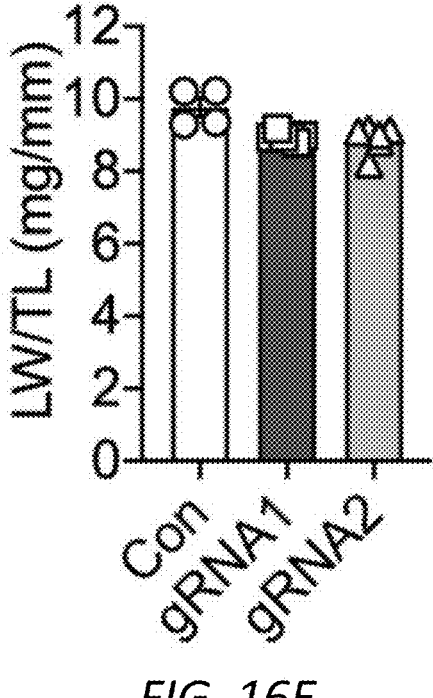
Figure 16F:
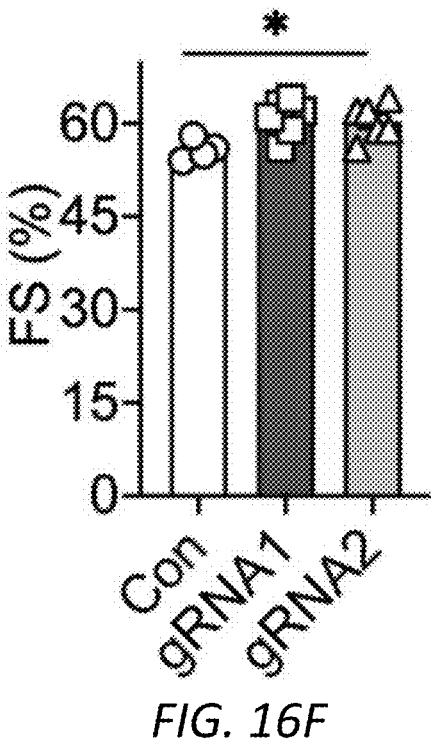
Figure 16G:
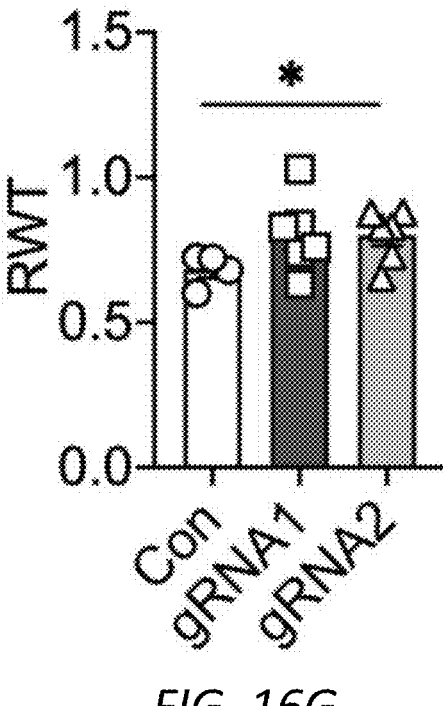
Figure 16H:
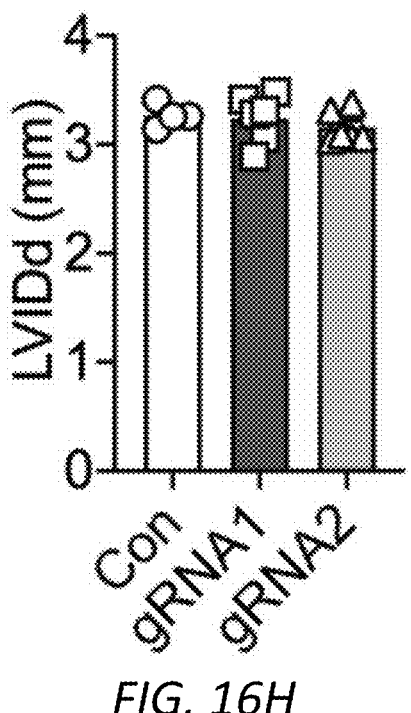
Figure 16I:
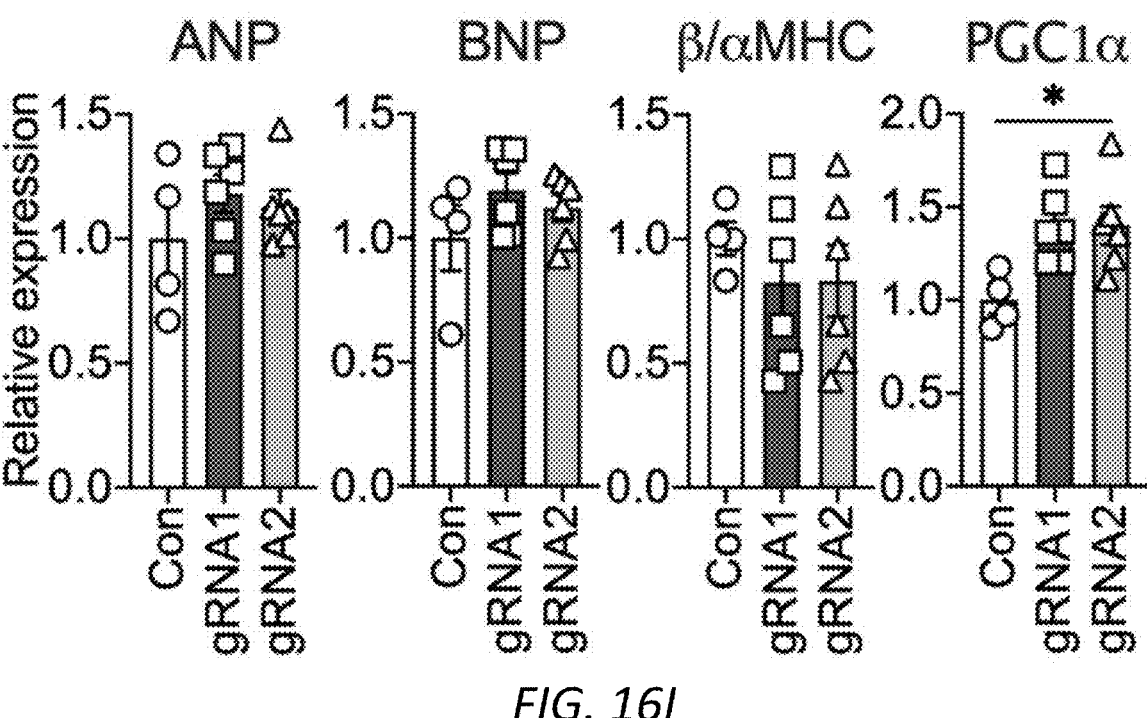
Figure 16J:
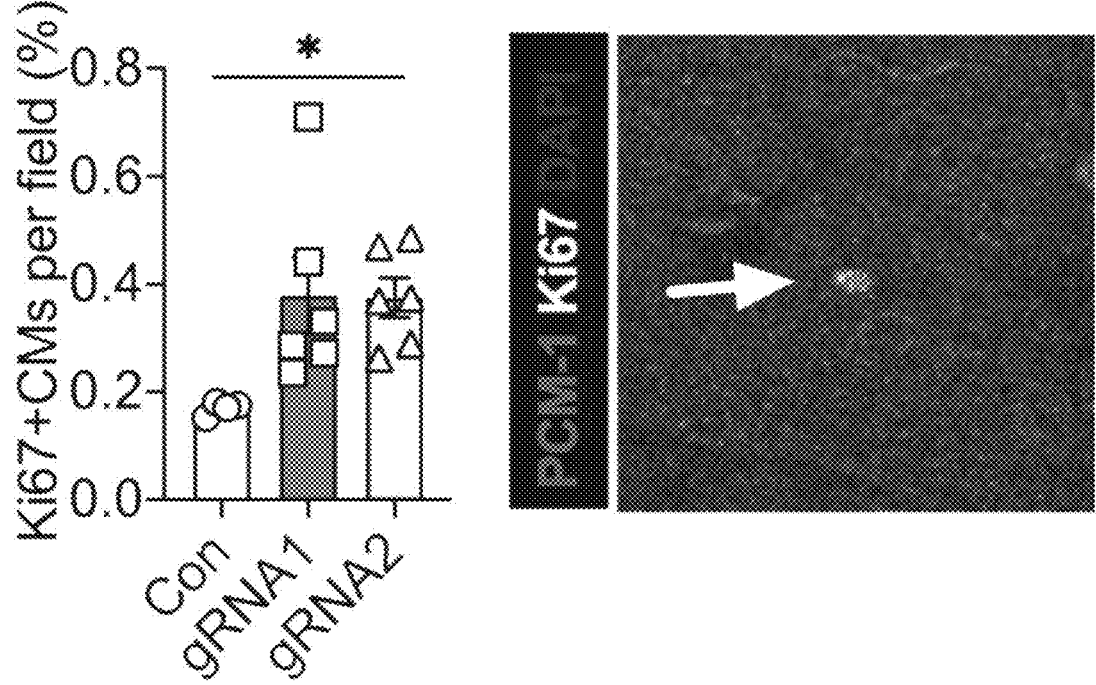
Figure 16K:
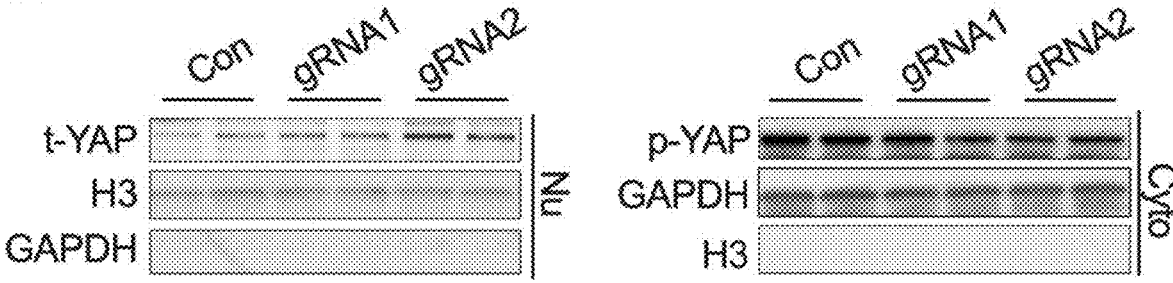
Figure 16L:
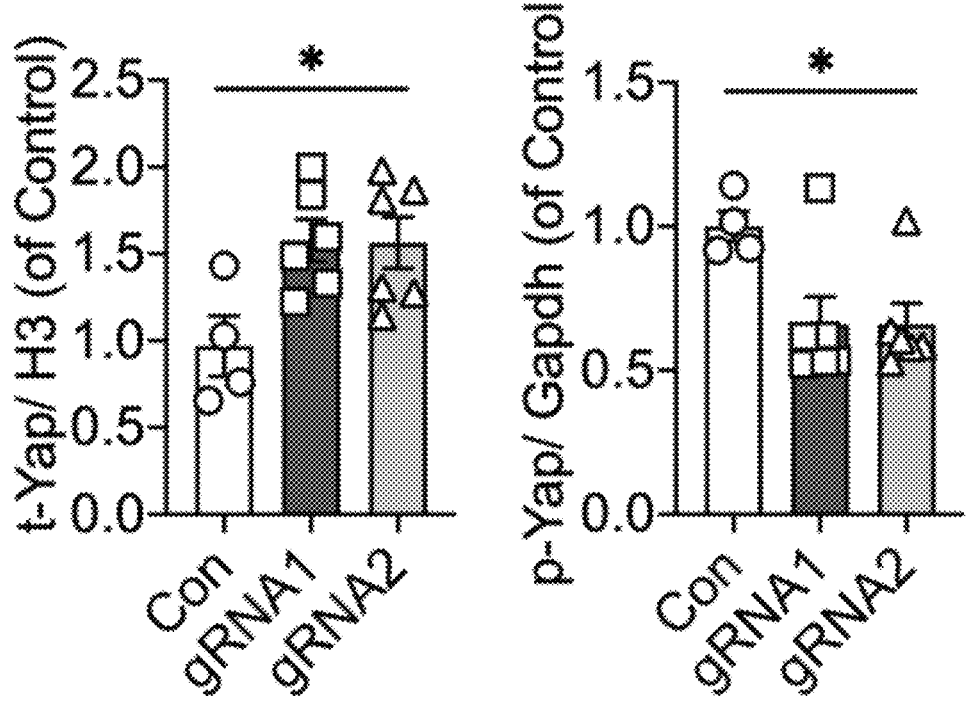

To examine the effects of DCHS2 inhibition in vivo we turned back to the adult murine model, which has limited cardiomyocyte proliferation at baseline. We injected Cas9 knock-in mice[49, 50] with AAV9 vectors encoding either control gRNAs, gRNAs targeting DCHS2 exon 2 (gRNA1), or gRNAs targeting DCHS2 exon 3 (gRNA2) along with a cardiac-specific troponin promoter-driven Cre expression cassette (FIG. 16A). Eight weeks after AAV injection, cardiac DCHS2 was reduced by ~50% in mice with gRNA1 or gRNA2 (FIG. 16B), which is comparable to the reduction seen in exercised hearts. Reduced cardiac DCHS2 led to increased HW/TL (FIG. 16C) and increased cardiomyocyte size (FIG. 16D) without affecting LW/TL (FIG. 16E). Reduced cardiac DCHS2 also improved cardiac function (FIG. 16F) and increased relative wall thickness (FIG. 16G) without a significant change in chamber dimension (FIG. 16H). Reduced DCHS2 induced a gene expression pattern suggestive of physiological hypertrophy with increased PGC1α but no change in ANP, BNP, or β/αMHC (FIG. 16I). These changes were qualitatively similar to those seen with comparable lncExACT1 knockdown but smaller quantitatively. Notably, DCHS2 knockdown increased cardiomyocyte proliferation as indicated by Ki67 in PCM1 positive cells (FIG. 16J) to a similar degree as seen with lncExACT1 knockdown. Consistent with the in vitro and zebrafish studies, knockdown of DCHS2 increased nuclear total Yap1 but reduced cytoplasmic p-Yap1 expression in the heart (FIGS. 16K-L). Taken together, these data demonstrate that knockdown of DCHS2 in the adult mammalian heart is sufficient to induce physiological cardiac hypertrophy and evidence of cardiomyocyte proliferation. While the cardiomyocyte growth is modest, the increase in markers of proliferation appears quantitatively similar to and thus likely sufficient to account for the growth seen with lncExACT1 knockdown. The corresponding changes in nuclear Yap1 observed are likely sufficient to explain the proliferation changes seen with DCHS2 manipulation in both zebrafish and mammalian models.

<div style="text-align:center">REFERENCES</div>

1. Virani et al., Heart disease and stroke statistics-2020 update: A report from the american heart association. Circulation. 2020; 141:e139-e596
2. Mozaffarian et al., American Heart Association Statistics C, Stroke Statistics S. Heart disease and stroke statistics—2015 update: A report from the american heart association. Circulation. 2015; 131:e29-322
3. Pandey et al., Relationship between physical activity, body mass index, and risk of heart failure. J Am Coll Cardiol. 2017; 69:1129-1142
4. Wang et al., Aerobic exercise protects against pressure overload-induced cardiac dysfunction and hypertrophy via beta3-ar-nnos-no activation. PLoS One. 2017; 12:e0179648
5. Iemitsu et al., Physiological and pathological cardiac hypertrophy induce different molecular phenotypes in the rat. Am J Physiol Regul Integr Comp Physiol. 2001; 281:R2029-2036
6. Song et al., Deep rna sequencing reveals novel cardiac transcriptomic signatures for physiological and pathological hypertrophy. PloS one. 2012; 7:e35552
7. Bostrom et al., C/ebpbeta controls exercise-induced cardiac growth and protects against pathological cardiac remodeling. Cell. 2010; 143:1072-1083
8. Grazette and Rosenzweig, Role of apoptosis in heart failure. Heart Fail Clin. 2005; 1:251-261
9. Narula et al., Apoptosis in myocytes in end-stage heart failure. New England Journal Of Medicine. 1996; 335: 1182-1189
10. Eschenhagen et al., Cardiomyocyte regeneration: A consensus statement. Circulation. 2017; 136:680-686
11. Vujic et al., Exercise induces new cardiomyocyte generation in the adult mammalian heart. Nat Commun. 2018; 9:1659
12. Liu X et al., Mir-222 is necessary for exercise-induced cardiac growth and protects against pathological cardiac remodeling. Cell Metab. 2015; 21:584-595
13. Roh et al., Exercise training reverses cardiac aging phenotypes associated with heart failure with preserved ejection fraction in male mice. Aging Cell. 2020
14. Steinhauser M L, Bailey A P, Senyo S E, Guillermier C, Perlstein T S, Gould A P, Lee R T, Lechene C P. Multiisotope imaging mass spectrometry quantifies stem cell division and metabolism. Nature. 2012; 481:516-519
15. Klattenhoff et al., Braveheart, a long noncoding rna required for cardiovascular lineage commitment. Cell. 2013; 152:570-583
16. Cai et al., The long noncoding rna carel controls cardiac regeneration. Journal of the American College of Cardiology. 2018; 72:534-550
17. Wang et al., The long noncoding rna nrf regulates programmed necrosis and myocardial injury during ischemia and reperfusion by targeting mir-873. Cell Death Differ. 2016; 23:1394-1405
18. Han et al., A long noncoding rna protects the heart from pathological hypertrophy. Nature. 2014; 514:102-106
19. Sallam et al., Long noncoding rna discovery in cardiovascular disease: Decoding form to function. Circ Res. 2018; 122:155-166
20. Viereck and Thum, Long noncoding rnas in pathological cardiac remodeling. Circ Res. 2017; 120:262-264
21. Roh et al., Activin type ii receptor signaling in cardiac aging and heart failure. Sci Transl Med. 2019; 11
22. Bezzerides et al., Cited4 induces physiologic hypertrophy and promotes functional recovery after ischemic injury. JCI Insight. 2016; 1
23. Jiang et al., Allele-specific silencing of mutant myh6 transcripts in mice suppresses hypertrophic cardiomyopathy. Science. 2013; 342:111-114
24. Pleger et al., Cardiac aav9-s100a1 gene therapy rescues post-ischemic heart failure in a preclinical large animal model. Sci Transl Med. 2011; 3:92ra64
25. Viereck et al., Long noncoding rna chast promotes cardiac remodeling. Sci Transl Med. 2016; 8:326ra322
26. Rinaldi and Wood, Antisense oligonucleotides: The next frontier for treatment of neurological disorders. Nat Rev Neurol. 2018; 14:9-21
27. Mann and Rosenzweig, Can exercise teach us how to treat heart disease?Circulation. 2012; 126:2625-2635
28. Wei et al., What do we know about the cardiac benefits of exercise? Trends Cardiovasc Med. 2015; 25:529-536
29. Campos et al., Exercise reestablishes autophagic flux and mitochondrial quality control in heart failure. Autophagy. 2017; 13:1304-1317
30. Bansal et al., Proteomic analysis reveals late exercise effects on cardiac remodeling following myocardial infarction. J Proteomics. 2010; 73:2041-2049
31. Yengo et al., Exercise training post-mi favorably modifies heart extracellular matrix in the rat. Med Sci Sports Exerc. 2012; 44:1005-1012
32. Devaux et al., Long noncoding RNAs in cardiac development and ageing. Nat Rev Cardiol. 2015; 12:415-425

33. Bagherie-Lachidan et al., Stromal fat4 acts non-autonomously with dchsl/2 to restrict the nephron progenitor pool. Development. 2015; 142:2564-2573

34. Heallen et al., Hippo pathway inhibits wnt signaling to restrain cardiomyocyte proliferation and heart size. Science. 2011; 332:458-461

35. Monroe et al., Yap partially reprograms chromatin accessibility to directly induce adult cardiogenesis in vivo. Dev Cell. 2019; 48:765-779 e767

36. Wang et al., The hippo pathway in the heart: Pivotal roles in development, disease, and regeneration. Nat Rev Cardiol. 2018; 15:672-684

37. Morikawa et al., Dystrophin-glycoprotein complex sequesters yap to inhibit cardiomyocyte proliferation. Nature. 2017; 547:227-231

38. Ikeda et al., Hippo deficiency leads to cardiac dysfunction accompanied by cardiomyocyte dedifferentiation during pressure overload. Circ Res. 2019; 124:292-305

39. Totaro et al., Yap/taz upstream signals and downstream responses. Nat Cell Biol. 2018; 20:888-899

40. Tsao et al., Left ventricular structure and risk of cardiovascular events: A framingham heart study cardiac magnetic resonance study. J Am Heart Assoc. 2015; 4:e002188

41. Gibb and Hill, Metabolic coordination of physiological and pathological cardiac remodeling. Circ Res. 2018; 123:107-128

42. Nakamura and Sadoshima, Mechanisms of physiological and pathological cardiac hypertrophy. Nat Rev Cardiol. 2018; 15:387-407

43. Grote et al., The tissue-specific lncrna fendrr is an essential regulator of heart and body wall development in the mouse. Dev Cell. 2013; 24:206-214

44. Micheletti et al., The long noncoding rna wisper controls cardiac fibrosis and remodeling. Sci Transl Med. 2017; 9

45. Blair and McNeill, Big roles for fat cadherins. Curr Opin Cell Biol. 2018; 51:73-80

46. Sharma and McNeill, Fat and dachsous cadherins. Prog Mol Biol Transl Sci. 2013; 116:215-235

47. Poss K D, Wilson L G, Keating M T. Heart regeneration in zebrafish. Science. 2002; 298(5601):2188-90. Epub 2002/12/14.

48. Kikuchi K, Holdway J E, Werdich A A, Anderson R M, Fang Y, Egnaczyk G F, Evans T, Macrae C A, Stainier D Y, Poss K D. Primary contribution to zebrafish heart regeneration by gata4(+) cardiomyocytes. Nature. 2010; 464(7288):601-5. Epub 2010/03/26.

49. Platt et al. CRISPR-Cas9 knockin mice for genome editing and cancer modeling. Cell. 2014; 159(2):440-55. Epub 2014/09/30.

50. Guo et al., Intercalated disc protein Xinbeta is required for Hippo-YAP signaling in the heart. Nature communications. 2020; 11(1):4666. Epub 2020/09/18.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An inhibitory nucleic acid targeting IncExACTI (SEQ ID NO:1) that is 20 to 50 nucleotides in length, comprising a region of at least 20 consecutive nucleotides complementary to the IncExACTI, wherein the inhibitory nucleic acid is an antisense oligonucleotide or siRNA.

2. The inhibitory nucleic acid of claim 1, which is an antisense oligonucleotide.

3. The inhibitory nucleic acid of claim 1, which is a siRNA that is a double-stranded ribonucleic acid (dsRNA), wherein said dsRNA comprises a sense strand and an antisense strand, the antisense strand comprising the region of complementarity to SEQ ID NO:1.

4. The inhibitory nucleic acid of claim 1, wherein the region of complementarity is 20 to 21 nucleotides in length.

5. The inhibitory nucleic acid of claim 3, wherein each strand is no more than 30 nucleotides in length.

6. The inhibitory nucleic acid of claim 3, wherein at least one strand comprises a 3' overhang of at least 1 nucleotide.

7. The inhibitory nucleic acid of claim 3, wherein at least one strand comprises a 3' overhang of at least 2 nucleotides.

8. The inhibitory nucleic acid of claim 1, which comprises at least one modification.

9. The inhibitory nucleic acid of claim 8, wherein the modification comprises a modified base or modified bond.

10. The inhibitory nucleic acid of claim 9, wherein the modified bases comprises one or more of a locked nucleotide, 2'-O-methyl modified nucleotide, a nucleotide comprising a 5'-phosphate group, a 2'-deoxy-2'-fluoro modified nucleotide, a 2'-deoxy-modified nucleotide, an abasic nucleotide, 2'-amino-modified nucleotide, 2'-alkyl-modified nucleotide, morpholino nucleotide, a phosphoramidate, and a non-natural base comprising nucleotide.

11. The inhibitory nucleic acid of claim 10, which is a gapmer or mixmer.

12. The inhibitory nucleic acid of claim 9, wherein the modified bonds comprise at least one phosphorothioate bond.

13. The inhibitory nucleic acid of claim 7, wherein the modification comprises conjugation of one or more lipids or aminosugars.

14. The inhibitory nucleic acid of claim 1, comprising SEQ ID NO:5.

15. A composition comprising the inhibitory nucleic acid of claim 1, and a pharmaceutically acceptable carrier.

16. The composition of claim 15, wherein the inhibitory nucleic acids are conjugated to or encapsulated within a lipid.

17. The composition of claim 15, comprising stable nucleic acid-lipid particle (SNALP).

18. A vector comprising a sequence encoding the inhibitory nucleic acid of claim 1.

19. The vector of claim 18, wherein the sequence encoding the inhibitory nucleic acid is operably linked to one or more sequences for expression of inhibitory nucleic acid.

20. An isolated cell comprising the vector of claim 18.

21. A method of reducing expression of IncExACTI and/or Dachsous cadherin-related 2 (DCHS2) in a cardiomyocyte, the method comprising administering to the cell a therapeutically effective amount of the inhibitory nucleic acid of claim 1.

22. A method of improving cardiac function in a subject, the method comprising administering to the subject a therapeutically effective amount of the inhibitory nucleic acid of claim 1.

23. The method of claim 22, wherein the subject has pathological hypertrophy or heart failure, myocardial infarction (MI) or post-infarction remodeling, congenital or acquired cardiomyopathy; valvular heart disease and remodeling; and atrial and ventricular arrhythmias (optionally atrial fibrillation or ventricular tachycardia).

24. The inhibitory nucleic acid of claim 1, comprising SEQ ID NO:3.

25. The inhibitory nucleic acid of claim 24, which is an LNA gapmer.

26. The inhibitory nucleic acid of claim 14, which is an LNA gapmer.

27. The method of claim 21, wherein the cell is in a subject.

\* \* \* \* \*